(12) United States Patent
Thompson et al.

(10) Patent No.: US 8,445,638 B2
(45) Date of Patent: May 21, 2013

(54) USE OF A TRUNCATED EIF-5A1 POLYNUCLEOTIDE TO INDUCE APOPTOSIS IN CANCER CELLS

(75) Inventors: John E. Thompson, Waterloo (CA); Zhong Sun, Waterloo (CA); Catherine A. Taylor, Waterloo (CA); Richard Dondero, Waterloo, CA (US); Zhenyu Cheng, Waterloo (CA)

(73) Assignee: Senesco Technologies, Inc., Bridgewater, NJ (US)

( * ) Notice: Subject to any disclaimer, the term of this patent is extended or adjusted under 35 U.S.C. 154(b) by 13 days.

(21) Appl. No.: 12/552,746

(22) Filed: Sep. 2, 2009

(65) Prior Publication Data

US 2010/0076062 A1    Mar. 25, 2010

Related U.S. Application Data

(63) Continuation-in-part of application No. 12/400,742, filed on Mar. 9, 2009.

(60) Provisional application No. 61/093,749, filed on Sep. 3, 2008.

(51) Int. Cl.
*A61K 38/00* (2006.01)
(52) U.S. Cl.
USPC .................................. 530/350; 514/19.3
(58) Field of Classification Search
None
See application file for complete search history.

(56) References Cited

U.S. PATENT DOCUMENTS

| | | | |
|---|---|---|---|
| 5,849,587 | A | 12/1998 | Hanauske-Abel et al. |
| 6,033,910 | A | 3/2000 | Monia et al. |
| 6,448,040 | B1 | 9/2002 | Young et al. |
| 6,468,983 | B2 | 10/2002 | Silverman et al. |
| 7,381,708 | B2 | 6/2008 | Taylor et al. |
| 2003/0077262 | A1 | 4/2003 | Franzoso et al. |
| 2003/0225022 | A1 | 12/2003 | Taylor et al. |
| 2004/0156826 | A1* | 8/2004 | Dangond et al. .............. 424/93.2 |
| 2006/0287265 | A1* | 12/2006 | Thompson et al. ............. 514/44 |
| 2010/0004314 | A1* | 1/2010 | Dondero et al. ............ 514/44 A |

FOREIGN PATENT DOCUMENTS

| | | |
|---|---|---|
| WO | 94/15596 | 7/1994 |
| WO | 96/25492 | 8/1996 |
| WO | 96/41639 | 12/1996 |
| WO | 99/01551 | 1/1999 |
| WO | 01/02592 | 1/2001 |
| WO | 01/10906 | 2/2001 |
| WO | 03/010286 | 2/2003 |
| WO | 2004/078940 | 9/2004 |
| WO | 2004/113528 | 12/2004 |
| WO | 2005/007853 | 1/2005 |

OTHER PUBLICATIONS

Miyazaki et al, Proteomics 2006, 6:2026-2033.*

Hayashizaki etal., "Analysis of the Mouse Transcriptome Based on Functional Annotation of 60,770 Full-Length cDNAs," Nature, United Kingdom, vol. 420, No. 6915, pp. 563-573, ISSN: 0028-0836, XP002965277, Dec. 5, 2002.
Jin. Bao-Feng et al., "Proteomic analysis of ubiquitin-proteasome effects: insight into the future of eukaryotic initiation factor 5A," Oncogene, Jul. 31, 2003, pp. 4819-4830, vol. 22, No. 31, Nature Publishing Group, XP-002388453, ISSN: 0950-9232.
Annexes to Form PCT/ISA/206, Invitation to Pay Additional Fees, Communication Relating to the Results of the Partial International Search, PC11US20051044266, Aug. 11, 2006, comprised of the Annex first, continuation and 4th of 5 extra sheets and the Patent Family Annex, European Patent Office, International Searching Authority, Rijswijk, NL.
Tome M E et al: "Excess putrescine accumulation inhibits the formation of modified eukaryotic initiation factor 5A (eIF-5A) and induces apoptosis", Biochemical Journal, Portland Press, London, GB, vol. 328, pp. 847-854, 1997, ISSN: 0264-6021.
Database EMBL (Online) Dec. 14, 1999, "uo59b11.y1 NCI_CGAP_Mam1 *Mus musculus* cDNA clone, Image: 26468135' similar to gb:M23419 Initiation Factor 5A (Human);, mRNA sequence", retrieved from EBI accession No. EM_PRO:AW229460.
Bevec Dorian et al: "Molecular characterization of a cDNA encoding functional human deoxyhypusine synthase and chromosomal mapping of the corresponding gene locus", FEBS Letters, vol. 378, No. 2, 1996, pp. 195-198, XP002400480, ISSN: 0014-5793.
Database EMBL (Online) Dec. 11, 1995 "Human deoxyhypusine synthase mRNA, complete cds." retrieved from EBI accession No. EM_HUM:U40579.
Wolff Edith C et al: "Deoxyhypusine synthase from rat testis: Purification and characterization", Journal of Biological Chemistry, vol. 270, No. 15, 1995, pp. 8660-8666, XP002978937, ISSN: 0021-9258.
Joe Young AE et al: "Cloning and expression of human deoxyhypusine synthase cDNA: Structure-function studies with recombinant enzyme and mutant proteins", Journal of Biological Chemistry, vol. 270, No. 38, 1995, pp. 22386-22392, XP002400481, ISSN: 0021-9258.
Database EMBL (Online) Jul. 7, 2000 "hv36b09.x1 NCI_CGAP_Lu24 *Homo sapiens* cDNA clone Image:3175481 3' similar to SW:DHYS_Human P49366 Deoxyhypusine Synthase ;, mRNA sequence." retrieved from EBI accession No. EM_EST:BE218247.
Bartig et al. "The Unique Posttranslational Modification Leading to Deoxyhupusine or Hypusine is a General Feature of teh Archaebacterial Kingdom". (1990) System. Appl. Microbiol., 13, 112-116.
Zhang Xuchen et al.: "Small Interfering RNA Targeting Heme Oxygenase-1 Enhances Ischema-Reperfusion-Induced Lung Apoptosis" Journal of Biological Chemistry, American Society of Biochemical Biologists, Birmingham, US, Vol. 279, No. 11, Mar. 12, 2004, p. 10677-10684, XP002343181 ISSN: 0021-9258; Whole Document.

(Continued)

*Primary Examiner* — Brian Whiteman
*Assistant Examiner* — Mark Halvorson
(74) *Attorney, Agent, or Firm* — Morgan, Lewis & Bockius LLP

(57) ABSTRACT

The present invention relates to the combinatorial use of an siRNA targeted against an endogenous gene to knock out or knock down expression of the endogenous gene in a host and a delivery of a polynucleotide encoding the gene in a delivery vehicle/expression vector to the host to provide expression in the host of the protein encoded by the polynucleotide.
The present invention also relates to a truncated form of eIF-5A1 that is useful for inducing apoptosis and killing of cells, especially cancer cells in a mammal.

20 Claims, 62 Drawing Sheets

OTHER PUBLICATIONS

Ruhl M et al: "Eukaryotic Initiation Factor 5A is a Cellular Target of the Human Immunodeficiency Virus Type 1 Rev Trans-Activation" Journal of Cell Biology, Rockefeller Univeristy Press, New York, US, US, vol. 123, No. 6, Dec. 1, 1993, p. 1309-1320, XP0005751505 ISSN 0021-9525; The Whole Document.

Caraglia M et al.: "The Role of Eukaryotic Initiation Factor 5A in the Control of Cell Proliferation and Apoptosis" Amino Acids, Springer Verlag, AU, Vol. 20, No. 2, 2001, p. 91-104, XP002291822, ISSN: 0939-4451; The Whole Document.

Zhang Xuchen et al.: "Small Interfering RNA Targeting Heme Oxygenase-1 Enhances Ischema-Reperfusion-Induced Lung Apoptosis" Journal of Biological Chemistry, American Society of Biochemical Biologists, Birmingham, US, vol. 279, No. 11, Mar. 12, 2003, pp. 10677-10684, XP002343181 ISSN: 0021-9258; Whole Document CI.

International Search Report of PCT/U520051025766, Mar. 10, 2006.

Heijstek et al. "Mouse Models of Colorectal Cancer and Liver Metastases". (Digestive Surgery 22: 16-25, 2005).

Herweijer et al. "Progress and Prospects: naked DNA gene transfer and therapy". (Gene Therapy, 10: 453-458, 2003).

Siuciak et al. "Behavioral and neurochemical characterization of mice deficient in teh phosphodiesterase-4B (PDE4B) enzyme". (Psychopharmacology 197: 115-126, 2008).

Linder et al, "Genetic Variables that Influence Phenotype". (ILAR Journal, 47(2): 132-40, 2006).

Ma et al Inhibition of Metastasis of Intraocular Melanomas by Adenovirus-Mediated Gene Transfer of Plasminogen Activator inhibitor Type 1 (PAI-1) in an Athymic Mouse Model:. (Blood, 90(7): 2738-46, 1997).

Caraglia et al. "Modulation of molecular mechanisms involved in protein synthesis machinery as a new tool for the control of cell proliferation". (EurJ Biochem. 267: 3919-3936 (2000).

Provost et al. (2002) Ribonuclease Activity and RNA Binding of Recombinant Human Dicer, EMBO J. 21(21): 5864-5874.

Tabara et al. (2002) The dsRNA Binding Protein RDE-4 Interacts with RDE-1, DCR-1 and a DexH-box Helicase to Direct RNAi in *C. elegans*, Cell 109(7):861-71.

Ketting et al. (2002) Dicer Functions in RNA Interference and in Synthesis of Small RNA Involved in Developmental Timing in *C. elegans*.

Martinez et al., Single-Stranded Antisense siRNAs Guide Target RNA Cleavage in RNAi, Cell 110(5):563.

Hutvagner & Zamore (2002) A microRNA in a multiple-turnover RNAi enzyme complex, Science 297:2056.

Sharp, RNA interference-2001, Genes Dev. 2001, 15:485.

Bernstein, Caudy, Hammond, & Hannon (2001) Role for a bidentate ribonuclease in the initiation step of RNA interference, Nature 409:363.

Nykanen, Haley, & Zamore (2001), ATP requirements and small interfering RNA structure in the RNA interference pathway, Cell 107:309.

Elbashir, Lendeckel, & Tuschl (2001) RNA interference is mediated by 21- and 22-nucleotide RNAs, Genes Dev. 15:188.

Kisielow, M. et al. (2002), Isoform-specific knockdown and expression of adaptor protein ShcA using small interfering RNA, J. Biochem. 363:1-5.

Fire, A. et al. "Potent and specific genetic interference by double-stranded RNA in *Caenorhabditis elegans*". (1998) Nature 391:806-811.

Shirai et al. "Global Analysis of Gel Mobility of Proteins and Its Use in Target Identification". Journal of Biological Chemistry; vol. 283. No. 16. pp. 10745-10752; Apr. 18, 2008.

Luo, Dan, et al., "Synthetic DNA delivery systems". Nature Biotechnology, vol. 18, Jan. 2000, pp. 33-37.

Hortobagyi, Gabriel N., et al. "Cationic Liposome-Mediated E1A Gene Transfer to Human Breast and Ovarian Cancer Cells and Its Biologic Effects: A Phase I Clinical Trail". J. Clinical Oncology, vol. 19, Issue 14 Jul. 2001:3422-3433.

Yu, Wei, et al. "Enhanced transfection efficiency of a systemically delivered tumor-targeting immunolipoplex by inclusion of a pH-sensitive histidylated oligolysine peptide". Nucleic Acids Research. 2004, 32(5);e48.

Marjoros, Istvan, J., et al, "PAMAM Dendrimer-Based Multifunctional Conjugate for Cancer Therapy: Synthesis, Characterization, and Functionality," Biomacromolecules, vol. 7, No. 2, 2006; 572-579.

Majoros, Istvan J., et al. "Poly(amidoamine) Dendrimer-Based Multifunctional Engineered Nanodevice for Cancer Therapy". J. Med. Chem, 2005. 48, 5892-5899.

Ohana et al., "Regulatory sequences of the H19 gene in DNA based therapy of bladder cancer". 2004. Gene Ther Mol Bio 8:181-192.

Vernejoul et al., "Antitumor Effect of in Vivo Somatostatin Receptor Subtype 2 Gene Transfer in Primary and Metastatic Pancreatic Cancer Models". 2002. Cancer Research 62:6124-31.

Urbain-Klein et al., "RNAi-mediated gene-targeting through systemic application of polyethylenimine (PEI)-complexed siRNA in vivo". 2004. Gene therapy 23:1-6.

Grezelinski et al. "RNA Interference-Mediated Gene Silencing of Pleiotrophin Through Polyethylenimine-Complexed Small Interfering RNAs in Vivo Exerts Antitumoral Effects in Glioblastoma Xenografts" 2006. Human Gene Therapy 17:751-66.

Garzon et al. "Induction of gp 120-specific protective immune responses by genetic vaccination with linear polyethylenimine-plasmid complex". 2005. Vaccine 23:1384-92.

Lemkine et al. "Preferential Transfection fo Adult Mouse Neural Stem Cells and Theuir Immediate Progeny in Vivo with Polyethylebnimine". 2002. Mol. Cell. Neurosci. 19:165-174.

Liu & Tartakoff (1997) Supplement to Molecular Biology of the Cell, 8, 426a. Abstract No. 2476, 37th American Society for Cell Biology Annual Meeting.

Rosorius et al. "Nuclear pore localization and nucleocytoplasmic trasport of eIF-5A: evidence for direct interaction with the export receptor CRM1". (1999) J. Cell Science, 112, 2369-2380.

Park "The Identification of an Eukaryotic Initiation Factor 4D Precursor in Spermidine-depleted Chinese Hamster Ovary Cells". (1988) J. Biol. Chem., 263, 7447-7449.

Schumann & Klink: "Archaebacterial Protein Contains Hypusine, a Unique Amino Acid Characteristic for Eukaryotic Translation Initiation Factor 4D". (1989) System. Appl. Microbiol., 11, 103-107.

Gordon et al. "Eukaryotic Initiation Factor 4D, the Hypusine-containing Protein, is Conserved among Eukaryotes". (1987a) J. Biol. Chem., 262, 16585-16589.

Park et al. "Hypusine: its post-translational formation in eukaryotic initiation factor 5A and its potential role in cellular regulation". (1993) Biofactors, 4, 95-104.

Schnier et al. "Translation Initiation Factor 5A and Its Hypusine Modification Are Essential for Cell Viability in the Yeast *Saccharomyces cerevisiae*". (1991) Mol. Cell. Biol., 11, 3105-3114.

Sasaki et al. "Deoxyhupusine synthase gene is essential for cell viability in the yeast *Saccharomyces cerevisiae*". (1996) FEBS Lett., 384, 151-154.

Park et al. (1998) J. Biol. Chem., 273, 1677-1683.

Kang et al. (1993), "Effect of initiation factor eIF-5A depletion on cell proliferation and protein synthesis," in Tuite, M. (ed.), Protein Synthesis and Targeting in Yeast, NATO Series H.

Xu & Chen (2001) "Hypusine is Required for a Sequence-specific Interaction of Eukaryotic Initiation Factor 5A with Postsystematic Evolution of Ligands by Exponential Enrichment RNA". J. Biol. Chem., 276, 2555-2561.

Chauhan et al. "Multiple Myeloma Cell Adhesion-Induced Interleukin-6 Expression in Bone Marrow Stromal Cells Involves Activation of Nf-kB" (1996) Blood 87, 1104.

Hideshima et al. "The role of tumor necrosis factor alpha in the pathophysiology of human multiple myeloma: therapeutic applications". (2001) Oncogene 20,4519.

Hideshima et al. "NF-kB as a Therapeutic Target in Multiple Myeloma". (2002) JBC 277, 16639.

Malone et al. 2006. B29 gene silencing in pituitary cells is regulated by its 3' enhancer. J. Mol. Biol. 362: 173-183.

Komatsu et al. 2002. Novel regulatory regions found downstream of the rat B29/Ig-b gene. Eur. J. Biochem. 269: 1227-1236.

Chay KO, Park SS, Mushinski JF (2002). Linkage of caspase-mediated degradation of paxillin to apoptosis in Ba/F3 murine pro-B lymphocytes. J Biol Chem. 277, 14521-14529.

Fischer U, Janicke RU, Schulze-Osthoff K (2003). Many cuts to ruin: a comprehensive update of caspase substrates. Cell Death and Differentiation 10, 76-100.

Kim, S. C., Sprung, R., Chen, Y., Xu, Y., Ball, H., Pei, J., Cheng, T., Kho, Y., Xiao, H., Xiao, L., Grishin, N. V., White, M., Yang, X. J., and Zhao, Y. (2006) Substrate and Functional Diversity of Lysine Acetylation Revealed by a Proteomics Survey. Mol Cell 23, 607-618.

Shirai et al. (2008). Global analysis of gel mobility of proteins and its use in target identification J. Biol. Chem. 283, 10745-10752.

Chen, K.Y. et al, "RNA Interference Analysis of the Function of Hypusine-Containing Eukaryotic Initiation Factor 5A in *C. elegans*,"FASEB Journal (Federation of American Societies for Experimental Biology), Mar. 20, 2002, p. A162, vol. 16, No. 4, XP008033807, ISSN: 0892-6638, Bethesda, US.

Crooke, S. (2004) Progress in Antisense Technology. Annu. Rev. Med. v 44: 61-95.

Database EMBL (online) Jul. 7, 2000 "hv36b09.x1 NCI_CGAP_Lu24 *Homo sapiens* cDNA clone Image: 3175481 3 prime similar to SW: DHYS_Human P49366 Deoxyhypusine Synthase:, mRNA sequence." retrieved from EBI accession No. EM_EST:BE218247.

Database EMBL: (online) Dec. 14, 1999, uo59b11.y1 NCI_CGAP_Mam1 *Mus musculus* cDNA clone, INAGE: 2646813 5 prime similar to gb: M23419 Initiation factor 5A (Human); mRNA sequence, retrieved from EBI accession No. EM_PRO: AW229460.

Hazeki, et al. (2007) Role of Phosphoinositide 3-Kinase in Innate Immunity. Biol. Pham. Bull., v. 30(9): 1617-1623.

Jen et al. "Supression of Gene Expression by Targeted Disruption of Messenger RNA: Available Options and Current Strategies" (Stem Cells 2000, vol. 18, p. 307-319).

Kalota, et al: Progress in the Development of nucleic Acid Therapeutics. Handbook of Experimental Pharmacology, V. 176, pp. 173-196 (2006).

Opalinska et al. "Nucleic-Acid Therapeutics: Basic Principles and Recent Applications" (Nature Reviews Drug Discovery, 2002, volt, p. 503-514.

Smit-McBride, et al. Sequence Determination and cDNA Cloning of Eukaryotic Initiation Factor 4D, the Hypusine-containing containing Protein. J. Biol. Chem. v 264(3): 1578-1583. (1989).

Taylor, et al., Antisense Oligonucleotides: a Systematic high-Throughput Approach to Target Validation and Gene Functions Determination, Drug Discovery Today, v. 4: 562-567 (1999).

Vickers, et al. (2003) Efficient Reduction of Target RNAs by Small Interfering RNA and RNASE H-Dependent Antisense Agents. J. Biol. Chem., v. 278(9): 7108-18.

Eck et al, Goodman & Gilman's the Pharmacolotgical basis of Therapeutics, McGraw-Hill, New York, NY. pp. 77-101.

Hunt et al, "Hurdles and Hopes for Cancer Treatment". (Science, 297: 415-416, 2002).

Thomas et al, "Progress and Problems with the Use of Viral Vectors for Gene Therapy". (Nature, 4: 346-358, 2003).

Rubanyi et al. "The future of human gene therapy". (Molecular Aspects of Medine, 2001, 22, 113-142).

Vieyra et al, "Proapoptotic role of novel gene-expression factors" (Clin Transl Oncol, 9: 355-363, 2007).

Li et al, "A Novel eIF5A Complex Functions as a Regulator of p53 and p53-dependent Apoptosis". (JBC, 279: 49251-49258, 2004).

Taylor et al, p 446; "Eukaryotic translation initiation factor 5A induces apoptosis in colon cancer cells and associates with the nucleus in response to tumour necrosis factor alpha signalling". Experimental Cell research 313: 437-449, (2007).

Voskoglou-Nomikos et at "Clinical Predictive Value of the in Vitro Cell Line, Human Xenograft, and Mouse Allograft Preclinical Cancer Models". (Clinical Cancer Research, 2003, 9, 4227-4239).

Kelland et al. ""Of mice and Men": values and liabilities of the athymic nude mouse model in anticancer drug development". (European Journal of Cancer, 2004, 40, 827-836).

Kerbel et al. Models of Anti-Cancer Therapy: Human Tumor Xenografts as Predictive Preclinical Models for Anticancer Drug Activity in Humans; Better Than Commonly Perceived—But They Can Be Improved (Cancer Biology & therapy 2:4 Suppl. 1, S134-139).

Soh et al. "Thyroid-stimulating hormone promotes the secretion of vascular endothelial growth factor in thyroid cancer cell lines". (Surgery, 129(6): 944-7, 1996).

Terman et al. "VEGF and Tumor Angiogenesis". Einstein Quart. J. Biol. and Med, 2001, 18: 59-66.

Nigro et al. "Mutations in the p53 gene occur in diverse human tumour types". Nature, 342: 705-708 (1989).

* cited by examiner

Amino Acid Sequence of Human eIF5A1

```
                                                                    Hypusination site
                                         acetylation site  K47 K50
              51
pHM6 - eIF5A1 #2  MADDLDFETG DAGASATFPM QCSALRKNGF VVLKGRPCKI VEMSTSKTGK
       genbank    MADDLDFETG DAGASATFPM QCSALRKNGF VVLKGRPCKI VEMSTSKTGK
       Consensus  MADDLDFETG DAGASATFPM QCSALRKNGF VVLKGRPCKI VEMSTSKTGK
                                   UQ
                                   K67
                                   PKC
              51                                                    100
            # HGHAKVHLVG IDIFTGKKYE DICPSTHNMD VPNIKRNDFQ LIGIQDGYLS
      genbank HGHAKVHLVG IDIFTGKKYE DICPSTHNMD VPNIKRNDFQ LIGIQDGYLS
    Consensus HGHAKVHLVG IDIFTGKKYE DICPSTHNMD VPNIKRNDFQ LIGIQDGYLS 101                                                   150
            # LLQDSGEVRE DLRLPEGDLG KEIEQKYDCG EEILITVLSA MTEEAAVAIK
      genbank LLQDSGEVRE DLRLPEGDLG KEIEQKYDCG EEILITVLSA MTEEAAVAIK
    Consensus LLQDSGEVRE DLRLPEGDLG KEIEQKYDCG EEILITVLSA MTEEAAVAIK 151
            # AMAK
      genbank AMAK
    Consensus AMAK
```

PKC = putative protein kinase C phosphorylation site
UQ = putative ubiquitination site (K67)
K47 = confirmed acetylation site
K50 = confirmed hypusination site
pHM6-eIF5A1 #2 = predicted amino acid sequence of human eIF5A1 in pHM6 vector
Genbank = amino acid sequence of human eIF5A1 (ACCESSION # NP_001961)

FIG. 1

Mutation of eIF5A1 at K50 and K67 increases
accumulation of transfected protein.

Mutation of eIF5A1 at K50 and K67 increases
accumulation of transfected protein.

Mutation of eIF5A1 at K47, K50 and K67 increases accumulation of transfected protein.

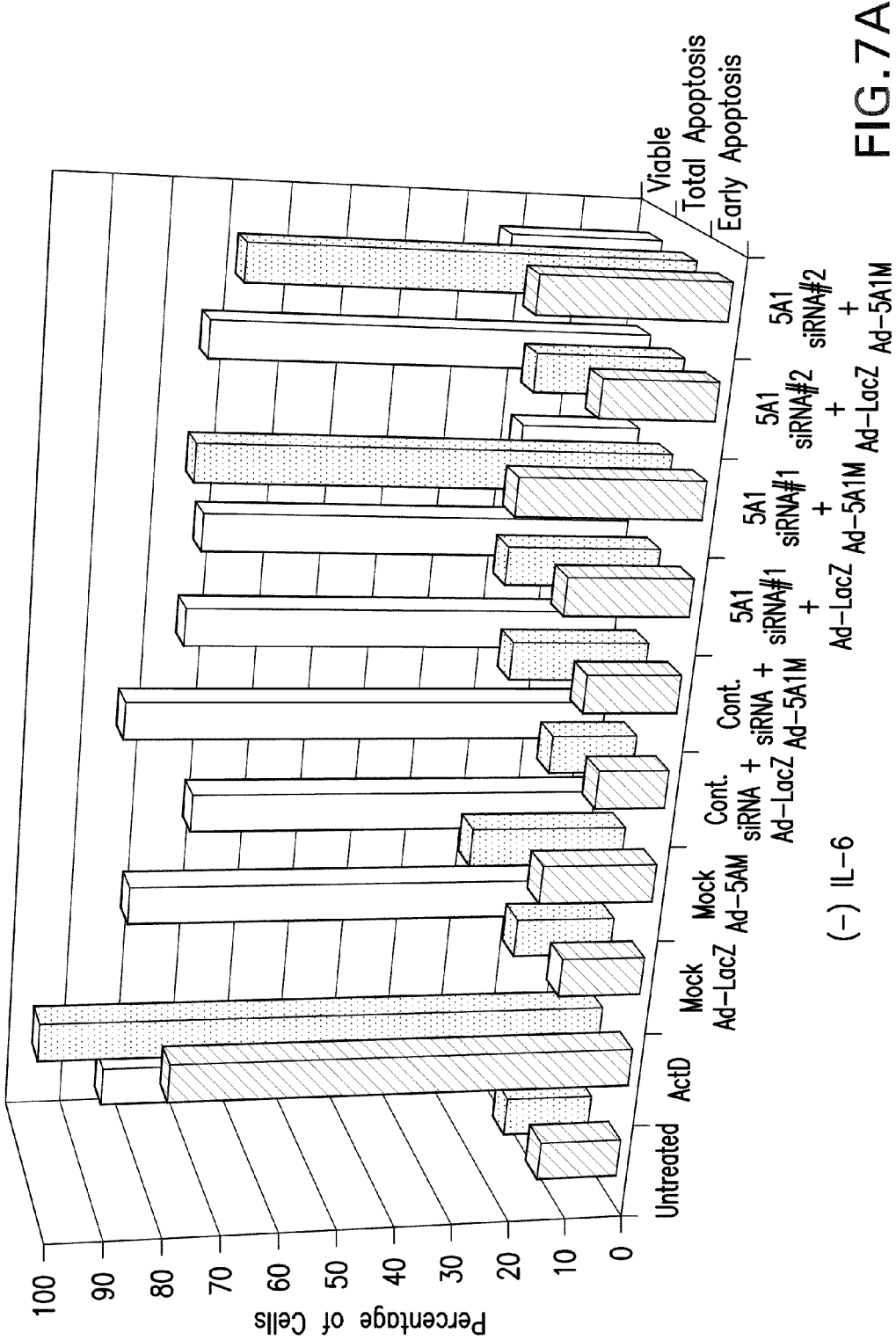

Pre-treatment with eIF5A1 siRNA #1 reduces expression of endogenous eIF5A1 but allows accumulation of RNAi-resistant eIF5A1$^{k50A}$ expressed by adenovirus Pre-treatment with eIF5A1 siRNA #1 prior to Adenovirus infection reduces expression of phosphorylated NF-kB in human multiple myeloma cells Pre-treatment with eIF5A1 siRNA #1 prior to Adenovirus infection reduces expression of phosphorylated NF-kB and ICAM-1 in human multiple myeloma cells siRNA-mediated suppression of eIF5A in human multiple myeloma Cells inhibits LPS-mediated induction of NFkB DNA-Binding Activity Administration of eIF5A1 siRNA intra-venously (i.v.) and PEI/eIF5A1K50R plasmid complexes intra-tumorally (i.t.) results in delay of growth of multiple myeloma subcutaneous tumors and tumor shrinkage (Group 2B).

Administration of eIF5A1 siRNA intra-venously (i.v.) and PEI/eIF5A1$^{K50R}$ plasmid complexes intra-tumorally (i.t.) results in tumor shrinkage of multiple myeloma subcutaneous tumors (Group 2B). There was no evidence of tumor growth in one mouse of the treatment group (group 2B).

Intra-venous co-administration of eIF5A1 plasmid and eIF5A1 siRNA delays growth of multiple myeloma subcutaneous tumors (Group 3B).

Co-administration of eIF5A1 plasmid and eIF5A1 siRNA delays growth of multiple myeloma subcutaneous tumors and results in tumor shrinkage (Group A).

Co-administration of eIF5A1 plasmid and eIF5A1 siRNA delays growth of multiple myeloma subcutaneous tumors and results in tumor shrinkage (Group A).

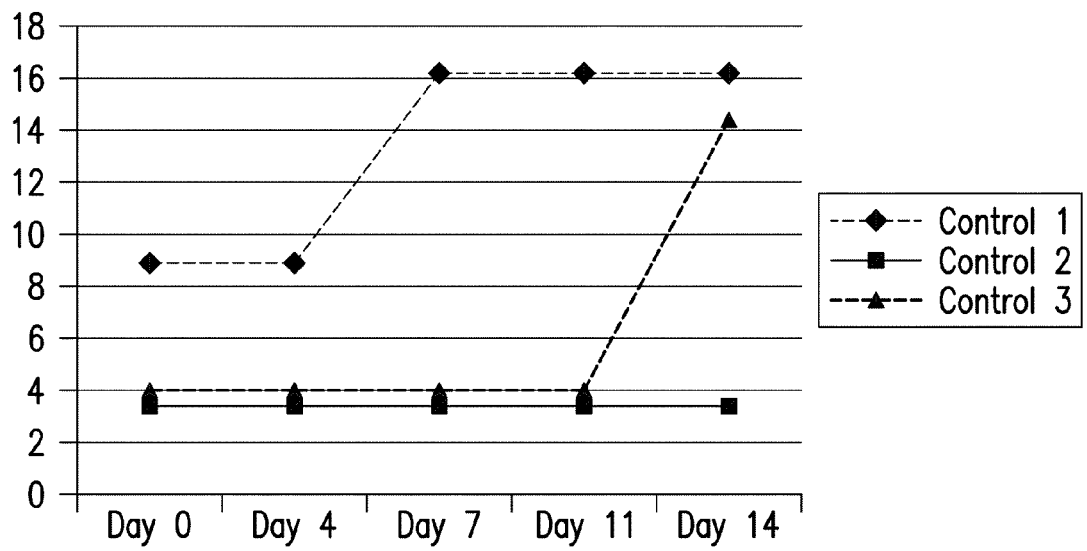

Administration of eIF5A1 siRNA intra-venously (i.v.) and PEI/eIF5A1$^{K50R}$ plasmid complexes intra-tumourally (i.t.) results in tumor shrinkage of multiple myeloma subcutaneous tumors (Group B).

FIG.18A

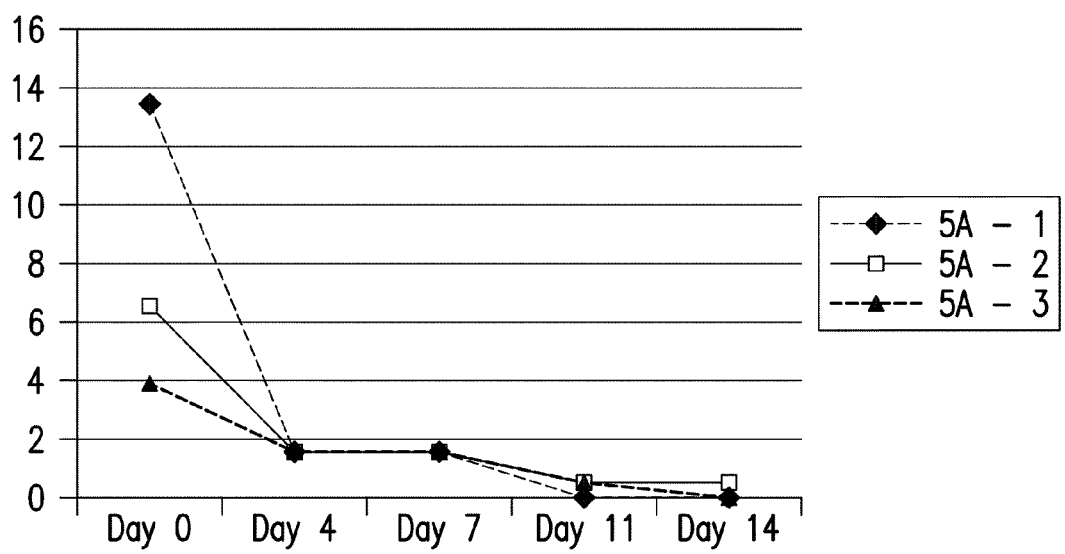

Administration of eIF5A1 siRNA intra-venously (i.v.) and PEI/eIF5A1$^{K50R}$ plasmid complexes intra-tumourally (i.t.) results in tumor shrinkage of multiple myeloma subcutaneous tumors (Group B).

FIG.18B

Co-administration of eIF5A1K50R plasmid, driven by either the EF1 or B29 promoter, and eIF5A1 siRNA delays growth of multiple myeloma subcutaneous tumors and results in tumor shrinkage (KAS-SQ-5).

Co-administration of eIF5A1 siRNA increases anti-tumor effect of eIF5A1$^{K50R}$ plasmid, driven by either the EF1 or B29 promoter, on multiple myeloma subcutaneous tumors and results in reduced tumor burden (KAS-SQ-5).

eIF5A1 siRNA Synergistically Increases Apoptosis Induction
Resulting from Infection with Ad-eIF5A in Lung Adenocarcinoma Cells Predicted Sequence of pExp5A (3371 bp)

Single-cutting Restriction Enzyme sites are highlighted
EcoRI = GAATTC; XhoI = CTCGAG; ClaI = ATCGAT ; SpeI = ACTAGT;
HindIII = AAGCTT; NcoI = CCATGG; NheI = GCTAGC;   MluI = ACGCGT

```
TTAATTAAAATTATCTCTAAGGCATGTGAACTGGCTGTCTTGGTTTTCATCTGT
ACTTCATCTGCTACCTCTGTGACCTGAAACATATTTATAATTCCATTAAGCTGT    βGlo
GCATATGATAGATTTATCATATGTATTTTCCTTAAAGGATTTTTGTAAGAACTA    MAR
ATTGAATTGATACCTGTAAAGTCTTTATCACACTACCCAATAAATAATAAATCT
CTTTGTTCAGCTCTCTGTTTCTATAAATATGTACAAGTTTTATTGTTTTTAGTG
GTAGTGATTTTATTCTCTTTCTATATATATACACACATGTGTGCATTCATAA
ATATATACAATTTTTATGAATAAAAAATTATTAGCAATCAATATTGAAAACCAC
TGATTTTTGTTTATGTGAGCAAACAGCAGATTAAAAGGAATTGTCGAGTCATCG
ATACTAGTGCGACCGCCAAACCTTAGCGGCCCAGCTGACAAAAGCCTGCCCTCC    B29
CCCAGGGTCCCCGGAGAGCTGGTGCCTCCCCTGGGTCCCAATTTGCATGGCAGG    promoter
AAGGGGCCTGGTGAGGAAGAGGCGGGGAGGGGACAGGCTGCAGCCGGTGCAGTT    EM2K
ACACGTTTTCCTCCAAGGAGCCTCGGACGTTGTCAAGCTTCTGCCTTCTCCCTC
CTGTGAGTTTGGTAAGTCACTGACTGTCTATGCCTGGGAAAGGGTGGGCAGGAG    I 140
ATGGGGCAGTGCAGGAAAAGTGGCACTATGAACCCTGCAGCCCTAGGAATGCAT
CTAGACAATTGTACTAACCTTCTTCTCTTTCCTCTCCTGACAGGTTGGTGTACA
GTAGCTTCCACCATGGCAGATGATTTGGACTTCGAGACAGGAGATGCAGGGGCC    EM2K
TCAGCCACCTTCCCAATGCAGTCCTCAGCATTACGTAAGAATGGTTTTGTGGTG    Zeocin
CTCAAGGGCCGGCCATGTAAGATCGTCGAGATGTCTACTTCCAAGACTGCCAGG
CATGGCCATGCCAACGTCCATCTGGTTGGTATTGATATTTTTACTGGGAAGAAA
TATGAAGATATCTGCCCGTCGACTCATAACATGGATGTCCCCAACATCAAAAGG
AATGATTTCCAGCTGATTGGCATCCAGGATGGGTACCTATCCCTGCTCCAGGAC    eIF5A1^{K50R}
AGTGGGCAGGTACCAGAGGACCTTCGTCTGCCTGAGGGAGACCTTGGCAACGAG
ATTGAGCAGAAGTATGACTGTGGAGAAGAGATCCTGATCACAGTGCTCTCCGCC
ATGACAGAGGAGGCAGCTGTTGCAATCAAGGCGATGGCAAAATAACTGGCTAGC
TGGCCAGACATGATAAGATACATTGATGAGTTTGGACAAACCACAACTAGAATG    SV40
CAGTGAAAAAAATGCTTTATTTGTGAAATTTGTGATGCTATTGCTTTATTTGTA    pAn
ACCATTATAAGCTGCAATAAACAAGTTAACAACAACAATTGCATTCATTTTATG
TTTCAGGTTCAGGGGGAGGTGTGGGAGGTTTTTTAAAGCAAGTAAAACCTCTAC
```

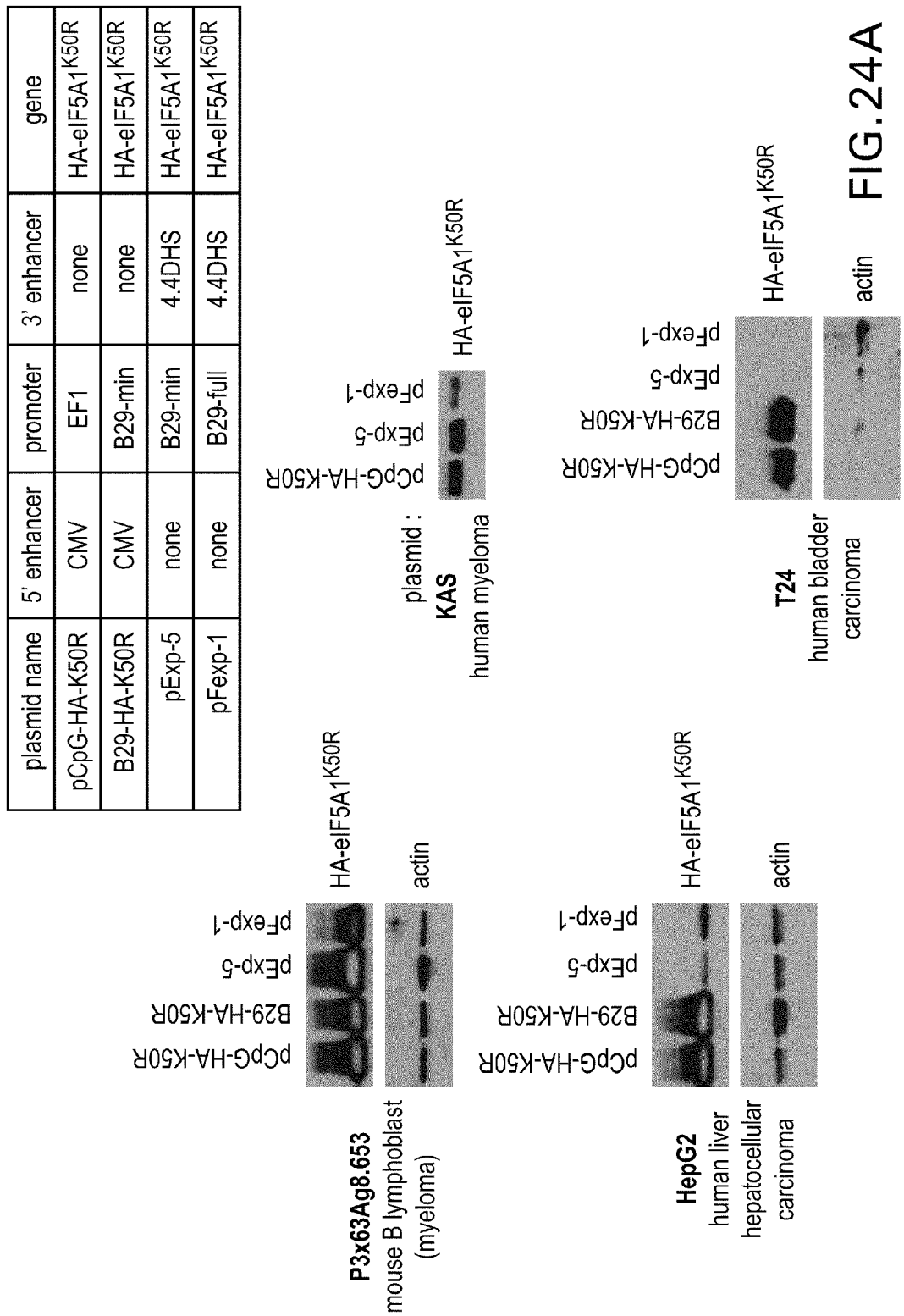

h5A1siRNA

Target sequence : 5' GCU GGA CUC CUC CUA CAC A (dTdT) 3' siRNA

5' GCU GGA CUC CUC CUA CAC A dTdT 3'
3' dTdT CGA CCU GAG GAG GAU GUGU 5'

FIG.25

Sequence of eIF5A1$^{K50R}$ cDNA

Nucleotide:

Start codon: <u>ATG</u>
Stop codon: <u>TAA</u>
HA-tag: <u>ATGTACCCATACGACGTCCCAGACTACGCT</u>

ATAGGGAGACCCAAGCTGGAGACC<u>ATG</u>TACCCATACGACGTCCCAGACTACG
CTGGAAGCTTA<u>ATG</u>GCAGATGATTTGGACTTCGAGACAGGAGATGCAGGGGC
CTCAGCCACCTTCCCAATGCAGTGCTCAGCATTACGTAAGAATGGTTTTGTG
GTGCTCAAGGGCCGGCCATGTAAGATCGTCGAGATGTCTACTTCGAAGACTG
GCAGGCATGGCCATGCCAAGGTCCATCTGGTTGGTATTGATATTTTTACTGG
GAAGAAATATGAAGATATCTGCCCGTCGACTCATAACATGGATGTCCCCAAC
ATCAAAAGGAATGATTTCCAGCTGATTGGCATCCAGGATGGGTACCTATCCC
TGCTCCAGGACAGTGGGGAGGTACGAGAGGACCTTCGTCTGCCTGAGGGAGA
CCTTGGCAAGGAGATTGAGCAGAAGTATGACTGTGGAGAAGAGATCCTGATC
ACAGTGCTGTCCGCCATGACAGAGGAGGCAGCTGTTGCAATCAAGGCCATGG
CAAAA<u>TAA</u>CTGGAATTC

Protein:
    HA
MYPYDVPDYAGSLMADDLDFETGDAGASATFPMQCSALRKNGFVVLKGRPCK
IVEMSTSKTGRHGHAKVHLVGIDIFTGKKYEDICPSTHNMDVPNIKRNDFQL
IGIQDGYLSLLQDSGEVREDLRLPEGDLGKEIEQKYDCGEEILITVLSAMTE
EAAVAIKAMAK

FIG. 28

Alignment between human eIF5A1 and human eIF5A1$^{K50R}$

```
              1                                                          50
    eIF5A1  MADDLDFETG DAGASATFPM QCSALRKNGF VVLKGRPCKI VEMSTSKTGK
      K50R  MADDLDFETG DAGASATFPM QCSALRKNGF VVLKGRPCKI VEMSTSKTGR
 Consensus  MADDLDFETG DAGASATFPM QCSALRKNGF VVLKGRPCKI VEMSTSKTGr 51                                                        100
    eIF5A1  HGHAKVHLVG IDIFTGKKYE DICPSTHNMD VPNIKRNDFQ LIGIQDGYLS
      K50R  HGHAKVHLVG IDIFTGKKYE DICPSTHNMD VPNIKRNDFQ LIGIQDGYLS
 Consensus  HGHAKVHLVG IDIFTGKKYE DICPSTHNMD VPNIKRNDFQ LIGIQDGYLS 101                                                       150
    eIF5A1  LLQDSGEVRE DLRLPEGDLG KEIEQKYDCG EEILITVLSA MTEEAAVAIK
      K50R  LLQDSGEVRE DLRLPEGDLG KEIEQKYDCG EEILITVLSA MTEEAAVAIK
 Consensus  LLQDSGEVRE DLRLPEGDLG KEIEQKYDCG EEILITVLSA MTEEAAVAIK 151
    eIF5A1  AMAK
      K50R  AMAK
 Consensus  AMAK
```

FIG. 29

DNA : siRNA ratio

1:0  4:1  3:1  2:1  1:1  1:2  1:3  1:4  0:1

HA-eIF5A$^{K50R}$
(α-HA-HRP)

— 26 kDa
— 17 kDa

PEI Nanoparticles (N/P = 6)
1:0 = 3 μg B29-HA-eIF5A$^{K50R}$
4:1 = 2.4 μg B29-HA-eIF5A$^{K50R}$ + 0.6 μg h5A1
3:1 = 2.25 μg B29-HA-eIF5A$^{K50R}$ + 0.75 μg h5A1
2:1 = 2 μg B29-HA-eIF5A$^{K50R}$ + 1 μg h5A1
1:1 = 1.5 μg B29-HA-eIF5A$^{K50R}$ + 1.5 μg h5A1
1:2 = 1 μg B29-HA-eIF5A$^{K50R}$ + 2 μg h5A1
1:3 = 0.75 μg B29-HA-eIF5A$^{K50R}$ + 2.25 μg h5A1
1:4 = 0.6 μg B29-HA-eIF5A$^{K50R}$ + 2.4 μg h5A1
0:1 = 3 μg h5A1

B29-HA-eIF5A$^{K50R}$ : plasmid DNA B-cell specific promoter/enhancer (B29) in pCpG vector (same vector as pExp5A) expressing HA-tagged eIF5A$^{K50R}$ h5A1 : siRNA targeting human eIF5A (GLP-grade)

PEI : GLP-grade

Effect of DNA:siRNA ratio on HA-eIF5A$^{K50R}$ Expression

FIG. 30

Apoptosis Assay: Effect of DNA:siRNA ratio on apoptosis induced by nanoparticle transfection.

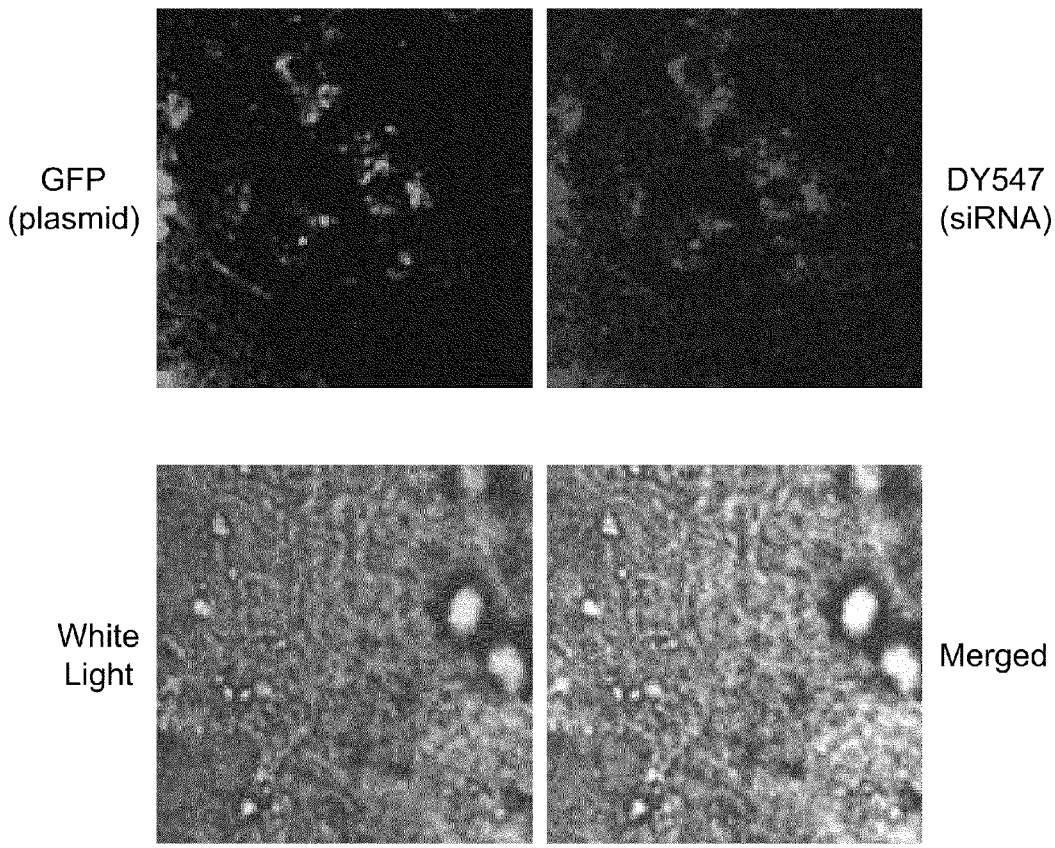

Tumour section 48 hours after injection with nanoparticles containing pExp-GFP (GFP under control of B-cell-specific promoter) and DY547-siRNA (fluorescently-labelled siRNA). Co-localized expression of GFP and DY547 is observed in tumour section following confocal microscopy indicating that the nanoparticles are being effectively taken up by tumour tissue and that nanoparticles are delivering plasmid and siRNA to the same cell.

FIG.33

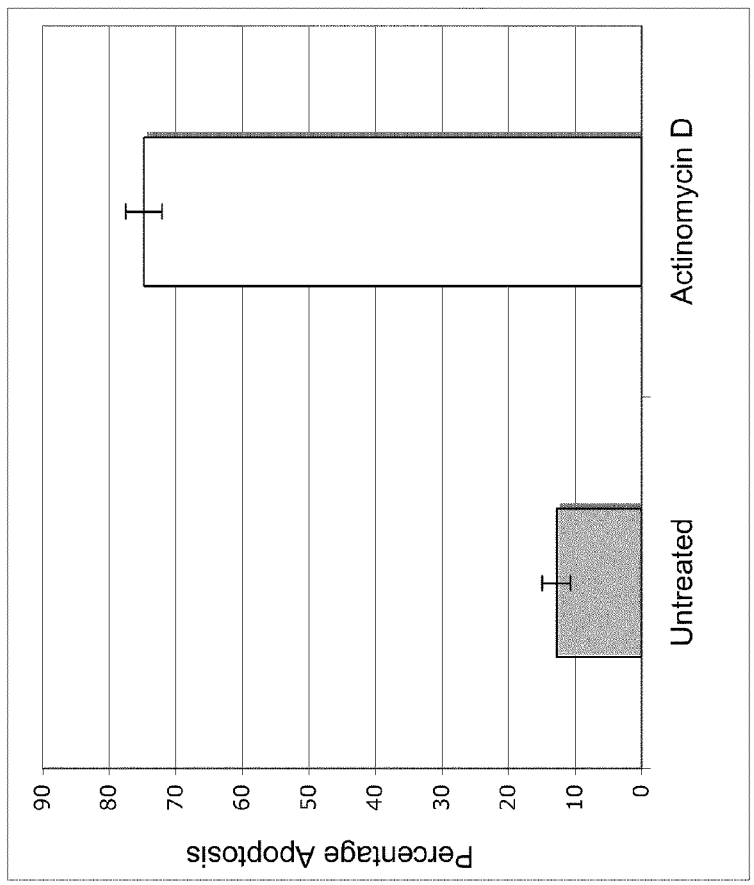
Figure 34: KAS Cells Undergo Apoptosis in Response to Actinomycin D
KAS cells were either left untreated or were treated with 0.5 μg/ml Actinomycin D. Twenty-four hours after the intiation of treatment, the cells were harvested, washed, and apoptotic cells were labelled using Annexin/PI (BD Bioscience) and analyzed by flow cytometry.

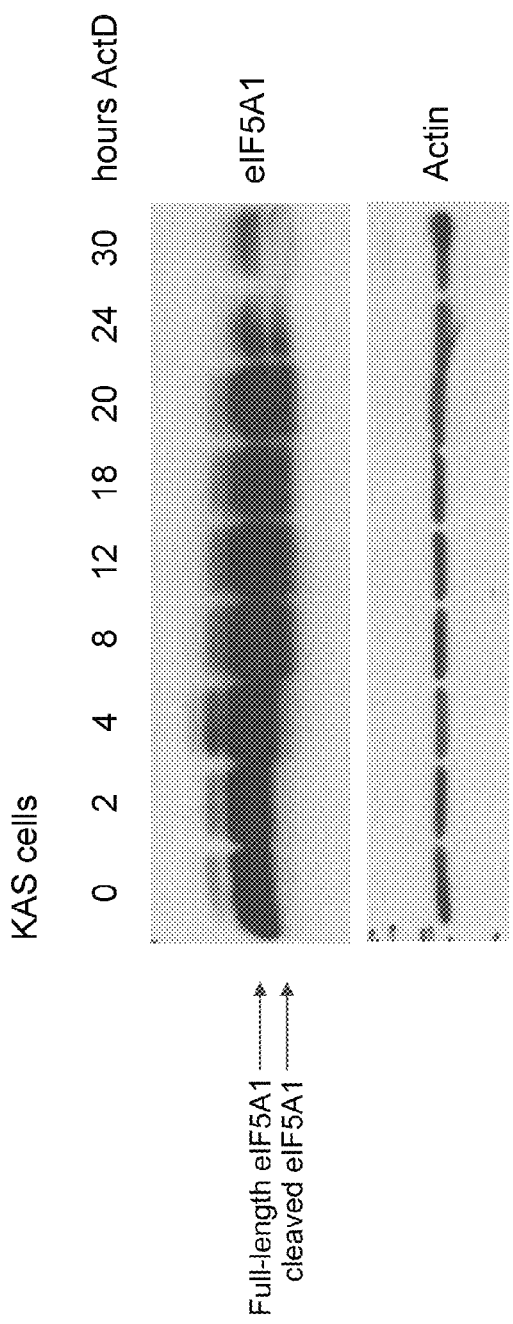

Figure 35: A Cleaved form of eIF5A1 Accumulates in Response to Actinomycin D Treatment
KAS cells were treated with 0.5 μg/ml Actinomycin D for time periods ranging from 0 hours to 30 hours. Cell lysate was harvested and analyzed by Western blot using an antibody against eIF5A1. Accumulation of a smaller molecular weight (cleaved) form of eIF5A1 was observed beginning at approximately 8 hours after Actinomycin D treatment and was present throughout the remainder of the treatment. Equal loading is demonstrated by Western blot of the same membrane using an antibody against actin.

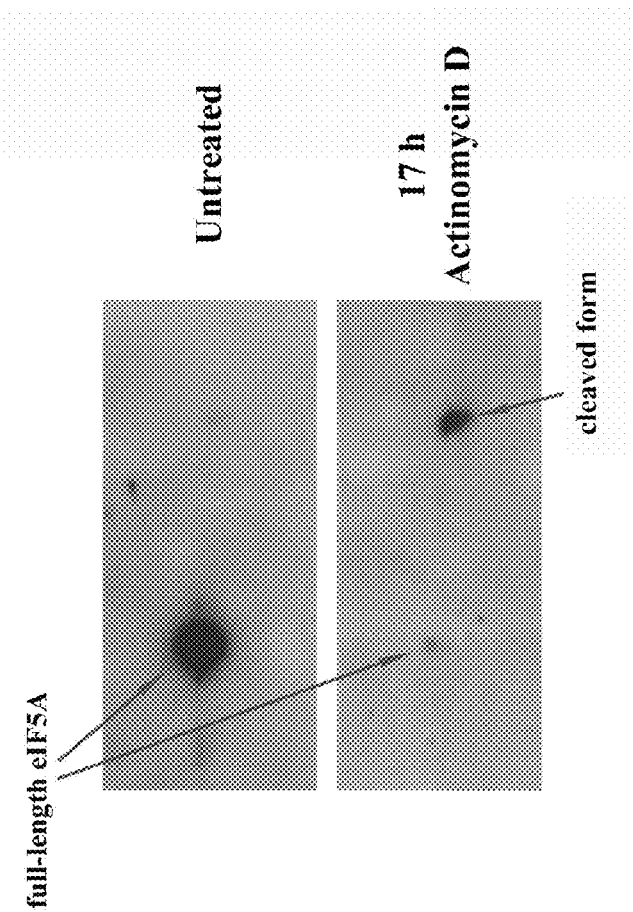

Figure 36: A Cleaved form of eIF5A1 with a Higher Isoelectric Point Accumulates in Response to Actinomycin D Treatment KAS cells were either left untreated or were treated with 0.5 µg/ml Actinomycin D. Seventeen hours after the intiation of treatment, the cell lysates were harvested and separated by 2-D gel electrophoresis followed by Western blot analysis using an antibody against eIF5A1. A large amount of the full-length eIF5A1 can be observed in the untreated sample while accumulation of a cleaved form of eIF5A1 with a higher pI can be observed in the Actinomycin D-treated sample.

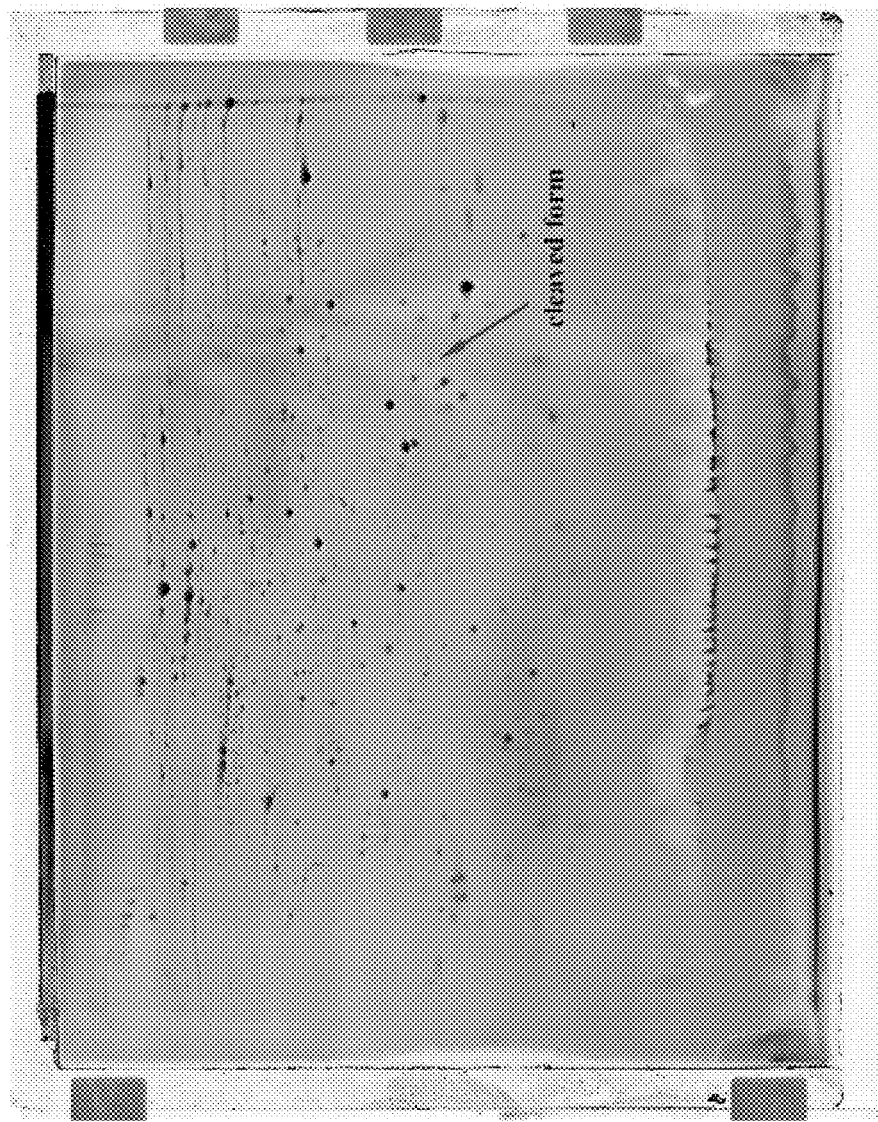

Figure 37: Isolation of the Cleaved Form of eIF5A1 by 2-D Gel Electrophoresis
KAS cells were treated with 0.5 µg/ml Actinomycin D. Seventeen hours after the intiation of treatment, the cell lysate was harvested and separated by 2-D gel electrophoresis followed by Coomassie Blue staining. The position of the cleaved form of eIF5A1 that was collected for mass spectrometry analysis is indicated.

A) Full length eIF5A1:

predicted mol. Wt.: 16.83 kDa
predicted pI: 5.07

1 MADDLDFETG DAGASATFPM QCSALRKNGF VVLKGRPCKI VEMSTSKTGK
   51 HGHAKVHLVG IDIFTGKKYE DICPSTHNMD VPNIKRNDFQ LIGIQDGYLS
  101 LLQDSGEVRE DLRLPEGDLG KEIEQKYDCG EEILITVLSA MTEEAAVAIK
  151 AMAK (SEQ ID NO:35)

B) Predicted Caspase Cleavage site (Red)

1 MADDLDFETG DAGASATFPM QCSALRKNGF VVLKGRPCKI VEMSTSKTGK
   51 HGHAKVHLVG IDIFTGKKYE DICPSTHNMD VPNIKRNDFQ LIGIQDGYLS
  101 LLQDSGEVRE DLRLPEGDLG KEIEQKYDCG EEILITVLSA MTEEAAVAIK
  151 AMAK (SEQ ID NO:36)

C) Cleaved eIF5A1:

predicted mol. Wt.: 16.16 kDa
predicted pI: 5.57

7        FETG DAGASATFPM QCSALRKNGF VVLKGRPCKI VEMSTSKTGK
   51 HGHAKVHLVG IDIFTGKKYE DICPSTHNMD VPNIKRNDFQ LIGIQDGYLS
  101 LLQDSGEVRE DLRLPEGDLG KEIEQKYDCG EEILITVLSA MTEEAAVAIK
  151 AMAK (SEQ ID NO:37)

Figure 38: Predicted Sequence of the Cleaved Form of eIF5A1
A) Amino acid sequence, molecular weight and pI of the full-length form of eIF5A1. B) Sequence of putative caspase cleavage site (underlined). C) Amino acid sequence, molecular weight and pI of the cleaved form of eIF5A1

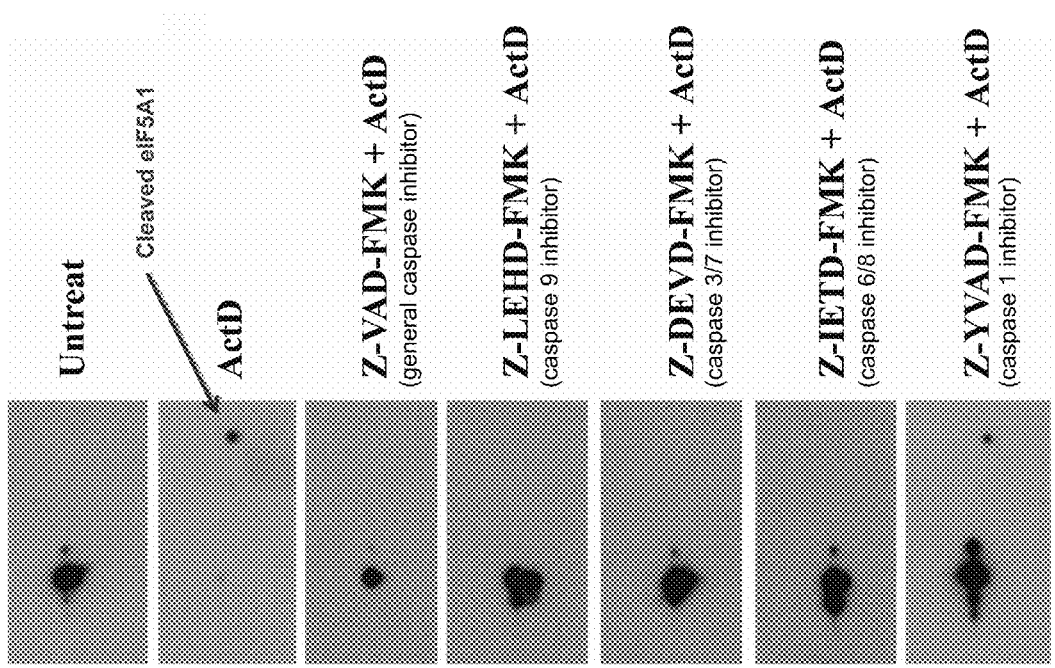
Figure 39: Caspase 3, 8 and 9 Inhibitors Inhibit Formation of Cleaved Form of eIF5A1

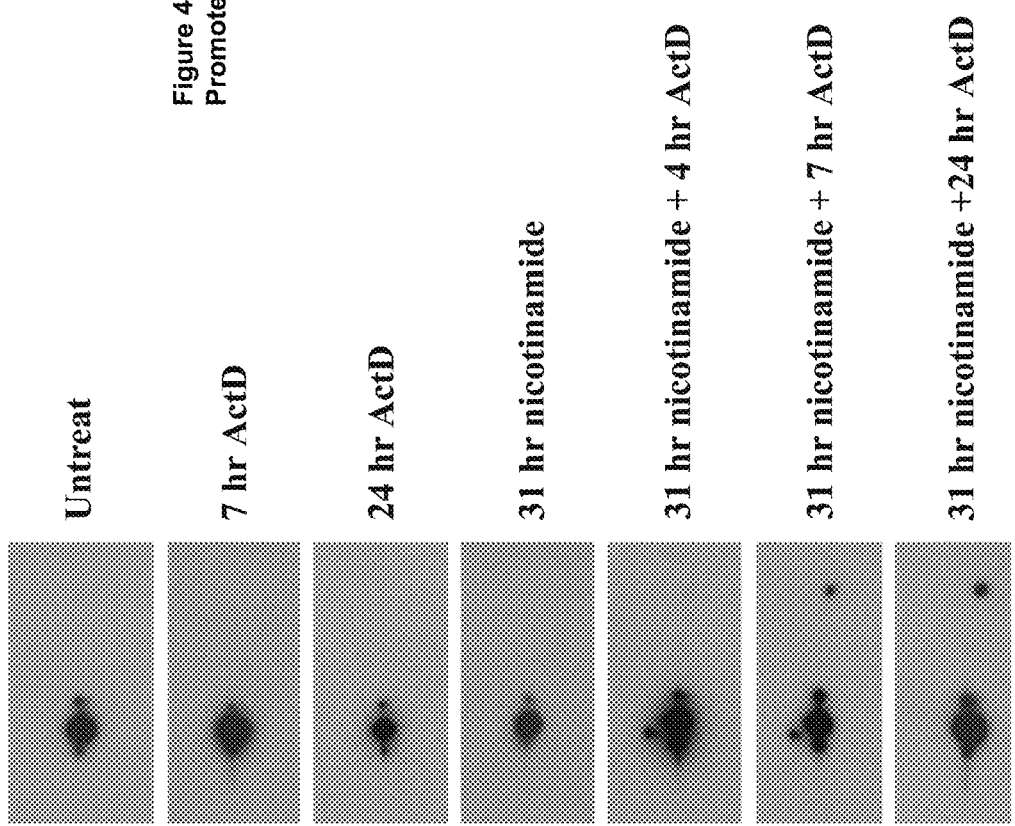

Figure 41: DNA sequence of truncated eIF-5A1 (human)

```
TTCGAGACAGGAGATGCAGGGGCCTCAGCCACCTTCCCAATGCAGTGCTCAGCATTACGTAAGAA
TGGCTTTGTGGTGCTCAAAGGCCGGCCATGTAAGATCGTCGAGATGTCTACTTCGAAGACTGGCA
AGCACGGCCACGCCAAGGTCCATCTGGTTGGTATTGACATCTTTACTGGGAAGAAATATGAAGAT
ATCTGCCCGTCAACTCATAATATGGATGTCCCCAACATCAAAAGGAATGACTTCCAGCTGATTGG
CATCCAGGATGGGTACCTATCACTGCTCCAGGACAGCGGGGAGGTACGAGAGGACCTTCGTCTCC
CTGAGGGAGACCTTGGCAAGGAGATTGAGCAGAAGTACGACTGTGGAGAAGAGATCCTGATCACG
GTGCTGTCTGCCATGACAGAGGAGGCAGCTGTTGCAATCAAGGCCATGGCAAAATAA    (SEQ
ID NO: 38)
```

FIGURE 42

1) Protein sequence of the full length eIF5A1:
   1 maddldfetg dagasatfpm qcsalrkngf vvlkgrpcki vemstsktgk hghakvhlvg
   61 idiftgkkye dicpsthnmd vpnikrmdfq ligiqdgyls llqdsgevre dlripegdlg
   121 keieqkydcg eeilitvlsa mteeaavaik amak (SEQ ID NO: 39)

2) Protein sequence of the cleavage form of eIF5A1:
   1 fetgdagasa tfpmqcsalr kngfvvlkgr pckivemsts ktgkhghakv hlvgidiftg
   61 kkyedicpst hnmdvpnikr ndfqligiqd gylsllqdsg evredlripe gdlgkeieqk
   121 ydcgeeilit vlsamteeaa vaikamak (SEQ ID NO: 40)

3) Sequence of the cleavage site: (SEQ ID NO:41)

```
  1 maddldfetg dagasatfpm qcsalrkngf vvlkgrpcki vemstsktgk hghakvhlvg
 61 idiftgkkye dicpsthnmd vpnikrmdfq ligiqdgyls llqdsgevre dlripegdlg
121 keieqkydcg eeilitvlsa mteeaavaik amak
```

Yellow-highlighted part (maddld)(SEQ ID NO:42)is the sequence that is cleaved off from eIF5A1. Arrow indicates the cleavage site.

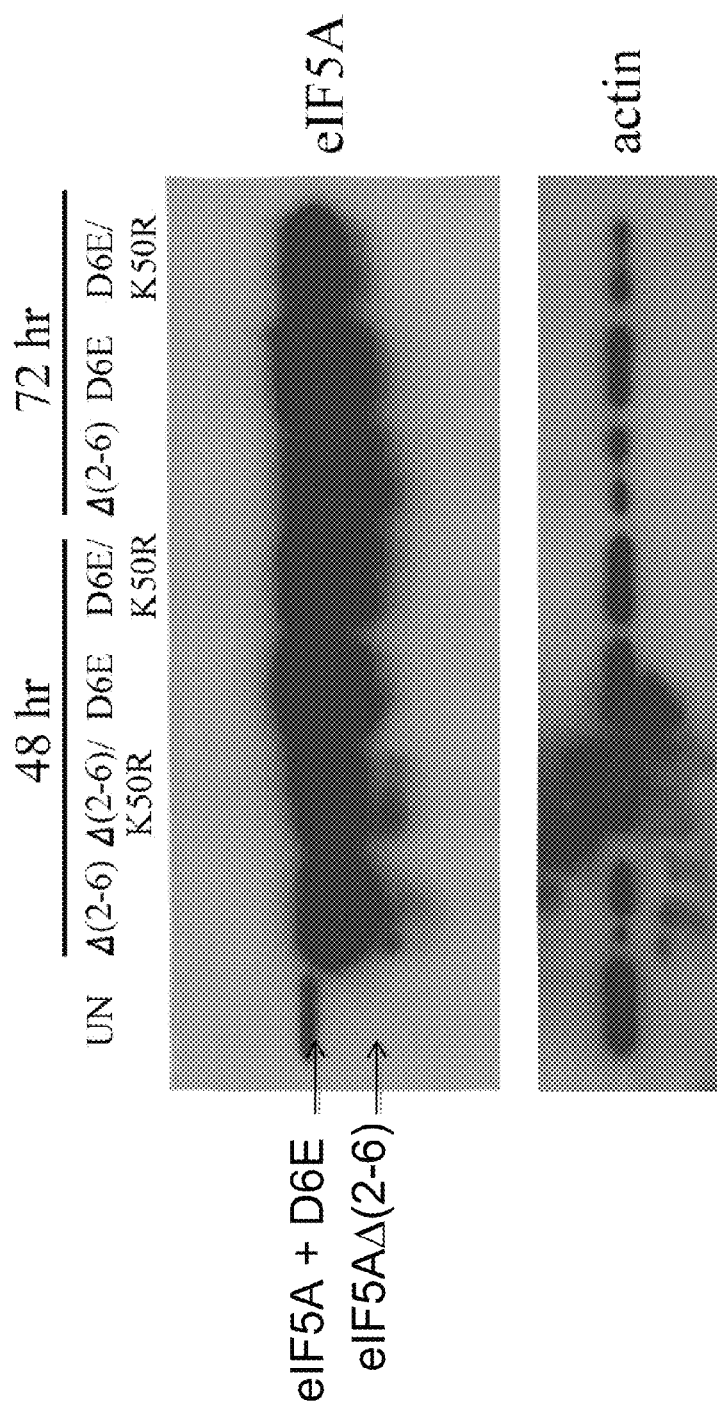
Figure 43: Infection of Hela cells with adenovirus constructs results in accumulation of eIF5A transgene.

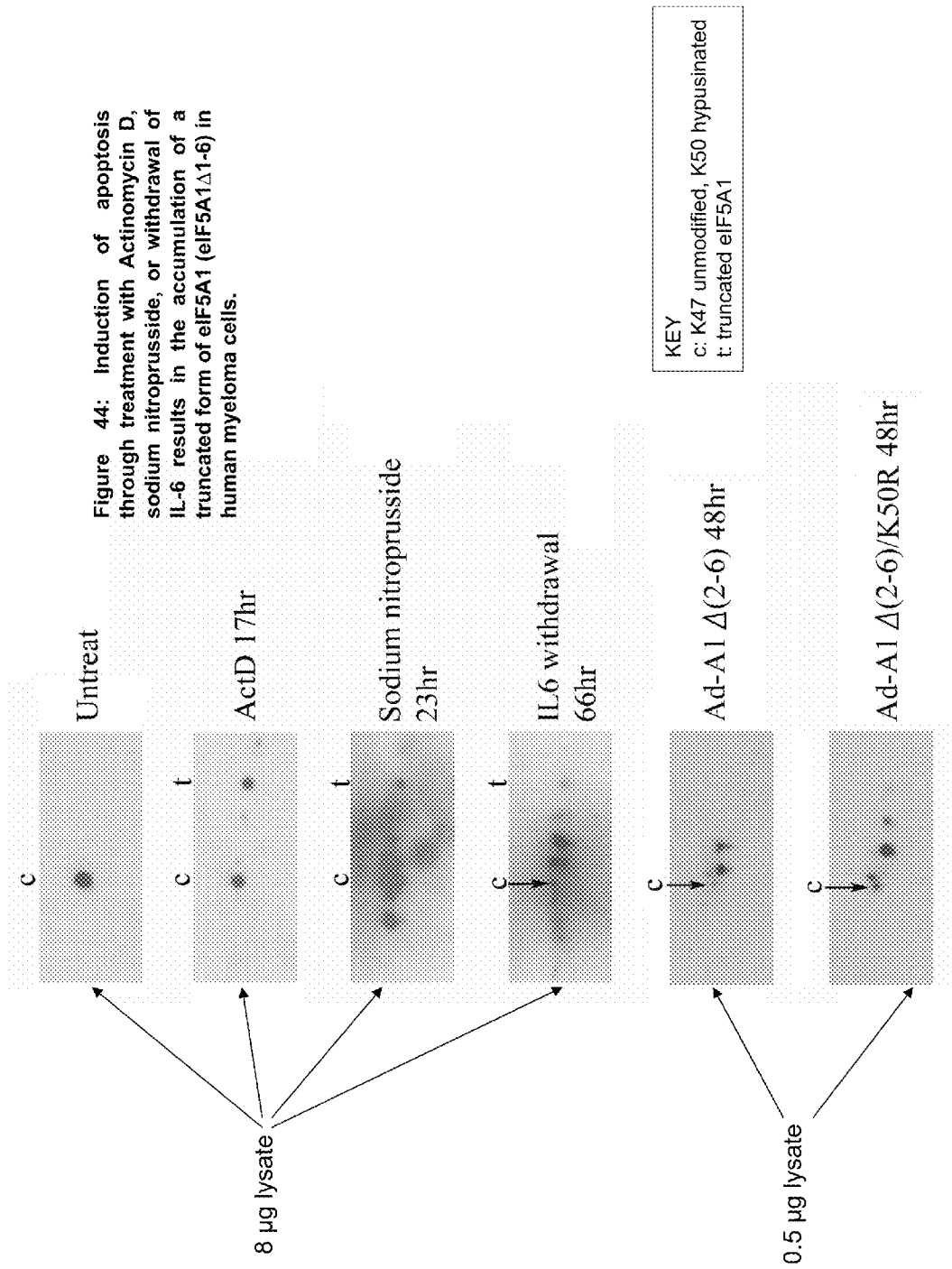
Figure 44: Induction of apoptosis through treatment with Actinomycin D, sodium nitroprusside, or withdrawal of IL-6 results in the accumulation of a truncated form of eIF5A1 (eIF5A1Δ1-6) in human myeloma cells.

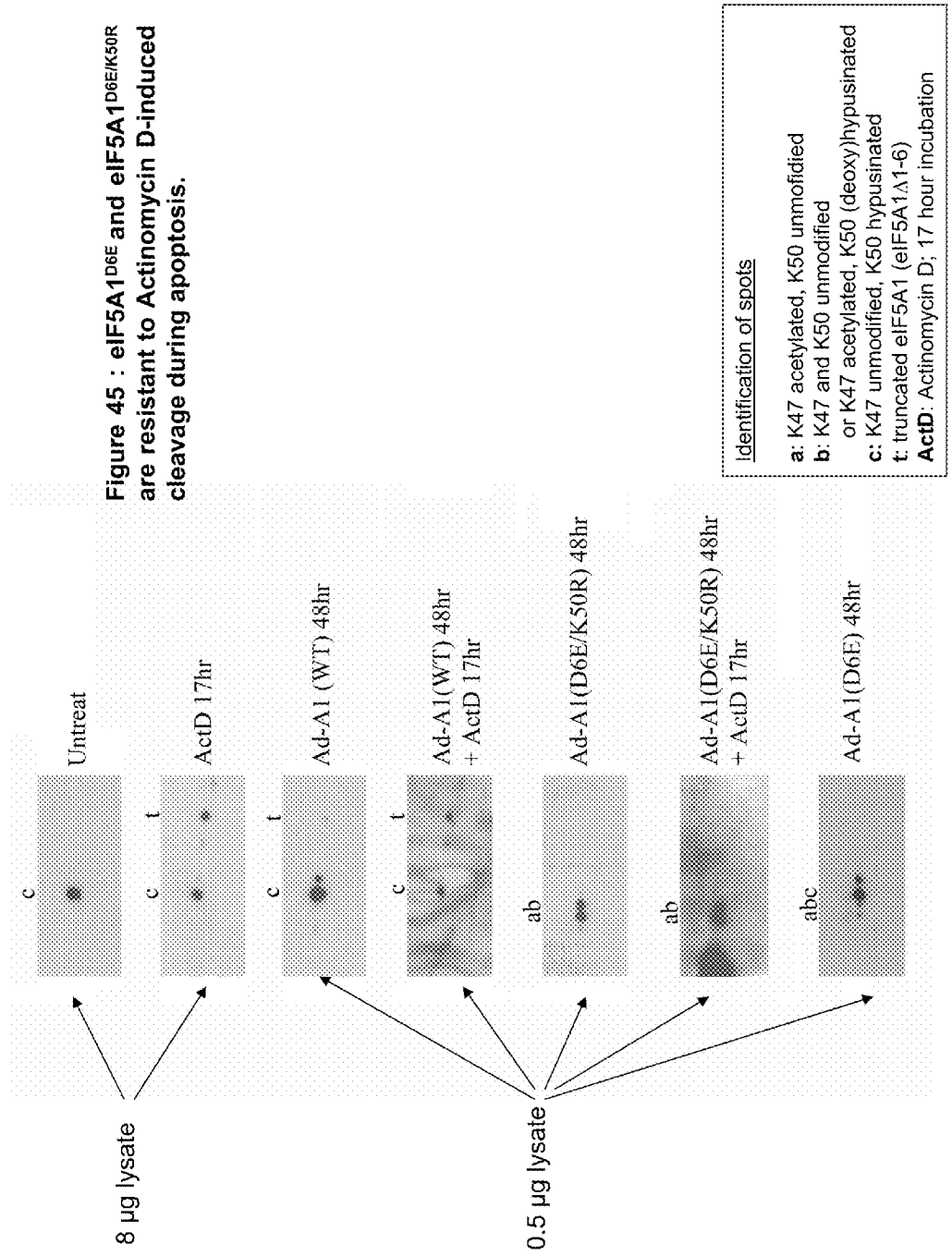
Figure 45: eIF5A1^D6E and eIF5A1^D6E/K50R are resistant to Actinomycin D-induced cleavage during apoptosis.

eIF5A1 is cleaved *in vitro* by recombinant caspases.

Figure 47: Infection of Hela cells with Ad-eIF5A1Δ(2-6) or Ad-eIF5A1^{K50R}Δ(2-6) results in increased apoptosis compared to infection with wild-type Ad-eIF5A1 or Ad-eIF5A1^{K50R}

Model of contribution of caspase-mediated truncation of eIF5A1 in apoptosis.

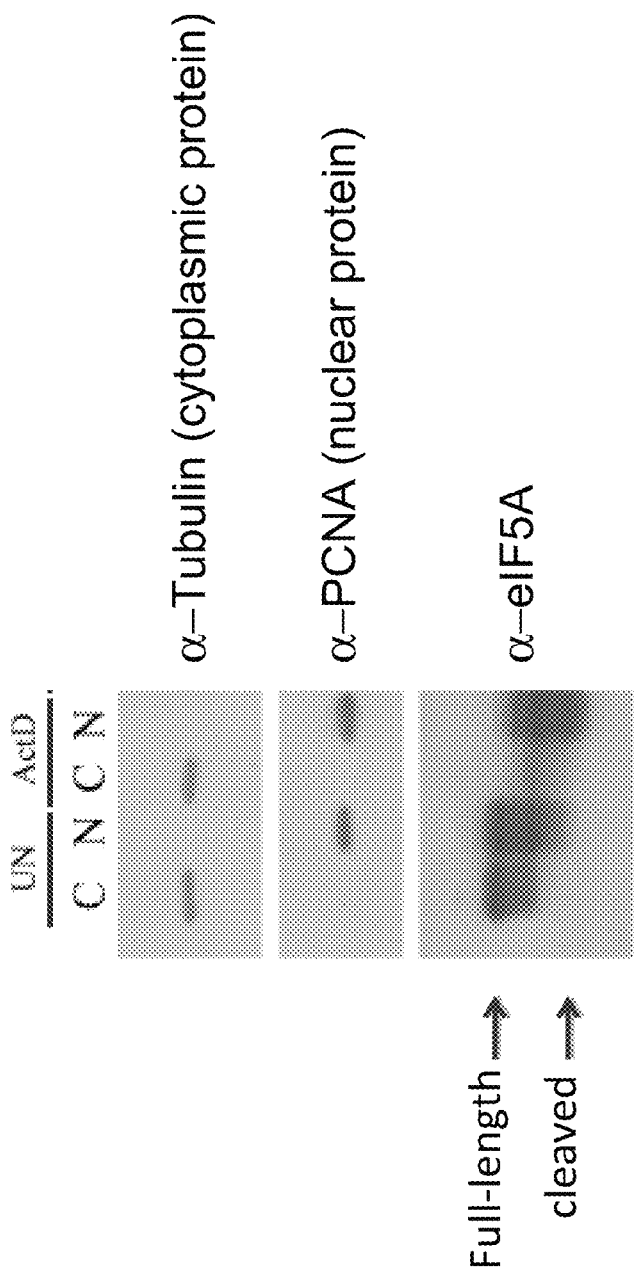
Figure 49: Cleaved eIF5A accumulates in the nucleus following Actinomycin D Treatment in KAS human myeloma cells

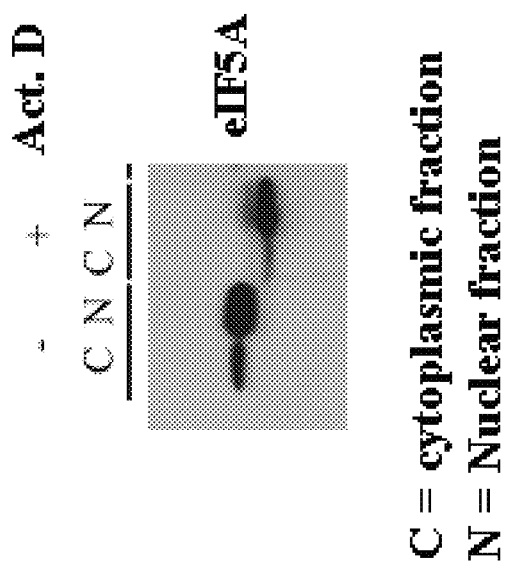
Figure 50 : Cleaved eIF5A accumulates in the nucleus following Actinomycin D Treatment in KAS human myeloma cells

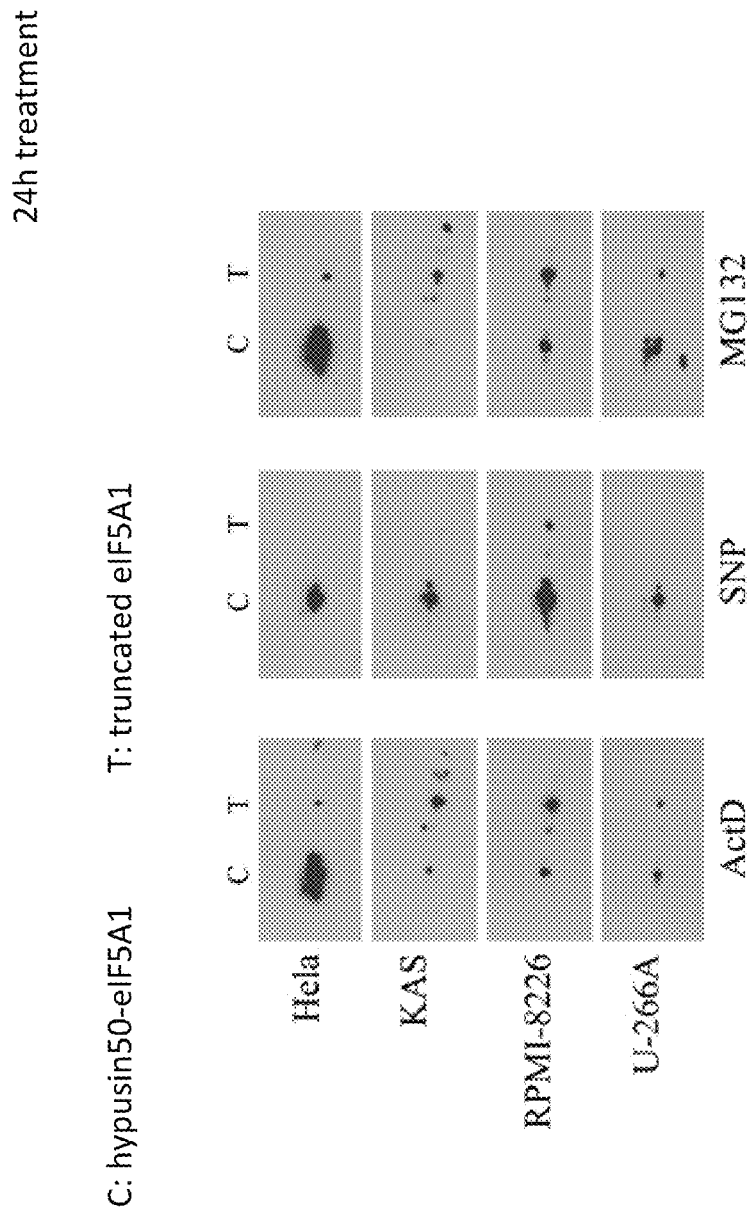

Figure 51: The truncated form of eIF5A accumulates in response to different apoptotic stimuli in multiple cell lines and cell types indicating that caspase-mediated cleavage of eIF5A is a common phenomena during apoptosis.
ActD = Actinomycin D; SNS = sodium nitroprusside; MG132 = proteosome inhibitor
Hela = cervical cancer cell line; KAS and RPMI-8226 and U266A = multiple myeloma NUCLEOTIDE ALIGNMENT OF HUMAN eIF5A1 (ACC. NM_001970) AND HUMAN eIF5A2 (ACC. NM_020390)

```
eIF5a1    1   ATGGCAGATG ACTTGGACTT CGAgACAGGA GATGCAGGGG CCTCAGCCAC
eIF5a2    1   ATGGCAGACG AAATTGATTT CACTACTGGA GATGCCGGGG CTTCCAGCAC eIF5a1   51   CTTCCCAATG CAGTGCTCAG CATTACGtAA GAATGGCTTT GTGGTGCTCA
eIF5a2   51   TTACCCTATG CAGTGCTCGG CCTTGGCAA  AAACGGCTTC GTGGTGCTCA eIF5a1  101   AAGGCCGGCC ATGtAAGATC GTCGAGATGT CTACTTCGAA GACTGGCAAG
eIF5a2  101   AAGGACGACC ATGCAAAATA GTGGAGATGT CAACTTCCAA AACTGGAAAG eIF5a1  151   CACGGCCACG CCAAGGTCCA TCTGGTTGGT ATTGACATCT TtACTGGGAA
eIF5a2  151   CAtGGTCATG CCAAGGTTCA CCTTGTTGGA ATTGATATTT TCACGGGCAA eIF5a1  201   GAAATATGAA GATATCTGCC CGTCAACTCA CTGATTGGCA GTCCCCAACA
eIF5a2  201   AAAATATGAA GATATTTGTC CTTCTACTCA CAACATGGAT GTTCCAAATA eIF5a1  251   TCAAAAGGAA TGACTtCCAG ACAGGCGGGA GGTACGAGAG TCCAGGATGG GTACCTATCA
eIF5a2  251   TTAAGAGAAA TGATTatCAA AAACTGGTGA AGTTCGTGAG TTCAAGATGG TTACCTTTCC eIF5a1  301   CTGCTccagG ACAGGCGGGA GGTACGAGAG GACCTTCGTC TcCCTGAGGG
eIF5a2  301   CTGCTgacaG AAACTGGTGA AGTTCGTGAG GATCTTAAAC TgCCAGAAGG eIF5a1  351   AGACCTTGGC AAGGAGATTG AGcagAAGTA CGACTGTGGA GAAGAGATCC
eIF5a2  351   TGAACTAGGC AAAGAAATAG AGggaAAATA CAATGCAGGT GAAGATGTAC eIF5a1  401   TGATCACGGT GCTGTCTGCC ATGACAGAGG AGGCAGCTGT TGCAATCAAG
eIF5a2  401   AGGTGTCTGT CATGTGTGCA ATGAGTGAAG AATATGCTGT AGCCATAAAA eIF5a1  451   GCCatgGCAA AATAa       SEQ ID NO: 43
eIF5a2  451   CCCt--GCAA ATAA-       SEQ ID NO: 44
```

FIG. 53

USE OF A TRUNCATED EIF-5A1 POLYNUCLEOTIDE TO INDUCE APOPTOSIS IN CANCER CELLS

RELATED APPLICATIONS

This application is a continuation-in-part of U.S. patent application Ser. No. 12/400,742, filed Mar. 9, 2009, and claims the benefit of U.S. Provisional Application No. 61/093,749, filed Sep. 3, 2008, each of which are herein incorporated by reference in their entirety.

SEQUENCE LISTING

The current application contains a Sequence Listing which has been submitted via EFSWeb and is hereby incorporated by reference in its entirety. The ASCII copy of the sequence listing was created on Nov. 11, 2009, is named 29123S01.txt, and is 38,810 bytes in size.

BACKGROUND OF THE INVENTION

Relatively recently, researchers observed that double stranded RNA ("dsRNA") could be used to inhibit protein expression. This ability to silence a gene has broad potential for treating human diseases, and many researchers and commercial entities are currently investing considerable resources in developing therapies based on this technology.

Double stranded RNA induced gene silencing can occur on at least three different levels: (i) transcription inactivation, which refers to RNA guided DNA or histone methylation; (ii) siRNA induced mRNA degradation; and (iii) mRNA induced transcriptional attenuation.

It is generally considered that the major mechanism of RNA induced silencing (RNA interference, or RNAi) in mammalian cells is mRNA degradation. Initial attempts to use RNAi in mammalian cells focused on the use of long strands of dsRNA. However, these attempts to induce RNAi met with limited success, due in part to the induction of the interferon response, which results in a general, as opposed to a target-specific, inhibition of protein synthesis. Thus, long dsRNA is not a viable option for RNAi in mammalian systems.

More recently it has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al. (2002) Ribonuclease Activity and RNA Binding of Recombinant Human Dicer, EMBO J. 21(21): 5864-5874; Tabara et al. (2002) The dsRNA Binding Protein RDE-4 Interacts with RDE-1, DCR-1 and a DexH-box Helicase to Direct RNAi in *C. elegans*, Cell 109(7):861-71; Ketting et al. (2002) Dicer Functions in RNA Interference and in Synthesis of Small RNA Involved in Developmental Timing in *C. elegans*; Martinez et al., Single-Stranded Antisense siRNAs Guide Target RNA Cleavage in RNAi, Cell 110(5):563; Hutvagner & Zamore (2002) A microRNA in a multiple-turnover RNAi enzyme complex, Science 297:2056.

From a mechanistic perspective, introduction of long double stranded RNA into plants and invertebrate cells is broken down into siRNA by a Type III endonuclease known as Dicer. Sharp, RNA interference—2001, Genes Dev. 2001, 15:485. Dicer, a ribonuclease-III-like enzyme, processes the dsRNA into 19-23 base pair short interfering RNAs with characteristic two base 3' overhangs. Bernstein, Caudy, Hammond, & Hannon (2001) Role for a bidentate ribonuclease in the initiation step of RNA interference, Nature 409:363. The siRNAs are then incorporated into an RNA-induced silencing complex (RISC) where one or more helicases unwind the siRNA duplex, enabling the complementary antisense strand to guide target recognition. Nykanen, Haley, & Zamore (2001), ATP requirements and small interfering RNA structure in the RNA interference pathway, Cell 107:309. Upon binding to the appropriate target mRNA, one or more endonucleases within the RISC cleaves the target to induce silencing. Elbashir, Lendeckel, & Tuschl (2001) RNA interference is mediated by 21- and 22-nucleotide RNAs, Genes Dev. 15:188, FIG. 1.

The interference effect can be long lasting and may be detectable after many cell divisions. Moreover, RNAi exhibits sequence specificity. Kisielow, M. et al. (2002), Isoform-specific knockdown and expression of adaptor protein ShcA using small interfering RNA, J. Biochem. 363:1-5. Thus, the RNAi machinery can specifically knock down one type of transcript, while not affecting closely related mRNA. These properties make siRNA a potentially valuable tool for inhibiting gene expression and studying gene function and drug target validation. Moreover, siRNAs are potentially useful as therapeutic agents against: (1) diseases that are caused by over-expression or misexpression of genes; and (2) diseases brought about by expression of genes that contain mutations.

Successful siRNA-dependent gene silencing depends on a number of factors. One of the most contentious issues in RNAi is the question of the necessity of siRNA design, i.e., considering the sequence of the siRNA used. Early work in *C. elegans* and plants circumvented the issue of design by introducing long dsRNA (see, for instance, Fire, A. et al. (1998) Nature 391:806-811). In this primitive organism, long dsRNA molecules are cleaved into siRNA by Dicer, thus generating a diverse population of duplexes that can potentially cover the entire transcript. While some fraction of these molecules are non-functional (i.e., induce little or no silencing) one or more have the potential to be highly functional, thereby silencing the gene of interest and alleviating the need for siRNA design. Unfortunately, due to the interferon response, this same approach is unavailable for mammalian systems. While this effect can be circumvented by bypassing the Dicer cleavage step and directly introducing siRNA, this tactic carries with it the risk that the chosen siRNA sequence may be non-functional or semi-functional.

A number of researches have expressed the view that siRNA design is not a crucial element of RNAi. On the other hand, others in the field have begun to explore the possibility that RNAi can be made more efficient by paying attention to the design of the siRNA.

To treat various diseases or disorders, the upregulation of certain proteins is desirable but this may not be all that is needed. For example, the combinatorial use of siRNA to knock down or knock out expression of an endogenous protein or a different protein may be needed. The present invention fulfills this need and provides methods of treating cancer, especially multiple myeloma.

Cancer, including multiple myeloma are diseases which would benefit from the ability to induce apoptosis. Conventional therapies for of multiple myeloma include chemotherapy, stem cell transplantation, high-dose chemotherapy with stem cell transplantation, and salvage therapy. Chemotherapies include treatment with Thalomid® (thalidomide), bortezomib, Aredia® (pamidronate), steroids, and Zometa®

(zoledronic acid). However many chemotherapy drugs are toxic to actively dividing non-cancerous cells, such as of the bone marrow, the lining of the stomach and intestines, and the hair follicles. Therefore, chemotherapy may result in a decrease in blood cell counts, nausea, vomiting, diarrhea, and loss of hair.

Conventional chemotherapy, or standard-dose chemotherapy, is typically the primary or initial treatment for patients with of multiple myeloma. Patients also may receive chemotherapy in preparation for high-dose chemotherapy and stem cell transplant. Induction therapy (conventional chemotherapy prior to a stem cell transplant) can be used to reduce the tumor burden prior to transplant. Certain chemotherapy drugs are more suitable for induction therapy than others, because they are less toxic to bone marrow cells and result in a greater yield of stem cells from the bone marrow. Examples of chemotherapy drugs suitable for induction therapy include dexamethasone, thalidomide/dexamethasone, VAD (vincristine, Adriamycin® (doxorubicin), and dexamethasone in combination), and DVd (pegylated liposomal doxorubicin (Doxil®, Caelyx®), vincristine, and reduced schedule dexamethasone in combination).

The standard treatment for of multiple myeloma is melphalan in combination with prednisone (a corticosteroid drug), achieving a response rate of 50%. Unfortunately, melphalan is an alkylating agent and is less suitable for induction therapy. Corticosteroids (especially dexamethasone) are sometimes used alone for multiple myeloma therapy, especially in older patients and those who cannot tolerate chemotherapy. Dexamethasone is also used in induction therapy, alone or in combination with other agents. VAD is the most commonly used induction therapy, but DVd has recently been shown to be effective in induction therapy. Bortezomib has been approved recently for the treatment of multiple myeloma, but it is very toxic. However, none of the existing therapies offer a significant potential for a cure. Thus, there still remains a need to find a suitable treatment for cancer and multiple myeloma. The present invention fulfills this need.

SUMMARY OF INVENTION

The present invention provides an isolated polynucleotide encoding a truncated form of eIF-5A1 as well as a truncated eIF-A1 polypeptide. The truncated eIF-5A1 polynucleotide is useful in inducing apoptosis and killing cancer cells in a subject. The truncated polynucleotide may be used within an expression vector which is then administered to a subject. The truncated eIF-5A form is expressed within the mammal and kills cancer cells. The truncated eIF-5A1 protein is about 16 kDA as opposed to the full length eIF-5A1 protein, which is about 17 kDa. A polynucleotide encoding a truncated eIF5A1 protein may be used to make a medicament used to induce apoptosis in a cancer cell or a tumor in a subject. The polynucleotide encoding a truncated eIF5A1 protein may be used in conjunctions with other embodiments described herein (for example in combination with a polynucleotide encoding full length eIF5A1, with a polynucleotide encoding full length mutant eIF5A1, and/or with an siRNA targeted against the 3'UTR of eIF5A).

The present invention also relates to the combinatorial use of an siRNA targeted against an endogenous gene to knock out or knock down expression of the endogenous gene in a host and a delivery of a polynucleotide encoding the gene in a delivery vehicle/expression vector to the host to provide expression in the host of the protein encoded by the polynucleotide. A polynucleotide encoding a normal (non faulty) protein (or the protein itself) is administered to the host and is expressed (in the case of the polynucleotide) so that the normal protein can perform its necessary function. The siRNA is preferably designed to target a region of the gene so it either knocks down or knocks out endogenous expression of the faulty protein but at the same time will not effect exogenous expression of the administered polynucleotide encoding the normal protein.

The invention provides a composition comprising a complex of an eIF5A1 siRNA targeted against the 3' end of eIF5A1, an expression vector comprising a polynucleotide encoding a mutant eIF5A1 wherein the mutant eIF5A1 is unable to be hypusinated, and wherein the siRNA and the expression vector are complexed to polyethylenimine to form a complex.

The invention provides a composition comprising an siRNA targeted against a target gene to suppress endogenous expression of the target gene is a subject, and a polynucleotide encoding a target protein capable of being expressed in the subject. In certain embodiments the polynucleotide is in RNAi resistant plasmid (will not be suppressed by the siRNA). The siRNA and the plasmid are preferably complexed to polyethylenimine to form a complex.

In certain embodiments the siRNA has the sequence shown in FIG. 25 and wherein the polynucleotide encoding the mutant eIF5A1 is eIF5A1$^{K50R}$. The expression vector comprises a polynucleotide encoding a mutant eIF5A1 and a promoter operably linked to provide expression of the polynucleotide in a subject. The promoter preferably is either tissue specific or systemic. For example, if the composition is used to treat cancer, then preferably the promoter is tissue specific for the tissue in which the cancer resides. For example, for treating multiple myeloma, it is preferable to use a B cell specific promoter, such as B29. In certain embodiments, the expression vector comprises a pCpG plasmid.

In certain embodiments, the eIF5A1 siRNA and the expression vector comprising the mutant eIF5A1 polynucleotide are independently complexed to polyethylenimine, such as in vivo JetPEI™. In other embodiments, the eIF5A1 siRNA and the expression vector comprising the mutant eIF5A1 polynucleotide are complexed together to polyethylenimine.

The present invention further provides a composition comprising an eIF5A1 siRNA targeted against the 3' end of eIF5A1 and an expression vector comprising a polynucleotide encoding a mutant eIF5A1 wherein the mutant eIF5A1 is unable to be hypusinated, and wherein the siRNA and the expression vector are delivered to a subject to treat cancer. The cancer may be any cancer including multiple myeloma.

The present invention further provides a method of treating cancer comprising administering composition of the present invention to a subject (including but not limited to mammals and humans).

The composition may be administered any acceptable route, such as, but not limited to intravenously, intra peritoneally, subcutaneously or intra tumorally. The siRNA and the expression vector may be administered at different times and via different routes or may be administered together at the same time and via the same route. For example, but not limited to, the siRNA may be delivered naked or complexed to a carrier such as in vivo jetPEI via IV and the expression vector may be administered intra tumorally, or both the siRNA and the expression vector may be administered IV or intratumorally, etc.

The present invention provides a method of inhibiting cancer cell growth and/or killing cancer cells. The present invention also provides a method of inhibiting or slowing down the ability of a cancer cell to metastasize. Inhibiting cancer growth includes a reduction in the size of a tumor, a decrease in the growth of the tumor, and can also encompass a complete remission of the tumor. The cancer can be any cancer or tumor, including but not limited to colon cancer, colorectal adenocarcinoma, bladder carcinoma, cervical adenocarcinoma, and lung carcinoma. Preferably the cancer is multiple myeloma.

In preferred embodiments, the eIF-5A is a mutant that is unable to be hypusinated. Exemplary mutants are described herein.

In addition to providing eIF-5A or a polynucleotide encoding eIF-5A to a subject (to provide expression of the eIF-5A), siRNA is provided to knock out or knock down endogenous expression of eIF-5A.

The present invention also provides the use of eIF5A, polynucleotides encoding eIF5A1 and siRNA against eIF5A1 to make a medicament to treat cancer kill multiple myeloma cells in a subject having multiple myeloma. Preferably the polynucleotides encoding a mutant eIF-5A are unable to be hypusinated.

The present invention also provides a method of treating sickle cell anemia. A polynucleotide encoding a healthy hemoglobin gene (such as HBB) is administered to a patient suffering from sickle cell anemia. In conjunction, the patient is also administered siRNA that targets the gene encoding the faulty hemoglobin gene (such as the gene encoding the mutant HbS) to knock down or knock out expression of the faulty protein. The treatment may further comprise administration of other known medicines or treatments commonly used in treating sickle cell anemia.

BRIEF DESCRIPTION OF THE FIGURES

FIG. 1 provides the amino acid sequence of human eIF-5A1(SEQ ID NO: 19) and shows various important sites. PHM6-eIF5A1 and Consensus sequence each disclosed as SEQ ID NO:29.

FIG. 7A shows transfection with siRNA and treating with an adenovirus that is modified to express eIF-5A1 results in apoptosis in KAS cells. See example 6A.

FIG. 18 shows that administration of eIF5A1 siRNA intra-venously (i.v.) and PEI/eIF5A1K50R plasmid complexes intra-tumorally (i.t.) results in tumor shrinkage of multiple myeloma subcutaneous tumors. See example 13.

FIG. 23 shows the predicted sequence of pExp5A (3370 bp) (SEQ ID NO: 30). See example 17.

FIG. 25 shows the target sequence (SEQ ID NO: 31) and the sequence of a preferred eIF5A1 siRNA (SEQ ID NOs: 31 and 32, respectively, in order of appearance).

FIG. 28 provides the sequence of eIF-5A1$^{k50R}$ cDNA (SEQ ID NO: 33) and protein (SEQ ID NO: 34). FIG. 28 also discloses the HA-tag as residues 25-54 of SEQ ID NO: 33.

FIG. 29 provides the alignment of human eIF-5A1 (SEQ ID NO: 19) against human eIF5A1$^{k50R}$ (SEQ ID NO: 6). The Consensus sequence is disclosed as SEQ ID NO: 6.

FIG. 30 shows the effect of DNA:siRNA ratio on HA-eIF5A$^{K50R}$ expression. See example 23.

FIG. 33 shows that the JET PEI™ nanoparticles are being effectively taken up by tumor tissue and that nanoparticles are delivering plasmid and siRNA to the same cell. See example 26.

FIG. 34 shows that KAS cells undergo apoptosis in response to Actinomycin D. KAS cells were either left untreated or were treated with 0.5 μg/ml Actinomycin D. Twenty-four hours after the initiation of treatment, the cells were harvested, washed, and apoptotic cells were labeled using Annexin/PI (BD Bioscience) and analyzed by flow cytometry.

FIG. 35 shows that a truncated form of eIF-5A1 accumulates in response to actinomycin D treatment. KAS cells were treated with 0.5 μg/ml Actinomycin D for time periods ranging from 0 hours to 30 hours. Cell lysate was harvested and analyzed by Western blot using an antibody against eIF5A1. Accumulation of a smaller molecular weight (cleaved) form of eIF5A1 was observed beginning at approximately 8 hours after Actinomycin D treatment and was present throughout the remainder of the treatment. Equal loading is demonstrated by Western blot of the same membrane using an antibody against actin.

FIG. 36 shows that the truncated form of eIF-5A1 has a higher isoelectric point than the full length eIf-5A1. KAS cells were either left untreated or were treated with 0.5 μg/ml Actinomycin D. Seventeen hours after the initiation of treatment, the cell lysates were harvested and separated by 2-D gel electrophoresis followed by Western blot analysis using an antibody against eIF5A1. A large amount of the full-length eIF5A1 can be observed in the untreated sample while accumulation of a cleaved form of eIF5A1 with a higher pI can be observed in the Actinomycin D-treated sample.

FIG. 37 provides a photograph of the truncated eIF-5A1 2-D gel. KAS cells were treated with 0.5 μg/ml Actinomycin D. Seventeen hours after the initiation of treatment, the cell lysate was harvested and separated by 2-D gel electrophoresis followed by Coomassie Blue staining. The position of the cleaved form of eIF5A1 that was collected for mass spectrometry analysis is indicated.

FIG. 38 provides the results of sequencing by mass spectrometry of the truncated eIF-5A1. (A) The full-length amino acid sequence of eIF5A1 is shown in black. Sequenced peptides identified by Mass spectrometry (B) that aligned with the full-length sequence of eIF5A1 are shown in underlined (A). Note that the first six amino acids of eIF5A1 are missing from the sequenced peptides.

FIG. 39 shows that caspase 3, 8 and 9 inhibitors inhibit formation of the truncated form of eIF-5A1. Human multiple myeloma KAS cells were incubated with different caspase inhibitors 8 hours before being co-treated with 0.5 μg/ml Actinomycin D (ActD) for another 16 hours. Cell lysates were collected. Proteins were isolated by 2D-PAGE and subjected to western analysis using antibody against eIF5A. The caspase inhibitors used were Z-VAD-FMK (general caspase inhibitor), Z-LEHD-FMK (caspase 9 inhibitor) (LEHD is disclosed as SEQ ID NO: 48), Z-DEVD-FMK (caspase 3/7 inhibitor) (DEVD is disclosed as SEQ ID NO: 49), Z-IETD-FMK (caspase 6/8 inhibitor) (IETD is disclosed as SEQ ID NO: 50), and Z-YVAD-FMK (caspase 1 inhibitor) (YVAD is disclosed as SEQ ID NO: 51). Data indicated that the general caspase inhibitor and inhibitors for caspase 3, 8 and 9 all strongly prevent the formation of the cleavage form of eIF5A that accumulates during ActD-induced apoptosis in KAS cells. Caspase 1 inhibitor also reduces, but not complete blocks, the formation of the cleavage product. These results indicate that eIF5A1 is cleaved by caspases following genotoxic stress (induced by Actinomycin D); cleavage of eIF5A1 could alter its activity ie increase pro-apoptotic activity.

FIG. 40 shows that a deacetylase inhibitor (nicotinamide) promotes formation of the truncated form of eIF-5A1. eIF5A which can be acetylated on Lysine-47 is a substrate of a Sir2-related deacetylase Hst2 (Shirai et al., 2008). Human cervical carcinoma Hela S3 cells were treated with 0.5 μg/ml Actinomycin D (ActD) and/or 20 μM nicotinamide, a potent inhibitor of Sir2, for indicated lengths of time. Cell lysates were collected. Proteins were isolated by 2D-PAGE and subjected to western analysis using antibody against eIF5A. Treatment of Hela S3 cells with ActD or nicotinamide alone does not induce the accumulation of the cleavage form of eIF5A. However, in HeLa cells treated with both Actinomycin D and nicotinamide, the cleavage form of eIF5A is upregulated at least 4 hours after being exposed to ActD, suggesting that acetylation may promote the cleavage of eIF5A during apoptosis.

FIG. 41 provides the DNA sequence of truncated human eIF5A1.

FIG. 42 provides the protein sequence of full length eIF5A1, truncated eIF5As and the cleavage cite.

FIG. 43: Infection of Hela cells with adenovirus constructs results in accumulation of eIF5A transgene. Hela S3 cells were infected with different adenovirus constructs at 500 infectious units per cell. Cell lysates were collected at 48 and 72 hours after infection and subjected to SDS-PAGE and western blotting analysis using antibodies against eIF5A and actin. Accumulation of truncated eIF5A can be observed.

FIG. 44: Induction of apoptosis through treatment with Actinomycin D, sodium nitroprusside, or withdrawal of IL-6 results in the accumulation of a truncated form of eIF5A1 (eIF5A1Δ1-6) in human myeloma cells. KAS-6/1 cells were treated as indicated and then subjected to 2D-PAGE and western blotting analysis using antibody against eIF5A. Induction of apoptosis in KAS-6/1 cells via with Actinomycin D, the NO donor, sodium nitroprusside, or IL-6 starvation all induced the accumulation of truncated eIF5A1. Overexpression of truncated eIF5A1 using either Ad-A1 Δ(2-6) or Ad-A1 Δ(2-6)/K50R induced the accumulation of eIF5A1 proteins have a smaller pI than the truncated eIF5A1 (eIF5A1Δ1-6) produced during apoptosis, indicating that other post-translational modifications are present on eIF5A1Δ1-6).

FIG. 45: eIF5A1D6E and eIF5A1D6E/K50R are resistant to Actinomycin D-induced cleavage during apoptosis. Human multiple myeloma KAS-6/1 cells were treated as indicated and then subjected to 2D-PAGE and western blot analysis using antibody against eIF5A. Over-expressed eIF5A1 (Ad-A1) is subjected to cleavage during treatment with Actinomycin D. However, eIF5A1D6E or eIF5A1D6E/K50R are resistant to cleavage following treatment with Actinomycin D. These results are consistent with the hypothesis that amino acids 3 to 6 of eIF5A1 constitute a caspase cleavage site.

Figure 46:
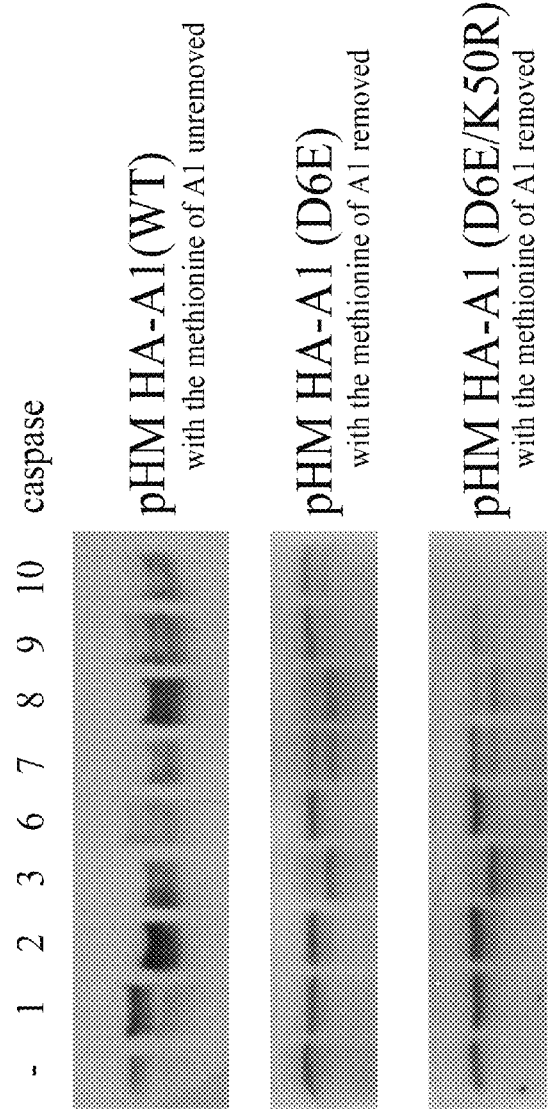

FIG. 46: eIF5A1 is cleaved in vitro by recombinant caspases. Human eIF5A1 (A1) and the mutants eIF5A1D6E (D6E) and eIF5A1D6E/K50R (D6E/KSOR) were subcloned into the pHM6 vector (Roche) which results in expression of an HA-tagged protein. pHM6-HA-A1, pHM6-HA-A1(D6E), and pHM6-HA-A1(D6E/KSOR) were in vitro transcribed and translated (TNT T7 Quick Coupled Transcription/Translation Systems; Promega) and labelled with Transcend Non-Radioactive Translation Detection Systems (Promega) following the manufacturer's instructions. Three microliters of each the in vitro translation products were incubated with one microliter of recombinant caspase (caspases 1, 2, 3, 6, 7, 8, 9, or 10; Calbiochem) in caspase reaction buffer (50 mM Hepes, 0.1% CHAPS, 10% sucrose, 100 mM NaCl, 10 mM DTT, 1 mM EDTA) at 37° C. for 2 hours. Final products were subjected to SDS-PAGE, and the biotinylated proteins were visualized by incubation with Streptavidin-HRP, followed by chemiluminescent detection. The wild-type eIF5A1 is cleaved by caspases 2, 3, 6, 7, 8, 9, and 10 but not by caspase 1. HA-tagged eIF5A1D6E and eIF5A1D6E/K50R are effectively cleaved in vitro by caspases 3, 7 and 8 but are not efficiently cleaved by caspases 9 and 10. However, this cleavage may be due to the highly abundant caspase activity in the in vitro system as well as the high structural similarity between glutamic acid and aspartic acid, thereby allowing cleavage of eIF5A1D6E, although at a reduced efficiency (particularly since eIF5A1D6E and eIF5A1D6E/K50R were resistant to cleavage in an in vivo assay (FIG. 45).

Figure 47:
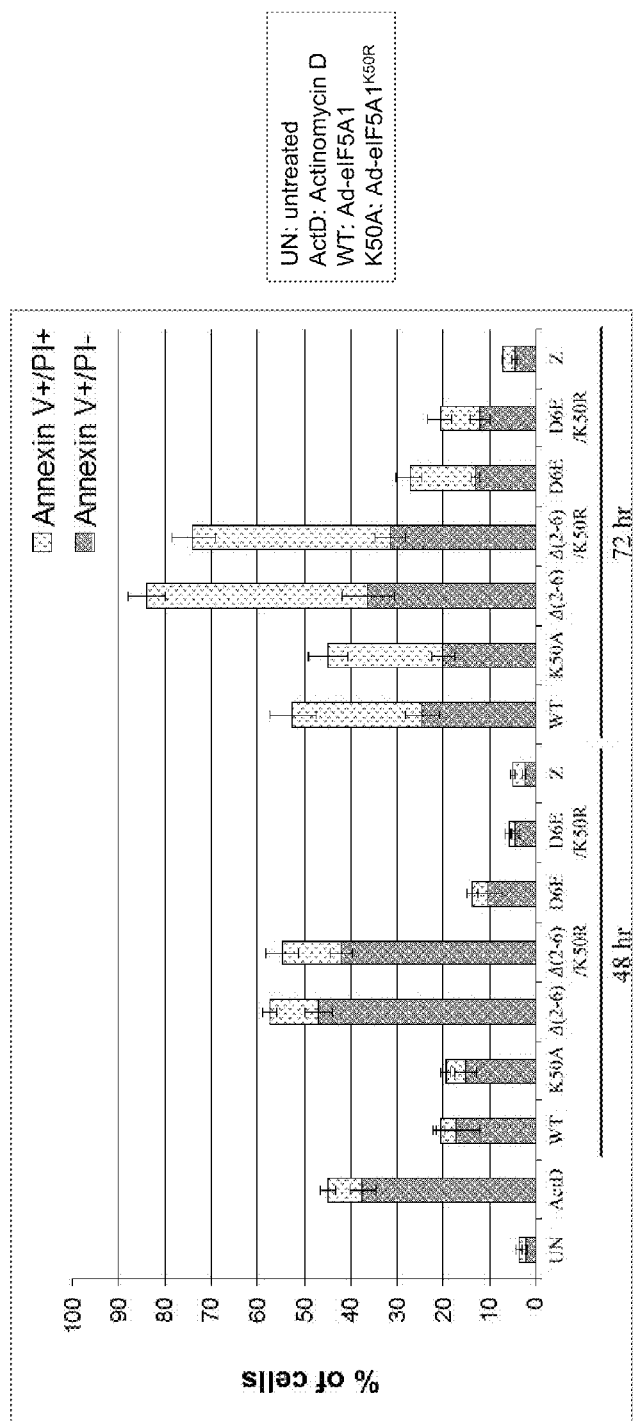

FIG. 47: Infection of Hela cells with Ad-eIF5A1Δ(2-6) or Ad-eIF5A1K50RΔ(2-6) results in increased apoptosis compared to infection with wild-type Ad-eIF5A1 or Ad-eIF5A1K50R. Human cervical cancer Hela S3 cells were infected with different adenovirus constructs at 500 infectious units per cell. At 48 or 72 hours after infection, cells were collected and subjected to Annexin V/PI staining Cells were then sorted by flow cytometry. Percentages of cells at early stage of apoptosis (Annexin V+/PI−), as well as cells at late stage of apoptosis (Annexin V+/PI+) are shown. Truncation of amino acids 2 to 6 increases the apoptotic activity of eIF5A1 or eIF5A1K50R. Conversely, mutation of the predicted cleavage site reduces, but does not eliminate, the apoptotic activity of eIF5A1 or eIF5A1K50R. These results indicate that caspase-mediated cleavage of eIF5A1 results in a truncated form of eIF5A1 with increased apoptotic activity.

Figure 48:
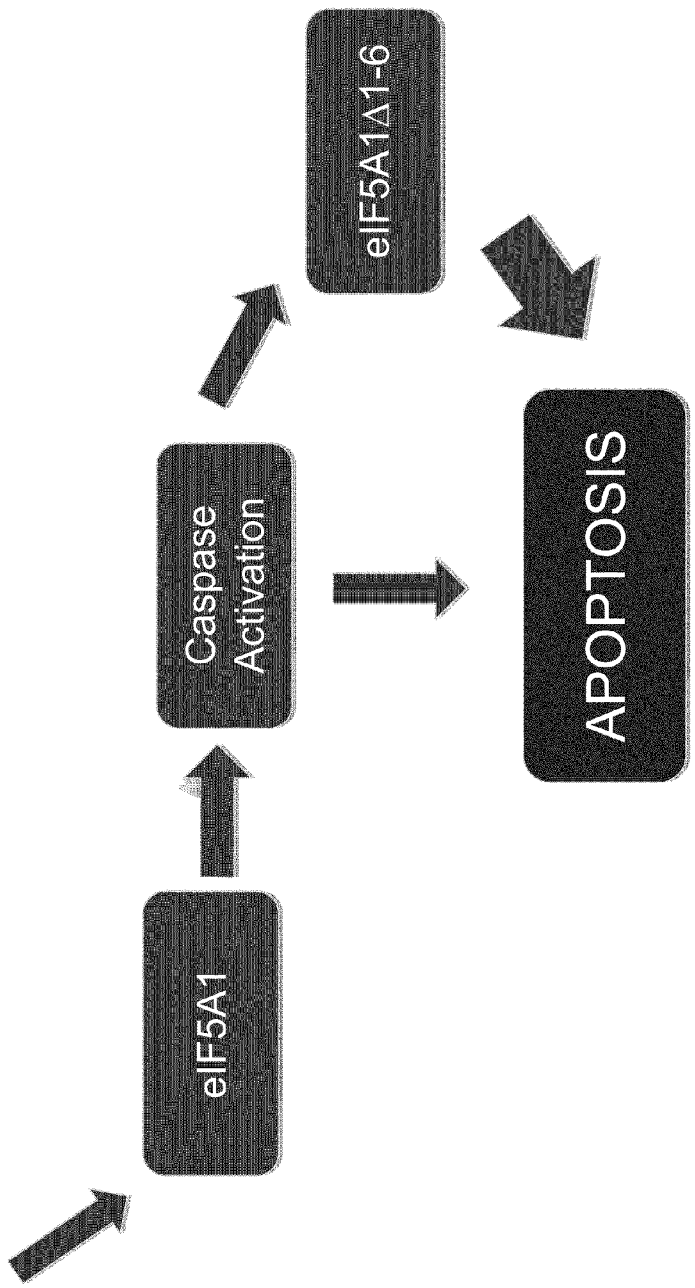

FIG. 48 provides a model of the contribution of caspase-mediated truncation of eIF-5A1 in apoptosis.

FIG. 49 shows that cleaved eIF5A accumulates in the nucleus following actinomycin D treatment in KAS human myeloma cells.

FIG. 50 shows that cleaved eIF5A accumulates in the nucleus following actinomycin D treatment in KAS human myeloma cells. Key: UN=untreated; actD=treatment with actinomycin D; C=cytoplasmic fraction; N=nuclear fraction, α-tubilin and α-PCNA are controls. This figure also shows that the truncated form accumulates predominantly in the nucleus, while the full length eIF5A is evenly distributed between the cytoplasm and nucleus.

FIG. 51 shows that the truncated form of eIF5A accumulates in response to different apoptotic stimuli in multiple cell lines and cell types indicating that caspase-mediated cleavage of eIF5A is a common phenomena during apoptosis. This figure also shows that the truncated form accumulates predominantly in the nucleus, while the full length eIF5A is evenly distributed between the cytoplasm and nucleus.

Figure 52:
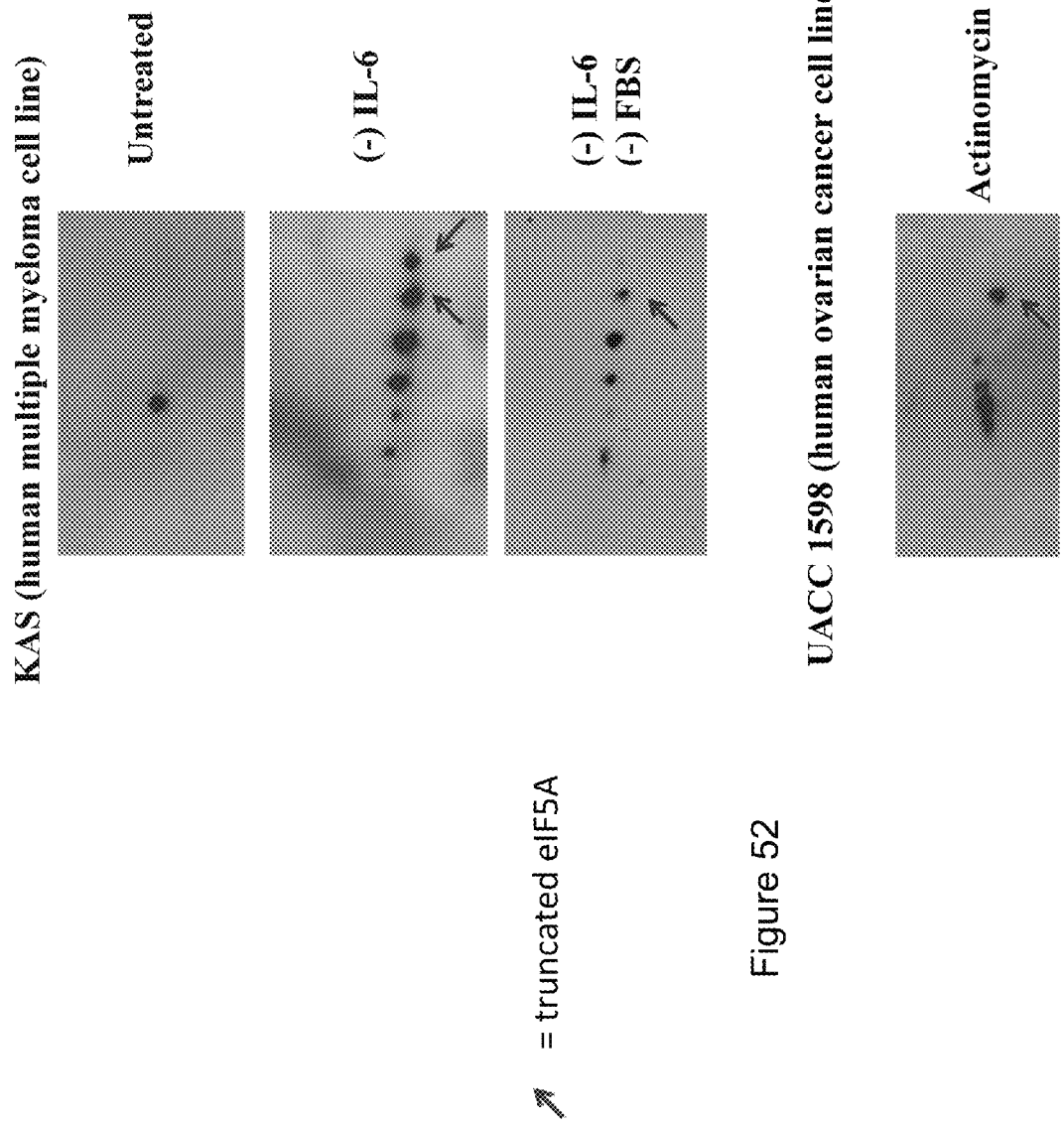

FIG. 52 provides results of a study that shows truncated eIF5A is produced in different cell lines in response to different apoptotic stimuli—KAS human multiple myeloma cells following treatment with IL-6 starvation or IL-6 and FBS starvation and in UACC 1598 (human ovarian cancer cell line) following treatment with actinomycin D.

FIG. 53 provides the nucleotide sequence of human eIF5A1 and eIF5A2.

DETAILED DESCRIPTION OF THE INVENTION

The present invention provides an isolated polynucleotide encoding a truncated form of eIF-5A1 as well as a truncated eIF-A1 polypeptide. The truncated eIF-5A1 polynucleotide is useful in inducing apoptosis and killing cancer cells. The truncated polynucleotide may be used within an expression vector which is then administered to a mammal. The truncated eIF-5A form is expressed within the mammal and kills cancer cells. The truncated eIF-5A1 protein is about 16 kDA as opposed to the full length eIf-5A1 protein, which is about 17 kDa.

Formation of a smaller molecular weight form of eIF5A (~16 kDa) has been observed in cells undergoing apoptosis. This has been observed in beta islet cells treated with a cytokine cocktail and in human myeloma cells (KAS cells) treated with the cytotoxic drug, Actinomycin D. See FIG. 35. The smaller molecular weight form of eIF5A has also been found to accumulate in HeLa cervical cancer cells undergoing apoptosis following infection with Ad-eIF5A1, suggesting that the smaller molecular weight form of eIF5A results from cleavage by proteases rather than being the result of alternative splicing. The observation that the accumulation of the smaller molecular weight form of eIF5A is accompanied by a dramatic reduction in the amount of full-length hypusinated eIF5A further supports that the smaller molecular weight form of eIF5A is due to cleavage rather than alternative splicing. See FIG. 36.

The present invention provides a composition comprising an eIF5A1 polynucleotide that encodes a truncated eIF5A1 protein. This composition is useful to make a medicament used to induce apoptosis in a cancer cell or a tumor in a subject. The eIF5A1 polynucleotide encodes a truncated eIF5A1 protein preferably comprising the amino acid sequence set forth in SEQ ID NO:37 shown in FIG. 38. In certain embodiments, the eIF5A1 polynucleotide encodes a truncated eIF5A1 protein that is about 16 kDA.

The composition and or the medicament can be administered to mammals, including humans. As used herein, "subject" includes mammals and humans.

Inducing apoptosis can have the following effects in a cancer cell or tumor: slows cancer cell or tumor growth, arrests cancer cell or tumor cell growth, or kills the cancer cell or reduces the tumor size and any combination of the above. Any cancer can be treated and in certain embodiments, the cancer is multiple myeloma.

In certain embodiments the eIF5A1 polynucleotide comprises the sequence set forth in SEQ ID NO:38 (as shown in FIG. 41). In certain embodiments the eIF5A1 polynucleotide is comprised within a plasmid or expression vector. Plasmids and expression vectors are described herein below in more detail. In certain embodiments the expression vector is an adenovirus expression vector or is pHM6. In certain embodiments the expression vector comprise a tissue specific promoter, such as a B cell specific promoter (i.e. B29) when the composition or medicament is used to treat multiple myeloma. The expression vector may comprise a pCpG plasmid. As discussed in more detail hereinbelow, the expression vector may be complexed to polyethylenimine.

The composition or medicament is preferably administered intratumorally, intravenously or subcutaneously.

The present invention also provides an isolated polynucleotide encoding a truncated eIF5A1 protein wherein the polynucleotide comprises the sequence set forth in SEQ ID NO:38 (as shown in FIG. 41).

The invention also provides an isolated polynucleotide encoding a truncated eIF5A1 protein wherein the truncated protein comprises the amino acid sequence set forth in SEQ ID NO:37.

As discussed hereinbelow, the eIF5A1 is formed by caspase-mediated cleavage. Accordingly the present invention further provides an isolated truncated eIF5A1 polypeptide formed by caspase mediated cleavage of eIF5A1.

The present invention further provides a composition or the use of the composition to make a medicament comprising an eIF5A1 polynucleotide that encodes a truncated eIF5A1 protein in combination with a full length eIF5A1 polynucleotide. This composition is useful to make a medicament to induce apoptosis in a cancer cell or tumor in a subject. The eIF5A1 polynucleotide encoding a truncated eIF5A protein is as described above. The full length eIF5A1 polynucleotide encodes a protein comprising the amino acid sequence set forth in SEQ ID NO:35. The full length eIF5A1 polynucleotide is described in more detail below. In certain embodiments, the eIF5A1 polynucleotide comprises the sequence set forth in SEQ ID NO:38 and the full length eIF5A1 polynucleotide comprises sequence set forth SEQ ID NO:43 (as shown in FIG. 53).

The full length and truncated polynucleotides may be present in expression vectors as described herein. Additionally the vectors may comprise the promoters described herein as well as any other useful promoter.

In certain embodiments, the full length eIF5A polynucleotide encodes a mutant eIF5A1, wherein the mutation prevents or inhibits hypusination by deoxyhypusine synthase and/or wherein the mutation is present at the ubiquinization site and/or the acetylation site. The mutants are described in more detail below. In certain embodiments, the mutant is selected from the group consisting of K50A, K50R, K67A, K47R, K67R, K50A/K67A, K50A/K47R, K50A/K67R, K50R/K67A, K50R/K47R, K50R/K67R, and K47A/K67A.

The present invention also provides a composition comprising a polynucleotide encoding a truncated eIF5A, a nucleotide encoding a mutant eIF5A and an siRNA targeted against the 3'UTR of eIF5A. The combination/dual use of a nucleotide encoding a mutant eIF5A and an siRNA targeted against the 3'UTR of eIF5A is described more fully below. The composition is useful to make a medicament to administer to a subject to induce apoptosis in cancer cells or tumors.

In certain preferred embodiments, the siRNA targets the sequence in eIF5A1 of 5'-GCT GGA CTC CTC CTA CAC A-3' (SEQ ID NO: 45). siRNA is dsRNA and one strand of the dsRNA comprises the sequence of 5'-GCU GGA CUC CUC CUA CAC A-3' (SEQ ID NO: 46). In certain embodiments the siRNA is stabilized to prevent degradation in serum.

The full length eIF5A1 polynucleotide and/or the eIF5A polynucleotide encoding the truncated eIF5A1 protein may be present in an expression vector. In certain embodiments, the full length eIF5A1 polynucleotide and/or the eIF5A polynucleotide encoding the truncated eIF5A1 protein and/or the siRNA are complexed to polyethylenimine. The full length eIF5A1 polynucleotide and/or the eIF5A polynucleotide encoding the truncated eIF5A1 protein and/or the siRNA are independently complexed to polyethylenimine.

The present invention also provides a method of inducing apoptosis is a mammalian cancer cell or mammalian tumor by providing to the mammal a composition or medicament described herein, for example comprising a nucleotide encoding a truncated eIF5A1, optionally comprising a nucleotide encoding a full length eIF5A or a a nucleotide encoding a full length mutant eIF5A and optionally comprising an siRNA targeted against the 3'UTR of eIF5A. In certain embodiments the cancer is multiple myeloma and the composition/medicament is administered intravenously, intra peritoneally or intra tumorally.

The present invention also relates to the combinatorial use of an siRNA targeted against an endogenous gene to knock out or knock down expression of the endogenous gene in a subject and a of a polynucleotide encoding the gene in a delivery vehicle/expression vector provided to the subject to provide expression in the host of the protein encoded by the polynucleotide.

This combination is useful in treating a subject with a disease or condition caused by the existence of a faulty or mutant protein, i.e. where the protein produced in the subject is unable to perform it necessary function or alternatively, fowls up a metabolic pathway or biomolecule interaction because of its faulty structure. The siRNA is designed to target the gene encoding the faulty protein, and knock down or knock out expression of that faulty protein. A polynucleotide encoding a normal (non faulty) protein is administered to the subject and is expressed in the subject so that the normal protein is available to perform its necessary function.

In another embodiment, instead of administering the polynucleotide encoding the desired protein, the protein is administered to the subject. The terms protein, peptide and polypeptide are used herein interchangeably.

The siRNA is preferably designed to target a certain region of the gene so it either knocks down or knocks out endogenous expression of the faulty protein but at the same time will not effect exogenous expression of the administered polynucleotide encoding the normal protein. For example, the siRNA may target the 3'UTR so it does not effect exogenous expression of the administered sense construct (the polynucleotide encoding the protein). By knocking down or knocking out endogenous expression of the faulty gene, there will be less or none of the faulty protein to compete with the normal protein expressed from the exogenous polynucleotide.

One example of a disease state where this application would be useful concerns sickle cell anemia. Sickle cell anemia is a blood disorder that affects hemoglobin, the protein found in red blood cells (RBCs) that helps carry oxygen throughout the body.

Sickle cell anemia occurs when a person inherits two abnormal genes (one from each parent) that results in expression of a mutant hemoglobin (Hbs). The mutant hemoglobin causes the RBCs to change shape. Red blood cells with normal hemoglobin (hemoglobin A, or HbA) move easily through the bloodstream, delivering oxygen to all of the cells of the body. They can easily "squeeze" through even very small blood vessels. Sickle cell anemia occurs because the abnormal form of hemoglobin (HbS) tends to clump together, making red blood cells sticky, stiff, and more fragile, and causing them to form into a curved, sickle shape.

Although several hundred HBB gene variants are known, sickle cell anemia is most commonly caused by the hemoglobin variant HbS. In this variant, the hydrophobic amino acid valine takes the place of hydrophilic glutamic acid at the sixth amino acid position of the HBB polypeptide chain. This substitution creates a hydrophobic spot on the outside of the protein structure that sticks to the hydrophobic region of an adjacent hemoglobin molecule's beta chain. This clumping together (polymerization) of HbS molecules into rigid fibers causes the "sickling" of red blood cells.

Polymerization occurs only after red blood cells have released the oxygen molecules that they carry to various tissues throughout the body. Once red blood cells return to the lungs where hemoglobin can bind oxygen, the long fibers of HbS molecules depolymerize or break apart into single molecules. Cycling between polymerization and depolymerization causes red blood cell membranes to become rigid. The rigidity of these red blood cells and their distorted shape when they are not carrying oxygen can result in blockage of small blood vessels. This blockage can cause episodes of pain and can damage organs.

Sickle cell anemia is an autosomal recessive genetic disorder. For the disease to be expressed, a person must inherit either two copies of HbS variant or one copy of HbS and one copy of another variant. Carriers, who have one copy of the normal HBB gene (HbA) and one copy of HbS, are described as having sickle cell trait and do not express disease symptoms.

Thus, one embodiment of the present invention provides a method of treating subjects with sickle cell anemia. siRNA targeted to the HBB gene is administered to the patient. The siRNA is designed to knock down and preferably knock out the expression of the Hbs variant of hemoglobin. A polynucleotide encoding a normal hemoglobin is provided to the subject so the subject expresses a normal hemoglobin. The siRNA is also designed so that it will not interfere with expression of the exogenous polynucleotides encoding the normal hemoglobin. Thus, the subject no longer makes the variant hemoglobin (or makes substantially less) and instead makes normal healthy hemoglobin, resulting in more normal red blood cells, which function normally.

The present invention is also useful in situations where a post translational modification occurs to the protein, which causes or leads to a disease state. siRNA is used to knock down expression of the endogenous protein so none or less is available for the post translational modification. Then, a polynucleotide encoding a protein is provided to the patient for exogenous expression. The protein is modified so that it is unable to be post translationally modified. This protein is then available to the body for its appropriate use, but will not lead to the disease state because it is not able to be post translationally modified. One skilled in the art would understand different post translational modifications. For example, after translation, the posttranslational modification of amino acids extends the range of functions of the protein by attaching to it other biochemical functional groups such as acetate, phosphate, various lipids and carbohydrates, by changing the chemical nature of an amino acid (e.g. citrullination) or by making structural changes, like the formation of disulfide bridges. Also, enzymes may remove amino acids from the amino end of the protein, or cut the peptide chain in the middle. For instance, the peptide hormone insulin is cut twice after disulfide bonds are formed, and a propeptide is removed from the middle of the chain; the resulting protein consists of two polypeptide chains connected by disulfide bonds. Also, most nascent polypeptides start with the amino acid methionine because the "start" codon on mRNA also codes for this amino acid. This amino acid is usually taken off during posttranslational modification. Other modifications, like phosphorylation, are part of common mechanisms for controlling the behavior of a protein, for instance activating or inactivating an enzyme. Another post translational modification includes the hypusination of eukarotic initiation factor 5A (eIF5A) by deoxyhypusine synthase (DHS).

Thus, the invention provides a method of altering expression of a gene in a subject, wherein a polynucleotide encoding a protein is provided to a patient and is expressed in the patient. The protein may be a normal/wild type protein or a mutated protein. Expression of the corresponding endogenous gene is suppressed with the siRNA that is administered to the subject.

The method further comprises providing a construct comprising a polynucleotide encoding the target protein wherein the polynucleotide is expressed in the subject to produce the target protein. In certain embodiments where the endogenous gene expresses a faulty protein, the polynucleotide is designed to encode either a normal/healthy protein. The siRNA is administered to suppress expression of the faulty endogenous protein. In certain embodiments where the endogenous gene expresses a normal healthy protein, the polynucleotide is designed to encode a mutant protein that can not be postranslationally modified as would occur with a normal/healthy or non mutant protein. The siRNA is administered to suppress expression of the endogenous protein so there is less of this protein to be available for posttranslational modification.

In certain embodiments, the siRNA is chosen or designed to target regions of the gene so as to not effect expression of the exogenous polynucleotide. For example, the siRNA may target the 3' UTR or 3' end.

The siRNA may be delivered to the patient as either naked siRNA or naked siRNA stabilized for serum. The siRNA may by either injected systemically, i.e. IP or IV. Alternatively, the siRNA may be injected or delivered locally to the desired area of the body. In certain embodiments, the siRNA may be administered in a delivery vehicle such as but not limited to dendrimers, liposomes, or polymers.

The polynucleotides encoding the desired protein may be administered through any delivery means that provide or allow expression of the nucleotide. The term polynucleotide and nucleotide are used herein interchangeably. Delivery may be through any viral or non-viral mechanism, such as but not limited to plasmids, expression vectors, viral constructs, adenovirus constructs, dendrimers, liposomes, or polymers.

In certain embodiments an expression plasmid having reduced CpG dinucleotides is used to express the polynucleotides. Any promoter capable of promoting expression of the polynucleotide may be used, which may be chosen based on the application desired for the therapy. For example, for killing multiple myeloma, a promoter specific for B cells may be desirable, such as human B29 promoter/enhancer. In other embodiments, the promoter may be another tissue specific promoter, or may be a system promoter.

The polynucleotides encoding the target protein may be delivered through IV or subcutaneous injection or any other biologically suitable delivery mechanism.

Alternatively, the polynucleotides may be delivered in liposomes or any other suitable "carrier" or "vehicle" that provides for delivery of the DNA (or plasmid or expression vector) to the target tumor or cancer cells. See for example, Luo, Dan, et al., Nature Biotechnology, Vol. 18, January 2000, pp. 33-37 for a review of synthetic DNA delivery systems. Thus, it may be preferable to deliver the nucleotides/plasmid/expression vector via a vehicle of nanometer size such as liposomes, dendrimers or a similar non-toxic nanoparticle. The vehicle preferably protects the nucleotides/plasmid/expression vector from premature clearance or from causing an immune response while delivering an effective amount of the nucleotides/plasmid/expression vector to the subject, tumor or cancer cells. Exemplary vehicles may range from a simple nano-particle associated with the nucleotides/plasmid/expression vector to a more complex pegylated vehicle such as a pegylated liposome having a ligand attached to its surface to target a specific cell receptor.

Liposomes and pegylated liposomes are known in the art. In conventional liposomes, the molecules to be delivered (i.e. small drugs, proteins, nucleotides or plasmids) are contained within the central cavity of the liposome. One skilled in the art would appreciate that there are also "stealth," targeted, and cationic liposomes useful for molecule delivery. See for example, Hortobagyi, Gabriel N., et al., J. Clinical Oncology, Vol. 19, Issue 14 (July) 2001:3422-3433 and Yu, Wei, et al., Nucleic Acids Research. 2004, 32(5); e48. Liposomes can be injected intravenously and can be modified to render their surface more hydrophilic (by adding polyethylene glycol ("pegylated") to the bilayer, which increases their circulation time in the bloodstream. These are known as "stealth" liposomes and are especially useful as carriers for hydrophilic (water soluble) anticancer drugs such as doxorubicin and mitoxantrone. To further the specific binding properties of a drug carrying liposome to a target cell, such as a tumor cell, specific molecules such as antibodies, proteins, peptides, etc. may be attached on the liposome surface. For example, antibodies to receptors present on cancer cells may be used to target the liposome to the cancer cell. In the case of targeting multiple myeloma, folate, Il-6 or transferrin for example, may be used to target the liposomes to multiple myeloma cells.

Dendrimers are also known in the art and provide a preferable delivery vehicle. See for example Marjoros, Istvan, J., et al, "PAMAM Dendrimer-Based Multifunctional Conjugate for Cancer Therapy: Synthesis, Characterization, and Functionality," Biomacromolecules, Vol. 7, No. 2, 2006; 572-579, and Majoros, Istvan J., et al., J. Med. Chem., 2005. 48, 5892-5899 for a discussion of dendrimers.

In a preferred embodiment, the delivery vehicle comprises a polyethylenimine nanoparticle. An exemplary polyethylenimine nanoparticle is the in vivo-jetPEI™, currently produced by Polyplus Transfection, Inc. In vivo-jetPEI™ is cationic polymer transfection agent useful as a DNA and siRNA delivery agent. In vivo-jetPEI™ from Polyplus Transfection is a linear polyethylenimine reagent that provides reliable nucleic acid delivery in animals. It is used for gene therapy (Ohana et al., 2004. Gene Ther Mol Bio 8:181-192; Vernejoul et al., 2002. Cancer Research 62:6124-31), RNA interference, (Urbain-Klein et al., 2004. Gene therapy 23:1-6; Grezelinski et al., 2006. Human Gene Therapy 17:751-66), and genetic vaccination (Garzon et al., 2005. Vaccine 23:1384-92). In vivo JET-PEI is currently in use in human clinical trials as a delivery vector for cancer gene therapy (Lemkine et al., 2002. Mol. Cell. Neurosci. 19:165-174).

In vivo-jetPEI™ condenses nucleic acids into roughly 50 nm nanoparticles, which are stable for several hours. As a result of this unique protection mechanism, aggregation of blood cells following injection is reduced compared to other reagents thereby preventing restricted diffusion within a tissue, erythrocyte aggregation and microembolia. These nanoparticles are sufficiently small to diffuse into the tissues and enter the cells by endocytosis. In vivo-jetPEI™ favors nucleic acids release from the endosome and transfer across of the nuclear membrane.

In a preferred embodiment, both the siRNA and a vector/plasmid comprising the polynucleotide are administered to the subject via an in vivo-jetPEI™ complex. The siRNA and the vector/plasmid comprising the polynucleotide may be complexed together via a polymer complex such as polyethylenimine or the in vivo jetPEI™ complex or may separately complexed to a polymer. For instance, where the siRNA and the vector/plasmid comprising the polynucleotide are to be administered separately to the subject (separately in the meaning of time and/or delivery site) it is preferable to have the siRNA and the polynucleotide complexed to a different carrier. Where the administration will occur at the same time and at the same site, it may be preferable to complex the siRNA and the polynucleotide together.

In another embodiment, instead of a plasmid or vector being administered to deliver a polynucleotide that will be expressed in the subject, the protein per se is delivered to the subject. The protein may be either isolated or may be synthetic. One embodiment of the present invention provides a method of treating cancer in a subject, including mammals and humans. Treating cancer includes, but is not limited to inducing apoptosis in cancer cells, killing cancer cells, reducing the number of cancer cells and reducing tumor volume/weight. The method comprises administering a composition comprising eIF5A1 siRNA and a polynucleotide encoding a mutant eIF5A1. The composition and eIF5A1 siRNA and a polynucleotide encoding a mutant eIF5A1 are discussed herein below.

All cells produce eukaryotic initiation factor 5A ("eIF-5A") (or also referred to herein as "factor 5A"). Mammalian cells produce two isoforms of eIF-5A1 (eIF-5A1 and eIF-5A2). eIF-5A1 has been referred to as apoptosis-specific eIF-5A, as it is upregulated in cells undergoing apoptosis. Human eIF-5A1 has the accession number NM 001970 and is shown in FIG. 1. It is believed that eIF-5A1 is responsible for shuttling out of the nucleus subsets of mRNAs encoding proteins necessary for apoptosis. eIF-5A2 has been referred to as proliferation eIF-5A as it is believed to be responsible for shuttling out of the nucleus subsets of mRNAs encoding proteins necessary for cellular proliferation. See Liu & Tartakoff (1997) Supplement to Molecular Biology of the Cell, 8, 426a. Abstract No. 2476, 37th American Society for Cell Biology Annual Meeting, and Rosorius et al. (1999) J. Cell Science, 112, 2369-2380.

Both factor 5As are post translationally modified by deoxyhypusine synthase ("DHS"). DHS hypusinates the eIF-5As. Hypusine, a unique amino acid, is found in all examined eukaryotes and archaebacteria, but not in eubacteria, and eIF-5A is the only known hypusine-containing protein. Park (1988) J. Biol. Chem., 263, 7447-7449; Schumann & Klink (1989) System. Appl. Microbiol., 11, 103-107; Bartig et al. (1990) System. Appl. Microbiol., 13, 112-116; Gordon et al. (1987a) J. Biol. Chem., 262, 16585-16589. Hypusinated eIF-5A is formed in two post-translational steps: the first step is the formation of a deoxyhypusine residue by the transfer of the 4-aminobutyl moiety of spermidine to the α-amino group of a specific lysine of the precursor eIF-5A catalyzed by deoxyhypusine synthase. The second step involves the hydroxylation of this 4-aminobutyl moiety by deoxyhypusine hydroxylase to form hypusine.

The amino acid sequence of eIF-5A is well conserved between species, and there is strict conservation of the amino acid sequence surrounding the hypusine residue in eIF-5A, which suggests that this modification may be important for survival. Park et al. (1993) Biofactors, 4, 95-104. This assumption is further supported by the observation that inactivation of both isoforms of eIF-5A found to date in yeast, or inactivation of the DHS gene, which catalyzes the first step in their activation, blocks cell division. Schnier et al. (1991) Mol. Cell. Biol., 11, 3105-3114; Sasaki et al. (1996) FEBS Lett., 384, 151-154; Park et al. (1998) J. Biol. Chem., 273, 1677-1683. However, depletion of eIF-5A protein in yeast resulted in only a small decrease in total protein synthesis suggesting that eIF-5A may be required for the translation of specific subsets of mRNA's rather than for protein global synthesis. Kang et al. (1993), "Effect of initiation factor eIF-5A depletion on cell proliferation and protein synthesis," in Tuite, M. (ed.), Protein Synthesis and Targeting in Yeast, NATO Series H. The recent finding that ligands binding eIF-5A share highly conserved motifs also supports the importance of eIF-5A. Xu & Chen (2001) J. Biol. Chem., 276, 2555-2561. In addition, the hypusine residue of modified eIF-5A was found to be essential for sequence-specific binding to RNA, and binding did not provide protection from ribonucleases.

The present inventors have shown that when polynucleotides encoding eIF-5A are administered to cells, there is an increase in apoptosis those cells. They have shown that they have been able to push cancer cells into apoptosis by administering eIF-5A1 polynucleotides that are then expressed in the cancer cells. See co-pending application Ser. Nos. 10/200,148; 11/287,460; 11/293,391 and 11/637,835, all of which are incorporated by reference in their entireties.

The present inventors have additionally determined that when cells have a build up of the hypusinated form of factor 5A, the cells enter into a survival mode and do not undergo apoptosis as they normally would over time. Notably, in cancer cells, there is a significant amount of hyspusinated factor 5A and thus, the cells do not enter into apoptosis (and do not die). Thus, to treat cancer by killing the cancer cells (push the cancer cells to enter into the apoptosis pathway), a polynucleotide encoding eIF-5A1 is administered to the subject or to the cancer cells or tumor to provide increased expression of eIF-5A1, which in turn causes apoptosis in the cancer cells and ultimately cell death and tumor shrinkage. However, if one were to only provide polynucleotides encoding the eIF-5A1 protein to up regulate gene expression of eIF-5A1 and not also use siRNA to knock down endogenous expression of eIF-5A1, there is a tug of war: the eIF-5A1 expression directing the cells towards the apoptosis pathway competes with the presence of the hypusinated factor 5A directing the cells towards the cell survival pathway. The present invention eliminates this tug of war and represents an improvement over only increasing expression of eIF-5A1. The polynucleotides administered to the subject or cell are mutated so that the resulting expressed protein can not be hypusinated. In addition endogenous expression of factor 5A is knocked out/down with siRNA targeted against eIF-5A so there is none/less endogenous eIF-5A1 around to by hypusinated. Thus, since there is no (or substantially less) hypusinated eIF-5A in the cells, they are not pushed into survival mode.

The polynucleotide encoding a mutated eIF-5A1 is preferably mutated so that it can not be hypusinated and thus will not be available to drive the cell into survival mode. For example, in one embodiment, the polynucleotide encoding eIF-5A is mutated to so that the lysine (K) at position 50, which is normally hypusinated by DHS, is changed to an alanine (A) (which can not be hypusinated). This mutant is denoted as K50A.

In another embodiment, the lysine at position 67 is changed to an arginine (R). This mutant is denoted as (K67R). In another embodiment the lysine (K) at position 67 is changed to an alanine (A) and is denoted as (K67A). In another embodiment, the lysine (K) at position 50 is changed to an arginine (K50R) and another embodiment provides a mutant where the lysine (K) at position 47 is changed to an arginine (K47R).

In other embodiments, a double mutant is used. One double mutant is where the lysine (K) at position 50 is changed to an arginine (R) and the lysine (K) at position 67 is changed to a arginine (R). This double mutant is referred to as K50R/K67R. This double mutant is similarly unable to be hypusinated but the changes in the amino acids do not alter the 3-D structure of eIF-5A1 as much as the single mutation (K50A). The double mutation thus provides a protein that is very similar in 3-D shape and folding as the wild type and thus is more stable than the single mutant. Being more stable, it exists longer in the body to provide longer therapeutic benefit. Thus, the body will have the factor 5A it needs for normal cell function but it will not be able to hypusinated so the cells do not get locked into the cell survival mode and escape apoptosis.

Another double mutant is where the lysine (K) at position 47 is changed to an arginine (R) and the lysine at position 50 is changed to an arginine (R). This mutant is denoted as (K47R/K50R). The invention provides another double mutant where the lysine (L) at position 50 is changes to an alanine (A) and the lysine at position 67 is changes to an alanine (A). This mutant is denoted as (K50A/K67A).

Because the body needs factor 5A for normal cell survival and healthy cell proliferation, it is preferable not to shut off expression completely in the subject with the siRNA, if the siRNA is delivered systemically. Control of eIF-5A expression can be achieved by either using an siRNA that is not as good at shutting off expression (i.e. shuts down or reduces expression but does not completely shut off expression) or alternatively, or utilizing a dosing and/or treatment regimen to balance expression levels to allow normal growth and functioning of healthy cells but also to push cancerous cells to apoptosis.

Alternatively, one may utilize local delivery of siRNA. If the siRNA is delivered locally to the cancer cell or tumor, then the expression is preferably knocked out. By knocking out expression, there is no factor 5A around that can be hypusinated and thus there is no hypusinated eIF-5A to lock the cells into survival mode. Since the siRNA is delivered locally to the cancer or tumor, there is no need to have eIF-5A available for regular cell growth.

In certain embodiments, the endogenous gene is eIF5A1. siRNA targeted against eIF5A1 is administered to the subject to suppress expression of the endogenous eIF-5A1. In certain embodiments the siRNA comprises SEQ ID NO:1 or SEQ ID NO:2 or is any siRNA targeted against eIF5A1 that will suppress expression of endogenous eIF-5A1. In certain embodiments, the eIF5A1 is human eIF-5A1 (shown in FIG. 1) and the subject is a human. Other siRNAs targeted against human eIF-5A1 are known and disclosed in co-pending application Ser. Nos. 11/134,445; 11/287,460; 11/184,982; 11/293,391; 11/725,520; 11/725,470; 11/637,835. In other embodiments, the subject is a mammal and the eIF5A1 is specific to the mammal. For example, the subject is a dog and the eIF5A1 is canine eIF5A1. In certain embodiments, the siRNA consists essentially of the siRNA construct shown in FIG. 25. For example, the siRNA contains nucleic acids targeted against the eIF5A1 but also contains overhangs such as U or T nucleic acids or also contains tags, such as a his tag (often referred to as HA tag—which is often used in in vitro studies). Molecules or additional nucleic acids attached at either the 5' or 3' end (or even within the consecutive string of nucleic acids shown in FIG. 25, for example) may be included and fall within the "consisting essentially of" as long as the siRNA construct is able to reduce expression of the target gene. Preferably the siRNA targets regions of the eIF5A1 gene so as to not effect expression of the exogenous polynucleotide. For example the eIF5A1 siRNA targets the 3' UTR or the 3' end. The siRNA shown in FIG. 25 an exemplary eIF5A1 siRNA.

The polynucleotide encodes eIF5A1 wherein the polynucleotide is mutated to encode an eIF5A1 variant. The mutated eIF5A1 is designed so that the variant eIF5A1 can not be post translationally modified (can not be hypusinated). Exemplary mutants are discussed herein above.

In the case of cancer involving solid tumors, it may be desirable to deliver the siRNA directly to the tumor. The siRNA may be administered separately with respect to time as well as the delivery site from the polynucleotide or may administered together at the same time and/or at the same delivery site. One skilled in the art would understand that the timing of administration of the siRNA may be necessarily administered when the endogenous protein is being translated and not after it is already made.

Although the present inventors have earlier shown that eIF5A1 is non toxic to normal tissue (see pending application Ser. No. 11/293,391, filed Nov. 28, 2005, which is incorporated herein by reference in its entirety), a delivery complex (as compared to direct administration of the eIF5A polynucleotides/plasmid/expression vector) may be preferred. A preferred delivery system provides an effective amount of eIF5A1 to the subject, tumor or group of cancer cells, as well as preferably provides a targeted delivery to the tumor or group of cancer cells. Thus, in certain embodiments, it is preferable to deliver the eIF5A1 nucleotides/plasmid/expression vector via a vehicle of nanometer size such as liposomes, dendrimers or a similar non-toxic nano-particle such as a polyethylenimine polymer (such as an in vivo JetPEI™ complex).

The eIF5A1 protein may also be delivered directly to the site of the tumor. One skilled in the art would be able to determine the dose and length of treatment regimen for delivery of eIF5A1 protein.

The molecular basis for the induction of apoptosis by eIF5A1 is discussed below.

Death Receptor Signaling

Treatment of cancer cells with Ad-eIF5A1 (adenovirus with a wild type eIF5A1) or Ad-eIF5A1(K50A) induces activation of caspase 8, which is initiated by death receptor-ligand binding, and caspase 3, the executioner caspase. These are likely to be indirect effects of eIF5A1, and the fact that caspase 8 and caspase 3 are also activated following treatment with eIF5A1(K50A), which cannot be hypusinated, indicates that the effect is attributable to lysine$_{50}$ eIF5A1. Treatment with Ad-eIF5A1 also appears to result in up-regulation of death receptors as shown previously with upregulation of TNFR1.

Mitochondrial Pathway

Direct or indirect involvement of lysine$_{50}$ eIF5A1 in the mitochondrial pathway for apoptosis is supported by a number of observations including the finding that caspase 9 is activated by treatment of cancer cells with either eIF5A1 or eIF5A1(K50A). As well, p53, which plays a role in activation of the mitochondrial apoptotic pathway, appears to be regulated by eIF5A1. For example, treatment of cancer cells with Actinomycin D up-regulates p53, and this up-regulation of p53 is inhibited by eIF5A1 siRNA. Consistent with this, treatment of cancer cells with Ad-eIF5A1 up-regulates p53 mRNA. Treatment of cancer cells with eIF5A1 also induces migration of Bax from the cytosol to mitochondria, ensuring loss of mitochondrial membrane potential and release of cytochrome C from the intra-mitochondrial space into the cytosol. In addition, this treatment results in up-regulation of cleaved Bcl2, Bim and spliced Bim, which are all pro-apoptotic.

MAPK Signaling

In addition, the present inventors have obtained evidence for the involvement of eIF5A1 in MAPK signaling related to apoptosis. For example, treatment of cancer cells with Ad-eIF5A1 up-regulated P-JNK, which in turn inhibits anti-apoptotic Bcl2. In addition Ad-eIF5A1 and Ad-eIF5A1 (K50A) both induce the formation of P-p38, which can in turn initiate apoptosis by impacting a variety of pro-apoptotic agents including TNFR1 & TNF; FAS & FASL; caspase 8; Bid; Cytochrome C and Capase 3.

NE-κB Signaling

There is evidence that NF-κB signaling supports myeloma growth. For example, myeloma cell adhesion to bone marrow stromal cells induces NF-κB-dependent transcriptional up-regulation of IL-6, which is both a growth and anti-apoptotic factor in multiple myeoloma [Chauhan et al. (1996) Blood 87, 1104.] In addition, TNF-α secreted by myeloma cells activates NF-κB in bone marrow stromal cells, thereby up-regulating IL-6 transcription and secretion. TNF-α also activates NF-κB in myeloma cells resulting in up-regulation of the intracellular adhesion molecule-1 (ICAM-1; CD54) and the vascular cell adhesion molecule-1 (VCAM-1; CD106) on both myeloma cells and bone marrow stromal cells [Hideshima et al. (2001) Oncogene 20, 4519]. This in turn enhances the association of myeloma cells with bone marrow stromal cells [Hideshima et al. (2001) Oncogene 20, 4519]. Conversely, these effects are inhibited by blocking TNFα-induced NF-κB activation [Hideshima et al. (2001) Oncogene 20, 4519]. Indeed, it seems likely that NF-κB mediates protection against TNFα-induced apoptosis in myeloma cells [Hideshima et al. (2002) JBC 277, 16639]. These and other observations have prompted the view that NF-kB signaling may be an attractive target for multiple myeloma therapies.

The inventors have shown that eIF5A1 siRNA inhibits both the activation of NF-κB and the formation of ICAM-1 in human myeloma cells. These observations indicate that eIF5A1 plays a role in NF-κB activation, and inasmuch as the ensuing effects of NF-κB activation are pro-survival in nature, we predict that this activation is mediated, directly or indirectly, by hypusinated eIF5A1.

IL-1

Over-production of the pro-inflammatory cytokine, IL-1, by myeloma cells is a characteristic feature of multiple myeloma that leads to deterioration of bone tissue. eIF5A1 siRNA has been shown to dramatically reduce the overproduction of IL-1 induced by an LPS challenge in mice.

One embodiment of the present invention provides a method of treating multiple myeloma. Multiple myeloma ("MM") is a progressive and fatal disease characterized by the expansion of malignant plasma cells in the bone marrow and by the presence of osteolytic lesions. Multiple myeloma is an incurable but treatable cancer of the plasma cell. Plasma cells are an important part of the immune system, producing immunoglobulins (antibodies) that help fight infection and disease. Multiple myeloma is characterized by excessive numbers of abnormal plasma cells in the bone marrow and overproduction of intact monoclonal immunoglobulins (IgG, IgA, IgD, or IgE; "M-proteins") or Bence-Jones protein (free monoclonal light chains). Hypocalcaemia, anemia, renal damage, increased susceptibility to bacterial infection, and impaired production of normal immunoglobulin are common clinical manifestations of multiple myeloma. Multiple myeloma is often also characterized by diffuse osteoporosis, usually in the pelvis, spine, ribs, and skull.

The present invention seems to be well suited to treat multiple myeloma because of the stimulation feedback loop found in multiple myeloma. For instance, multiple myeloma produces Il-1 in low concentrations in bone marrow. The Il-1 in turn stimulates stromal cells to produce IL-6, which then goes onto stimulate growth of the multiple myeloma. The inventors have previously shown (see pending application Ser. Nos. 11/725,539 and 11/184,982) that siRNA directed against eIF-5A1 was able to inhibit expression of proinflammatory cytokines, such as Il-1; TNF-α, and Il-8). Thus, the siRNA would not only knock down expression of eIF-5A so less is available for hypusination, it would also cut off or decrease the Il-1/Il-6 feedback loop.

An siRNA targeting human eIF5A was used to suppress levels of endogenous hypusinated eIF5A in tumors, while an RNAi-resistant plasmid expressing a mutant of eIF5A (eIF5A$^{K50R}$), that is incapable of being hypusinated, was used to raise the levels of unmodified eIF5A in vivo. Intra-tumoral injection of PEI nanocomplexes containing eIF5A siRNA inhibited MM tumor growth by more than 80% (* p=0.0003) versus complexes containing a control siRNA, indicating that suppressing levels of hypusinated eIF5A has an anti-tumoral effect. PEI complexes containing an eIF5A$^{K50R}$ expression plasmid had a similar effect and inhibited tumor growth by more than 70% (=p 0.001) versus complexes containing a control plasmid. Thus, MM tumor growth can be inhibited either by suppression of the growth-promoting hypusinated eIF5A or by increasing levels of the pro-apoptotic unhypusinated form of eIF5A. Intra-tumoral delivery of complexes containing both eIF5A siRNA and RNAi-resistant eIF5A$^{K50R}$ plasmid had a synergistic effect on tumor growth and resulted in significant tumor shrinkage, inhibiting tumor growth by 94% (* p=0.0002). Intravenous delivery of eIF5A siRNA/eIF5A$^{K50R}$ PEI complexes also efficiently reduced tumor growth by 95% ( p=0.002) indicating systemic delivery of the therapeutic is feasible.

Both local and systemic delivery of eIF5A siRNA/ eIF5A$^{K50R}$ pDNA PEI complexes resulted in a significant anti-tumoral response in multiple myeloma.

The present invention further provides a composition useful in the treatment of cancer, including multiple myeloma. In a preferred embodiment, the composition is a complex of a plasmid DNA encoding point-mutated eIF5A1 that cannot be hypusinated and eIF5A1 siRNA that selectively suppresses endogenous human eIF5A1 but has no effect on the point-mutated eIF5A1 encoded by the plasmid. eIF5A1 siRNAs and polynucleotides encoding mutant eIF5A1 are discussed above. The plasmid DNA and the siRNA are both preferably complexed to PEI (polyethylenimine) nanoparticles. They may be complexed separately and administered separately or together or they may be complexed together. The DNA and the RNA bind to positively charged amino groups on the PEI and are released when the nanoparticles are taken up into cells. It has been demonstrated that PEI-nucleic acid complexes are effectively taken up into both dividing and non-dividing cells.

The plasmid DNA preferably encodes eIF5A1(K50R) which, like eIF5A1(K50A), cannot be hypusinated and, accordingly, is strongly apoptogenic. The expression of eIF5A1(K50R) is preferably regulated by a B-cell-specific promoter.

The eIF5A1 siRNA is preferably specific to the 3'-end of endogenous human eIF5A1 and has no effect on expression of the trans eIF5A1(K50R). An exemplary preferred eIF5A1 siRNA comprises, consists essentially of or consists of the siRNA shown in FIG. 25. The rationale for including the eIF5A1 siRNA is: (1) to deplete endogenous eIF5A1, which is almost all hypusinated and hence in the pro-survival form; (2) to inhibit activation of NF-κB, and thereby reduce the production of IL-6 and the formation of intracellular adhesion molecules; and (3) to inhibit the formation of IL-1. That eIF5A1 siRNA acts synergistically with eIF5A1(K50R) to induce apoptosis in myeloma cells. Inasmuch as (2) and (3) above are pro-survival events, they are likely mediated by hypusinated eIF5A1, and hence not affected by eIF5A1 (K50R) which cannot by hypusinated. This approach results in a larger pool of unhypusinated eIF5A leading to apoptosis of cancer cells, including multiple myeloma cells, with little effect on healthy cells.

A preferred composition is referred to herein as SNS01. SNS0I is a complex containing both, an RNAi-resistant plasmid DNA encoding eIF5A$^{K50R}$ driven by a promoter that restricts expression to cells of B-cell origin (including myeloma cells) for enhanced safety, and an siRNA targeting human eIF5A with dTdT 3' overhangs for enhanced nuclease resistance and which the siRNA and the plasmid are complexed to in vivo JetPEI™.

EXAMPLES

Example 1

Transfection of HeLaS3 Cells with Wild Type and Variants of eIF-5A1

Figure 2A:
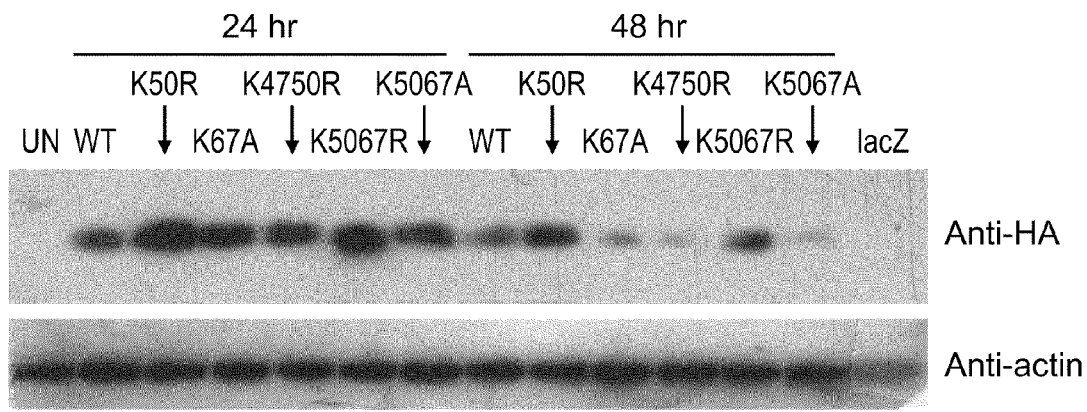
FIG. 2 shows that mutation of eIF-5A at K50 and K67 increases accumulation of transfected protein. See example 1.
Figure 2B:
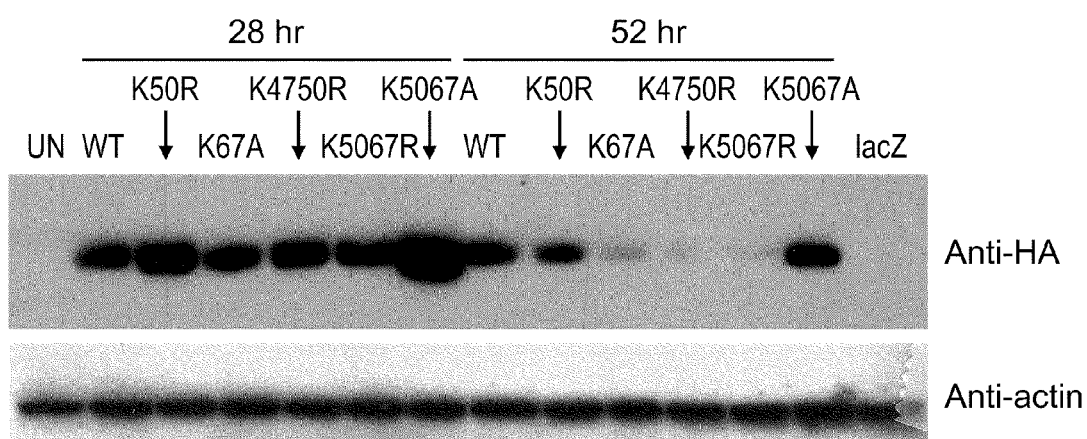

HeLa S3 cells were transfected using Lipofectamine 2000 with plasmids expressing HA-tagged eIF5A1 variants including wild-type eIF5A1 (WT), eIF5A1K50R (K50R), eIF5A1K67R (K67R), eIF5A1K67A (K67A), eIF5A1K47R/ K50R (K4750R), eIF5A1K50R/K67R (K5067R), or eIF5A1K50A/K67A (K5067A). A plasmid expressing LacZ was used as a control. At 24 and 48 hours (A) or 28 and 52 hours (B) after transfection, the cell lysate was harvested and fractionated by SDS-PAGE. Expression levels of transfected eIF5A1 was detected using an antibody against HA. Result: Mutation of eIF5A1 at a lysine in the putative ubiquination site (K67R) increased the accumulation of the eIF5A1 transgene above wild-type (A). Mutation of eIF5A1 at the lysine required for hypusination (K50R) also increased accumulation of eIF5A1 transgene above wild-type eIF5A1 (B). A double mutant form of eIF5A1 (K50A/K67A) was expressed particularly well when compared to the unmutated wild-type eIF5A1 transgene (A+B). See FIG. 2.

Example 2

Transfection of KAS Cells with Wild Type and Variants of eIF-5A1

Figure 3:
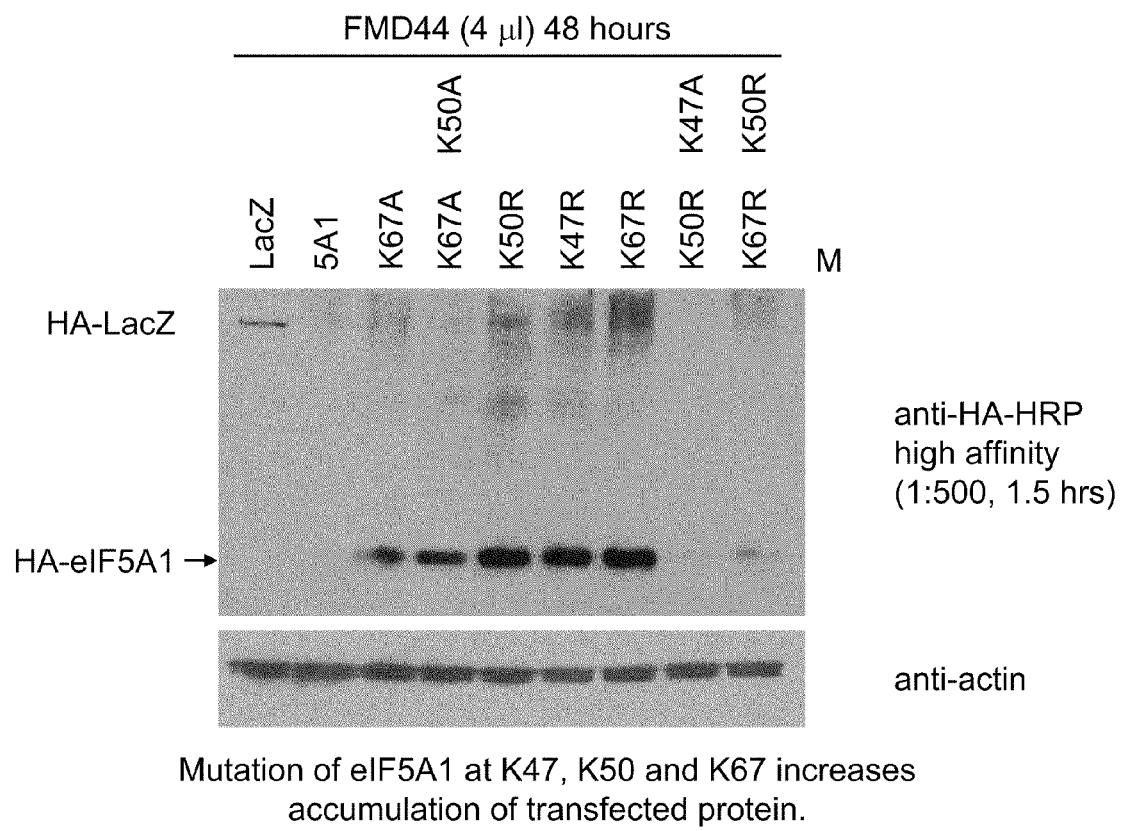
FIG. 3 shows that mutation of eIF5A1 at K47, K50 and K67 increases accumulation of transfected protein. See example 2.

KAS cells were transfected using PAMAM dendrimer (FMD44) with plasmids expressing HA-tagged eIF5A1 variants including wild-type eIF5A1 (5A1), eIF5A1K67A (K67A), eIF5A1K50A/K67A (K50A K67A), eIF5A1K50R (K50R), eIF5A1K47R (K47R), eIF5A1K67R (K67R), eIF5A1K47R/K50R (K47R K50R), or eIF5A1K50R/K67R (K50R K67R). A plasmid expressing LacZ was used as a control. 48 hours (after transfection, the cell lysate was harvested and fractionated by SDS-PAGE. Expression levels of transfected eIF5A1 was detected using an antibody against HA. Equal loading was verified using an antibody against actin. Result: Mutation of eIF5A1 at a lysine in the putative ubiquination site (K67A or K67R) increased the accumulation of the eIF5A1 transgene above wild-type. Mutation of eIF5A1 at the lysine required for hypusination (K50R) or at an acetylation site (K47R) also increased accumulation of eIF5A1 transgene above wild-type eIF5A. A double mutant form of eIF5A1 (K50A/K67A) was also expressed at higher levels when compared to the unmutated wild-type eIF5A1 transgene. See FIG. 3.

Example 3

Transfection of KAS Cells Using PAMAM Dendrimer

Figure 4:
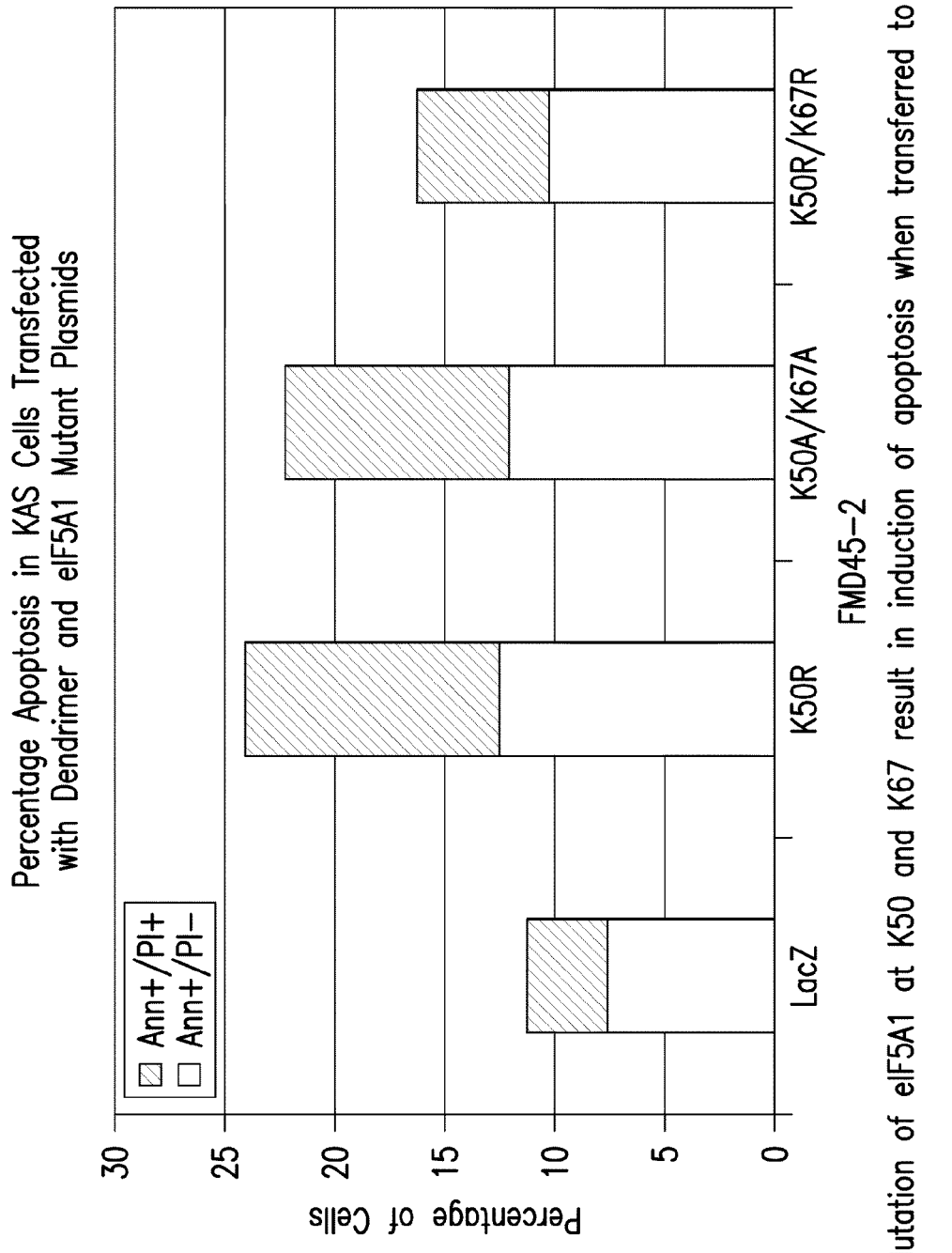
FIG. 4 shows that mutation of eIF5A1 at K50 and K67 results in induction of apoptosis when transfected into KAS cells. See example 3.

KAS cells were transfected using PAMAM dendrimer (FMD45-2) with plasmids expressing HA-tagged eIF5A1 variants including eIF5A1K50R (K50R), eIF5A1K50A/K67A (K50A/K67A), or eIF5A1K50R/K67R (K50R K67R). A plasmid expressing LacZ was used as a control. Seventy-two hours after transfection, the cells were stained with Annexin/PI and analyzed by FACS. Cells that stained positively for Annexin V and negatively for PI (propidium iodide) were considered to be in the early stages of apoptosis (Ann+/PI−) and cells that stained positively for both Annexin V and PI were considered to be in the late stages of apoptosis (Ann+/PI+). Result: Mutation of eIF5A1 at a lysine in the hypusination site (K50R) or in the putative ubiquination site (K67R), as well as the double mutant (K50A/K67A) resulted in apoptosis of KAS cells significantly above the levels of the LacZ control. See FIG. 4.

Example 4

Transfection of KAS Cells with Plasmids Expressing eIF-5A1 and eIF-5A1 Variants

Figure 5:
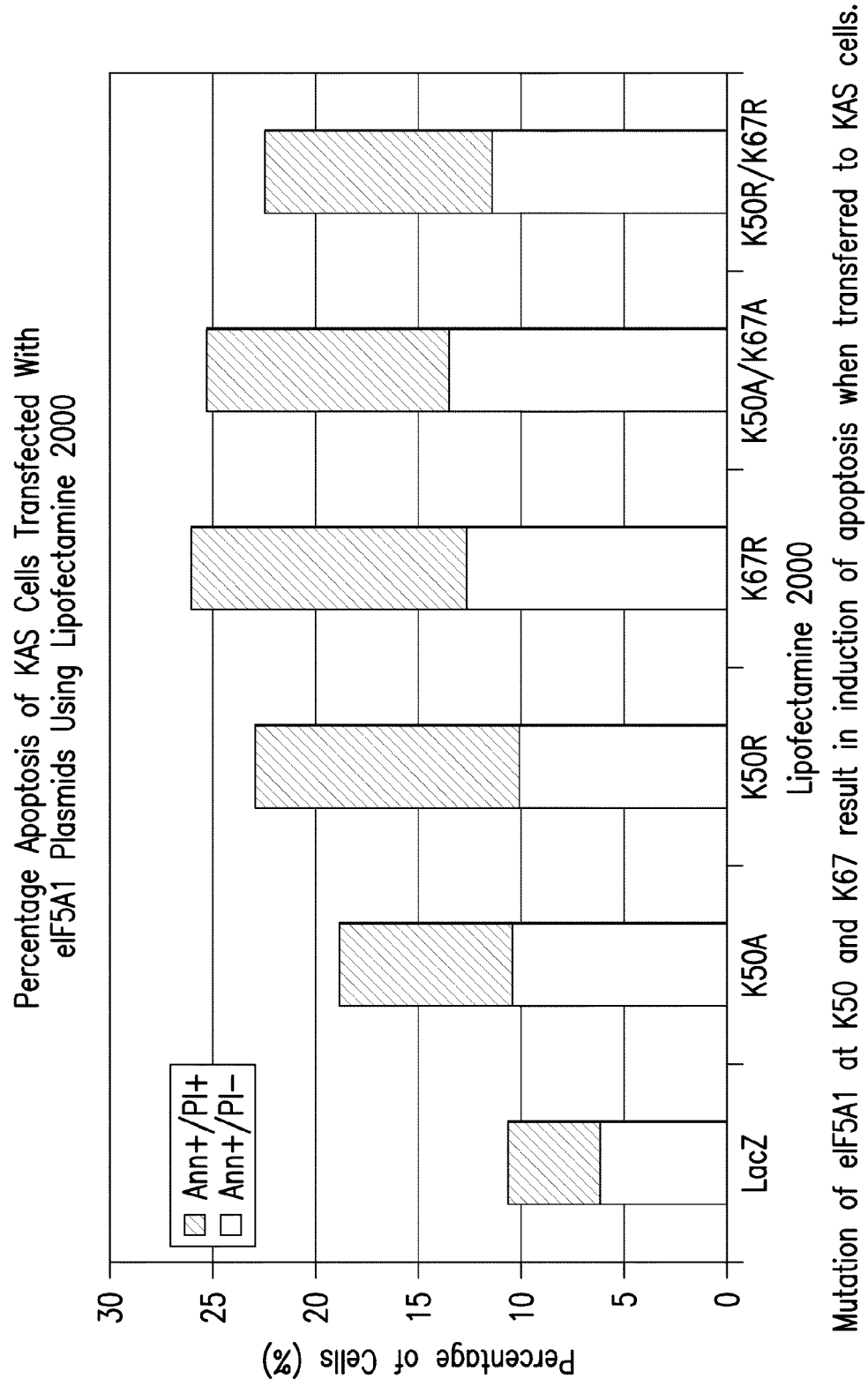
FIG. 5 shows that mutation of eIF5A1 at K50 and K67 results in induction of apoptosis when transfected into KAS cells. See example 4.

KAS cells were transfected using Lipofectamine 2000 with plasmids expressing HA-tagged eIF5A1 variants including eIF5A1K50A (K50A), eIF5A1K50R (K50R), eIF5A1K67R (K67R), eIF5A1K50A/K67A (K50A/K67A), or eIF5A1K50R/K67R (K50R K67R). A plasmid expressing LacZ was used as a control. Seventy-two hours after transfection, the cells were stained with Annexin/PI and analyzed by FACS. Cells that stained positively for Annexin V and negatively for PI (propidium iodide) were considered to be in the early stages of apoptosis (Ann+/PI−) and cells that stained positively for both Annexin V and PI were considered to be in the late stages of apoptosis (Ann+/PI+). Result: Mutation of eIF5A1 at a lysine in the hypusination site (K50R) or In the putative ubiquination site (K67R), as well as the double mutant (K50A/K67A) resulted in apoptosis of KAS cells significantly above the levels of the LacZ control. See FIG. 5.

Example 5

The Use of Mutated eIF-5A1 to Treat KAS Cells Results in Apoptosis

Figure 6:
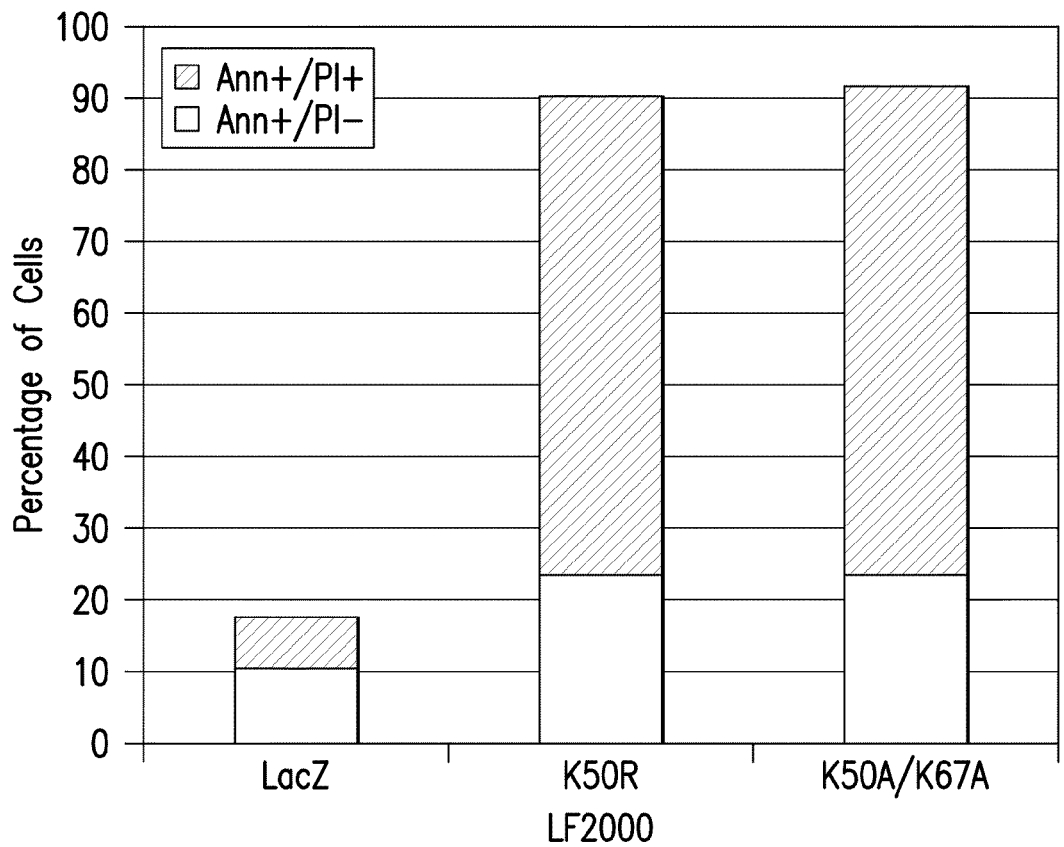
FIG. 6 shows that mutation of eIF5A1 at K50 and K67 results in induction of apoptosis when transfected into KAS cells. See example 5.
Figure 7B:
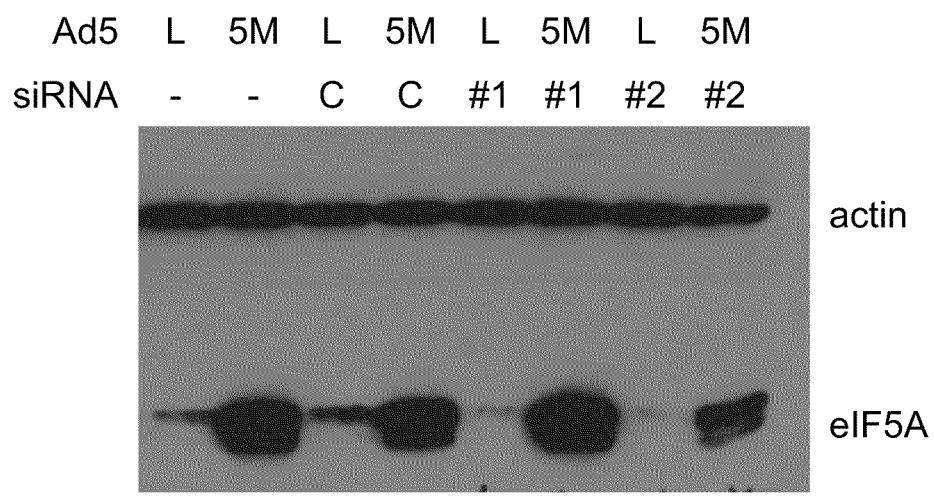
FIG. 7B shows that pre-treatment with eIF5A1 siRNA (against target #1 (SEQ ID NO:1)) (the sequence of the siRNA construct shown in FIG. 25 reduced expression of endogenous eIF5A1 but allows accumulation of RNAi-resistant eIF5A1$^{k50A}$ expressed by adenovirus. See example 6B.
Figure 7C:
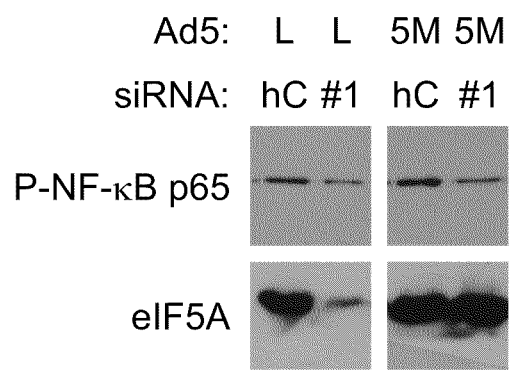
FIG. 7C shows that pre-treatment with eIF5A1 siRNA against target #1 prior to adenovirus infection reduces expression of phosphorylated NF-κB in human multiple myeloma cells. See example 6C.
Figure 7D:
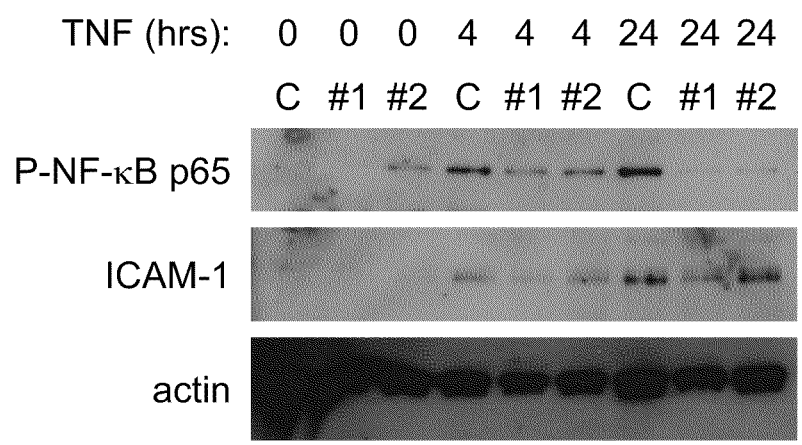
FIG. 7D shows that pre-treatment with eIF5A1 siRNA against target #1 prior to Adenovirus infection reduces expression of phosphorylated NF-kB and ICAM-1 in human multiple myeloma cells. See example 6D.
Figure 7E:
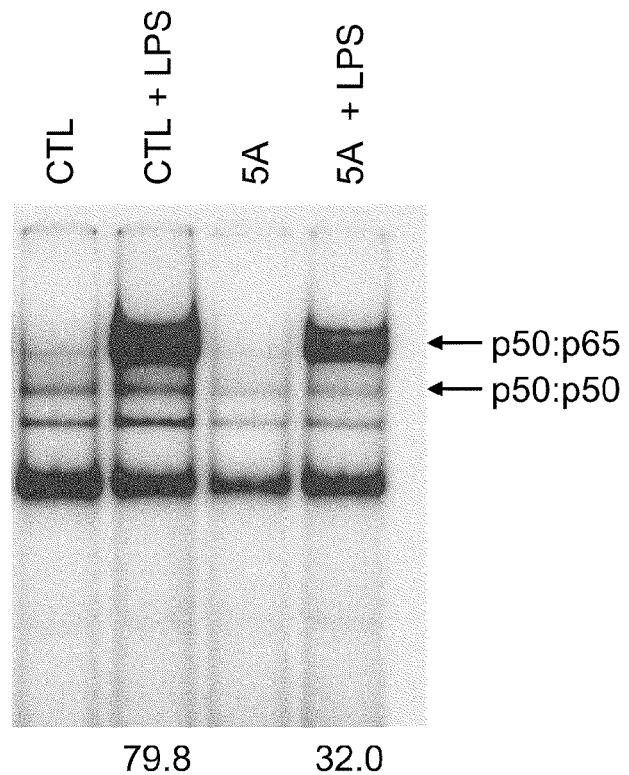
FIG. 7E shows that siRNA-mediated suppression of eIF5A in human multiple myeloma cells inhibits LPS-mediated induction of NFkB DNA-Binding Activity. The inhibition of NFkB activity by eIF5A siRNA could explain it's ability to increase apoptosis induction when combined with over-expression of eIF5A$^{K50R}$ since NF-kB regulates many pro-survival and anti-apoptosis pathways.
Figure 7F:
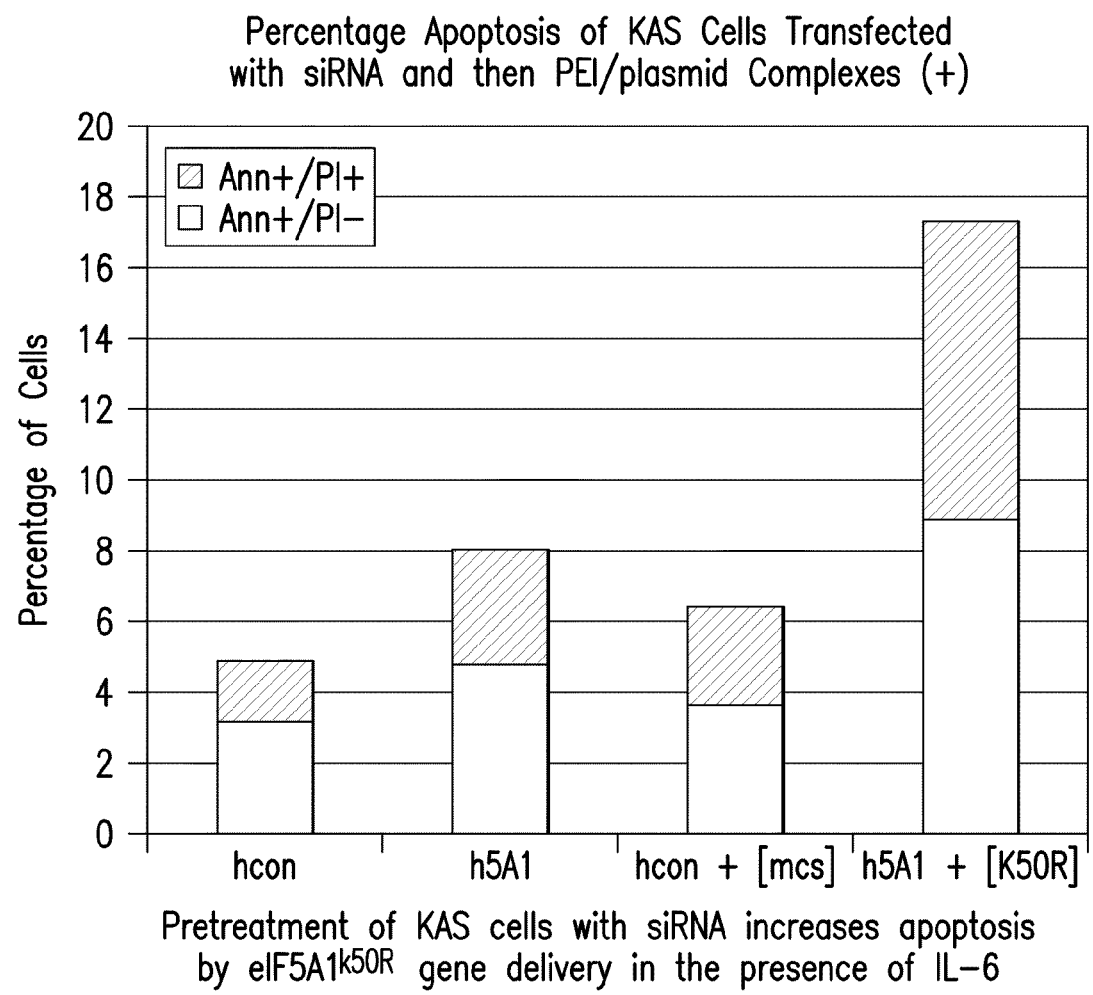
FIG. 7F shows that pretreatment of KAS cells with siRNA increases apoptosis by eIF5A1$^{k50R}$ gene delivery in the presence of IL-6. See example 6E.

KAS cells were transfected using Lipofectamine 2000 with plasmids expressing HA-tagged eIF5A1 variants eIF5A1K50R (K50R) or eIF5A1K50A/K67A (K50A/K67A). A plasmid expressing LacZ was used as a control. Seventy-two hours after transfection, the cells were stained with Annexin/PI and analyzed by FACS. Cells that stained positively for Annexin V and negatively for PI (propidium iodide) were considered to be in the early stages of apoptosis (Ann+/PI−) and cells that stained positively for both Annexin V and PI were considered to be in the late stages of apoptosis (Ann+/PI+). Result: Mutation of eIF5A1 at a lysine in the hypusination site (K50R) or mutation of eIF5A1 at both the hypusination site and in the putative ubiquination site (K50A/K67A) resulted in apoptosis of KAS cells significantly above the levels of the LacZ control. See FIG. 6.

Example 6A siRNA/Adenovirus-Mediated Killing of Multiple Myeloma Cells

KAS (human multiple myeloma) cells were maintained in S10 media [RPMI 1640 with 4 ng/ml IL-6, 10% fetal bovine serum (FBS), and penicillin/streptomycin (P/S)]. KAS cells were transfected with 58.7 pmoles of siRNA using Lipofectamine 2000 (Invitrogen). Mock transfected cells were treated with Lipofectamine 2000 in the absence of siRNA. Transfection was conducted in the antibiotic-free S10 media.
 a) siRNAs targeting human eIF5A1:
  eIF5A1 siRNA target #1 (the siRNA targets this region of human eIF5A1: 5'-AAGCTGGACTCCTCCTACACA-3' (SEQ ID NO: 1). The siRNA sequence is shown in FIG. 25 and is often referred to herein as h5A1.
  eIF5A1 siRNA target #2 eIF5A1 (this siRNA targets this region of human eIF5A1: 5'-AAAGGAATGACTTCCAGCTGA-3' (SEQ ID NO: 2). (The siRNA sequence is often referred to herein ash5A1-ALT)
 b) control siRNA: The control siRNA had the following sequence: sense strand, 5'-ACACAUCCUCCUCAG-GUCGdTdT-3' (SEQ ID NO: 3); and antisense strand, 3'-dT-dTUGUGUAGGAGGAGUCCAGC-5' (SEQ ID NO: 4).

Other controls that have been used include non-targeting validated siRNAs from Dharmacon since they have been micro-array tested to limit unwanted off-targeting effects. For example, for in vitro work studying NFkB, the control used was Dharmacon's non-targeting siRNA's (sequence D-001700-01) and for in vivo work, the control used was Dharmacon's (sequence D-001810-01).

Four hours after transfection, the cells were pelleted and resuspended in 1 ml of S10 media. Seventy-two hours after the initial siRNA transfection, the transfected KAS cells were counted and seeded at 300,000 cells/well in a 24-well plate and transfected with the same siRNA a second time.

Four hours after transfection, the cells were pelleted and resuspended in 1 ml of S10 media (without IL-6) containing 3000 ifu of either Ad-LacZ (Adenovirus expressing-galactosidase) or Ad-5A1M (Adenovirus expressing human eIF5A1$^{K50A}$).

Seventy-two hours later the cells were harvested and analyzed for apoptosis by staining with Annexin V-FITC and PI (BD Bioscience) followed by FACS analysis.
 a) early apoptosis was defined as cells that were positively stained with Annexin-FITC and negative for PI-staining (Ann+/PI−)
 b) total apoptosis was defined as the total of cells either in early apoptosis (Ann+/PI−) or late apoptosis/necrosis (Ann+/PI+)

The 5A1 siRNA targeting #1 targets the 3'UTR of human eIF5A1 and therefore will not affect expression of eIF5A1 from adenovirus. 5A1 siRNA targeting #2 targets within the open reading frame of human eIF5A1 and so it could potentially interfere with expression of eIF5A1 from the adenovirus.

Results: Cells treated with siRNA and infected with adenovirus expressing the eIF-5A1 K50A variant undergo apoptosis in greater numbers than non-treated cells and cells treated only with siRNA. See FIG. 7.

Example 6B

Pre-Treatment with eIF5A1 siRNA Against eIF5A1 target #1 (Shown in FIG. 25), Reduced Expression of Endogenous eIF5A1 but Allows Accumulation of RNAi-Resistant eIF5A1$^{K50A}$ Expressed by Adenovirus KAS cells were transfected using Lipofectamine 2000 with either a control siRNA (C) or one of two siRNAs targeting eIF5A1 (#1 and #2). The eIF5A1 siRNA #1 targets the 3'UTR of eIF5A1 and therefore does not interfere with expression of eIF5A1 from adenovirus since it contains only the open reading frame of eIF5A1. The sequence of the siRNA is shown in FIG. 25. The eIF5A1 #2 siRNA targets the open reading frame of eIF5A1 and will therefore affect expression of both endogenous and exogenously-expressed eIF5A1. Seventy-two hours after the initial transfection hours the cells were transfected with the same siRNA a second time. Four hours later the transfection complexes were removed from the cells and replaced with growth media (−) IL6 containing either Ad-LacZ (L) or Ad-eIF5A1$^{K50A}$ (5M). Seventy-two hours later the cell lysate was harvested and analyzed by Western blot using antibodies against eIF5A and actin. See FIG. 7B. Accumulation of virally expressed eIF5A1 can be observed (lane 1 vs lane 2) and reduction of eIF5A expression by eIF5A1 siRNAs targeting #1 and #2 can be clearly seen (lanes 5 and 7 vs lane 3). As expected, the eIF5A1 siRNA #1 does not affect accumulation of the virally expressed eIF5A1$^{K50A}$ (lane 6 vs lane 4) while the eIF5A1 siRNA #2 only moderately affects expression of the virally-expressed transgene (lane 8 vs lane 4).

Example 6C

Pre-Treatment with eIF5A1 siRNA Against Target #1 Prior to Adenovirus Infection Reduces Expression of Phosphorylated NF-κB in Human Multiple Myeloma Cells KAS cells were transfected using Lipofectamine 2000 with either a control siRNA (hC) or an siRNA targeting eIF5A1 (#1). The eIF5A1 siRNA #1 targets the 3'UTR of eIF5A1 and will therefore not interfere with expression of eIF5A1 from adenovirus since it contains only the open reading frame of eIF5A1. Seventy-two hours after the initial transfection hours the cells were transfected with the same siRNA a second time. Four hours later the transfection complexes were removed from the cells and replaced with growth media (+) IL6 containing either Ad-LacZ (L) or Ad-eIF5A1$^{K50A}$ (5M). Twenty-four hours later the cell lysate was harvested and analyzed by Western blot using antibodies against phospho-NF-kB p65 (Ser 536) and eIF5A. As expected, the eIF5A1 siRNA #1 does not affect accumulation of the virally expressed eIF5A1$^{K50A}$. Phosphorylation of NF-kB p65 at serine 536 regulates activation, nuclear localization, protein-protein interactions, and transcriptional activity. See FIG. 7C.

Example 6D

Pre-Treatment with eIF5A1 siRNA #1 Prior to Adenovirus Infection Reduces Expression of Phosphorylated NF-kB and ICAM-1 in Human Multiple Myeloma Cells KAS cells were transfected using Lipofectamine 2000 with either a control siRNA (C) or one of two siRNAs targeting eIF5A1 (#1 and #2). Seventy-two hours after the initial transfection hours the cells were transfected with the same siRNA a second time. Four hours later the transfection complexes were removed from the cells and replaced with growth media (+) IL6. Twenty-four hours after the second transfection, the cells were stimulated with 40 ng/ml TNF-α and cell lysate was harvested at 0, 4, or 24 hours and analyzed by Western blot using antibodies against phospho-NF-kB p65 (Ser 536), ICAM-1 and actin. A reduction in TNF-α induced NF-kB p65 phosphorylation (ser 536) and ICAM-1 expression was observed following transfection with both eIF5A1-specific siRNAs. Phosphorylation of NF-kB p65 at serine 536 regulates activation, nuclear localization, protein-protein interactions, and transcriptional activity. ICAM-1 is an inter-cellular adhesion surface glycoprotein that is believed to be involved in the pathogenesis of multiple myeloma. See FIG. 7D.

Example 6E

Pretreatment of KAS Cells with siRNA Increases Apoptosis by eIF5A1$^{k50R}$ Gene Delivery in the Presence of IL-6

KAS cells were transfected with either control siRNA (hcon) or human eIF5A1 siRNA (h5A1) using Lipofectamine 2000. Seventy-two hours later the cells were re-transfected with siRNA. PEI complexes of empty vector (mcs) or eIF5A1$^{k50R}$ (K50R) plasmids were added to the cells four hours later following removal of siRNA transfection medium. The growth medium used throughout the study contained IL-6. Apoptosis was measured seventy-two hours later by staining the cells with Annexin/PI and FACS analysis. See FIG. 7F.

Example 7

Figure 8:
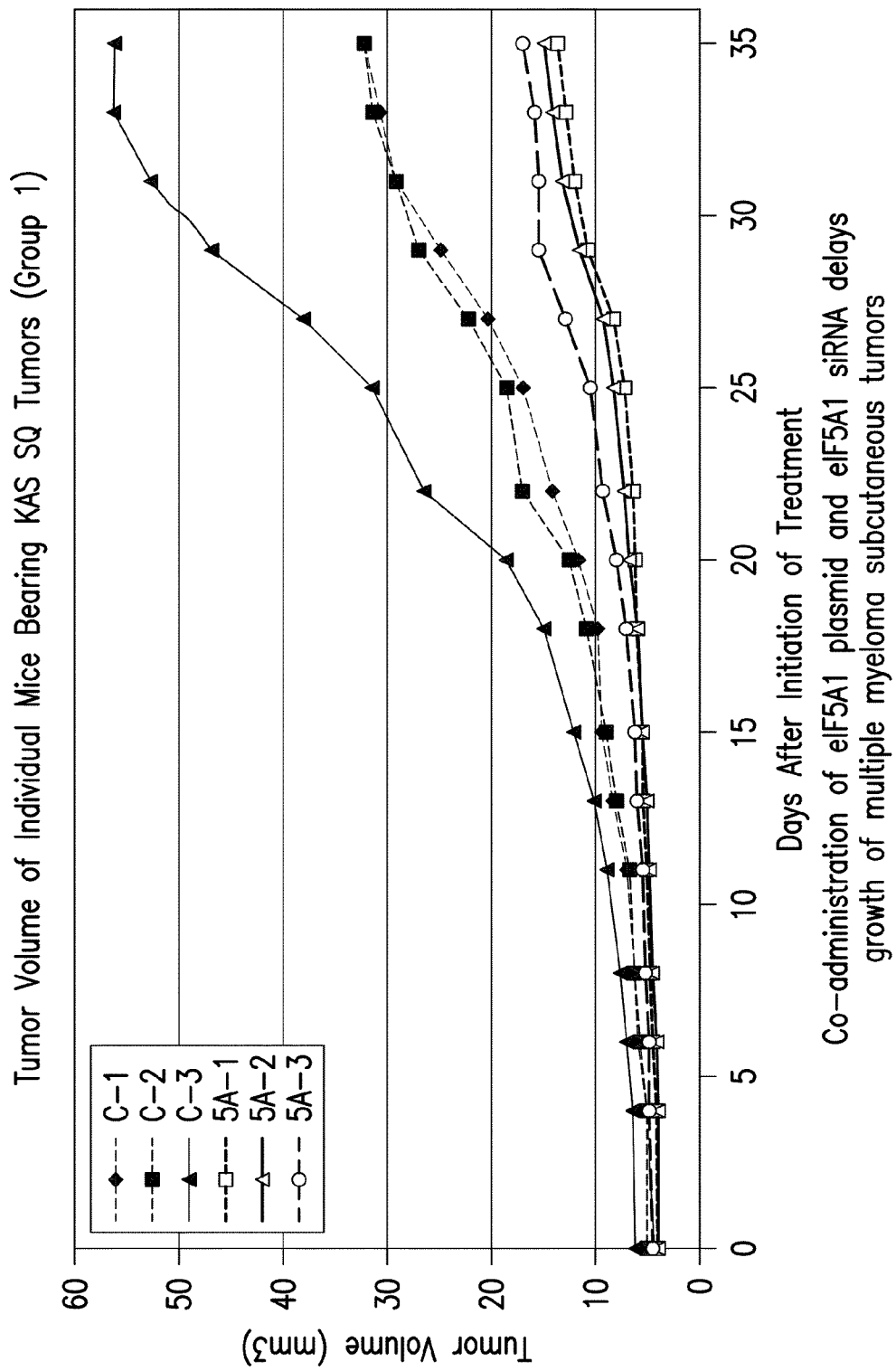
FIG. 8 shows that co-administration of eIF5A1 plasmid and eIF5A1 siRNA delays growth of multiple myeloma subcutaneous tumors. The data shown is the tumor volume for all the mice in each group. See example 7.
Figure 9:
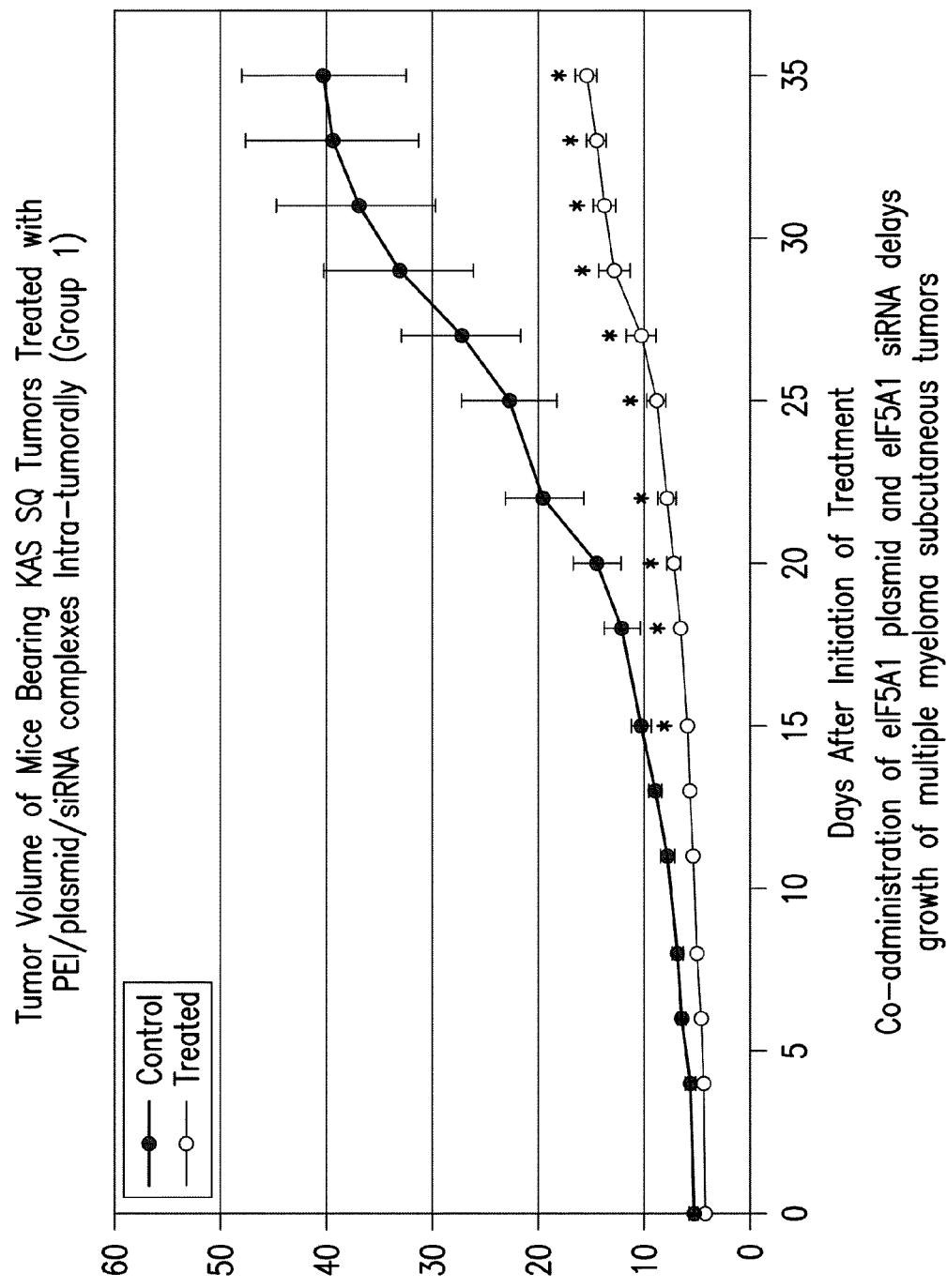
FIG. 9 shows that co-administration of eIF5A1 plasmid and eIF5A1 siRNA delays growth of multiple myeloma subcutaneous tumors. The data shown is the average tumor volume per group+/−standard error. See example 7.
Figure 10:
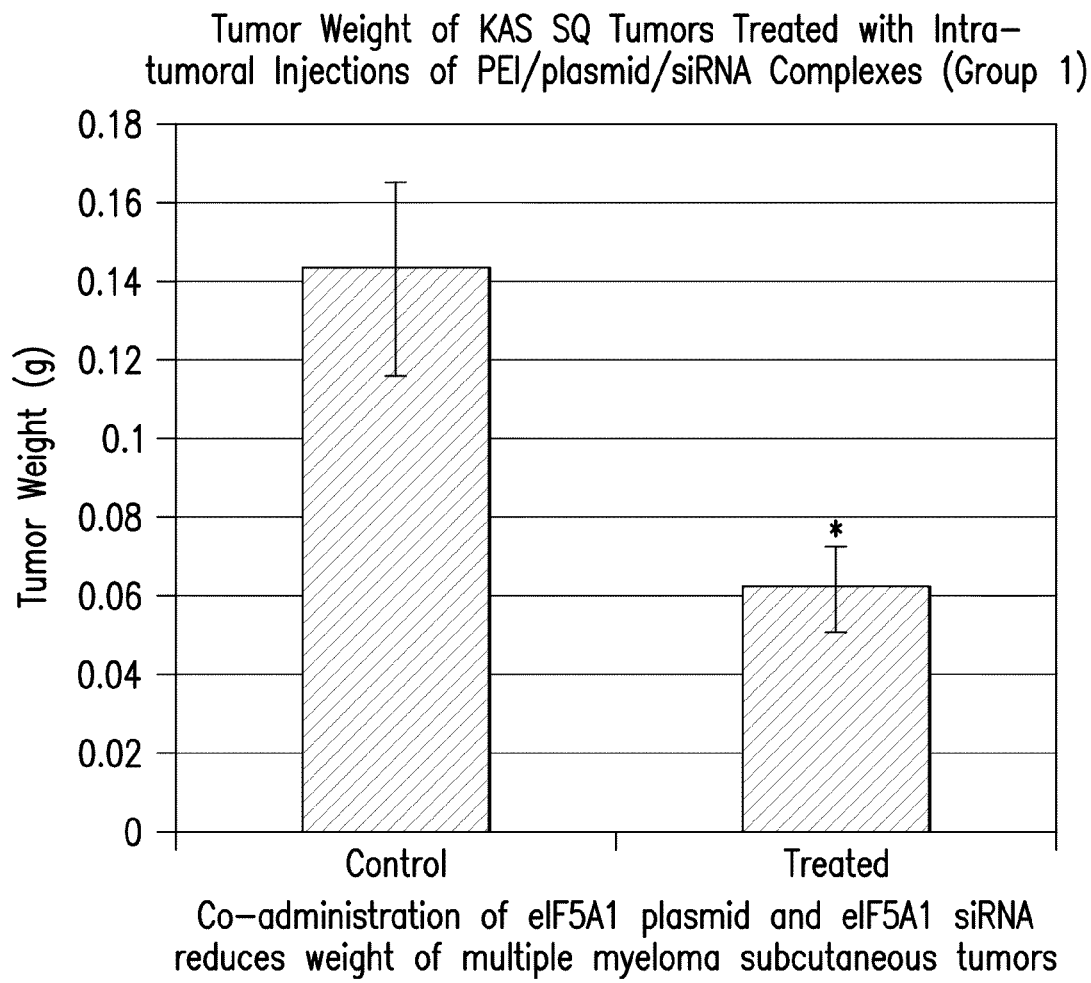
FIG. 10 shows that co-administration of eIF5A1 plasmid and eIF5A1 siRNA reduces weight of multiple myeloma subcutaneous tumors. See example 7.

Co-Administration of eIF-5A1 Plasmid and eIF-5A1 siRNA Delays Growth of Multiple Myeloma Subcutaneous Tumors (FIGS. 8-10)

SCID mice were injected subcutaneously with KAS cells. Treatment was initiated when palpable tumors were observed. Six 3-5 week old SCID/CB17 mice were injected with 10 million KAS-6/1 myeloma cells in 200 μL PBS in their right flank and treatment was initiated when the tumors reached a minimum size of 4 mm³.

Control mice were injected intra-tumorally 2 times per week with PEI complexes containing pCpG-mcs (empty vector) and control siRNA (control group was made up of 3 mice: C-1, C-2, and C-3). Treated mice were injected intra-tumorally 2 times per week with PEI complexes containing the RNAi-resistant plasmid pCpG-eIF5A1k50R and eIF5A1 siRNA (treated group was made up of 3 mice: 5A-1, 5A-2, and 5A-3). Injections were given at multiple sites within the tumor to prevent reflux and a slow rate of injection was used to increase uptake. The data in FIG. 8 shows the tumor volume for all the mice in the group. The data shown in FIG. 9 is the average tumor volume per group+/−standard error. Asterix denote statistical significance (*=p<0.025; n=3).

FIG. 10 shows that co-administration of eIF-5A1 plasmid and eIF-5A1 siRNA reduces the weight of multiple myeloma subcutaneous tumors. The data shown is the average tumor weight per group+/−standard error. Asterix denote statistical significance (*=p<0.05; n=3).

JET-PEI (PolyPlus) at 2×0.1 ml was used for the in vivo tests. The N/P ratio was 8. The PEI/DNA/siRNA complexes were formed in a total volume of 0.1 ml in 5% glucose. The protocol for forming complexes was as follows.
1. Bring components to room temperature. Keep sterile.
2. Dilute 20 µg of plasmid DNA (~10 µl at 2 mg/ml) and 10 µg siRNA (10 µl at 1 mg/ml) into a total volume of 25 µl. Use sterile water to make up difference.
3. Adjust the volume of DNA solution to 50 µl 5% glucose by adding 25 µl of 10% glucose. Vortex gently and centrifuge briefly.
4. Dilute 4.8 µl of in vivo JETPEI into a total volume of 25 µl of 10% glucose. Adjust volume to 50 µl with sterile water to end up with a final concentration of 5% glucose. Vortex gently and centrifuge briefly.
5. Immediately add 50 µl of diluted PEI to the 50 µl of diluted DNA (do not reverse the order). Vortex briefly and immediately spin down.
6. Incubate for 15 minutes prior to injection. Complexes are stable for 6 hours.

CpG-free Cloning Vectors and pCpG Plasmids were obtained from InvivoGen. These plasmids are completely devoid of CpG dinucleotides, named pCpG. These plasmids yield high levels of transgene expression both in vitro and in vivo, and in contrast to CMV-based plasmids allow sustained expression in vivo. pCpG plasmids contain elements that either naturally lack CpG dinucleotides, were modified to remove all CpGs, or entirely synthesized such as genes encoding selectable markers or reporters. Synthesis of these new alleles was made possible by the fact that among the sixteen dinucleotides that form the genetic code, CG is the only dinucleotide that is non-essential and can be replaced. Eight codons contain a CG encoding for five different amino acids. All eight codons can be substituted by at least a choice of two codons that code for the same amino acid to create new alleles that code for proteins having amino acid sequences that remain identical to the wild type and thus are as active as their wild-type counterparts. These new alleles are available individually in a plasmid named pMOD from which they can be easily excised.

pCpG plasmids allow long lasting expression in vivo, and represent valuable tools to study the effects of CpGs on gene expression in vivo and in vitro, using cell lines expressing TLR9, as well as their effects on the innate and acquired immune systems.

The empty vector, pCpG-mcs (Invivogen) is a vector with no expressed gene product, only a multiple cloning site, and was used as the control vector. An HA-tagged eIF5A1$^{k50R}$ cDNA was subcloned into the NcoI and NheI sites of a pCpG-LacZ vector (Invivogen), from which the LacZ gene had been removed, to give rise to the treatment vector pCpG-eIF5A1 (K50R). The DNA was prepared using Endo-Free Qiagen kit. Endotoxin levels measured and are <0.03 EU/ug; DNA should be at 2 mg/ml in water.

The control siRNA used in the experiments was a microarray validated non-targeting control siRNA from Dharmacon (D-001810-01). The siRNA was obtained with a modification (siSTABLE) to prevent degradation in serum.

The eIF5A1 siRNA used in the experiments was designed against the 3'UTR of human eIF5A1. There is no similarity between the eIF5A1 siRNA and mouse eIF5A1 and the siRNA should therefore only suppress human (but not mouse) eIF5A1. The siRNA also has no similarity to eIF5A2 (either human or mouse). The siRNA was obtained with a modification (siSTABLE) to prevent degradation in serum. The eIF5A1 siRNA has the following target sequence:

5' GCU GGA CUC CUC CUA CAC A (UU) 3' (SEQ ID NO: 5)

The siSTABLE siRNA was dissolved at 1 mg/ml in water (stored in aliquots at −20 C).

Tumor dimensions of length (l) and width (w) were measured 2-3 times per week using digital calipers. Tumor volume was calculated according to the following equation:
l=length; smallest dimension
w=width; largest dimension
tumor volume (mm$^3$)=l$^2$*w*0.5

Statistical Analyses

Student's t-test was used for statistical analysis. Significance was deemed to be a confidence level above 95% ($p<0.05$).

Example 8

Figure 11:
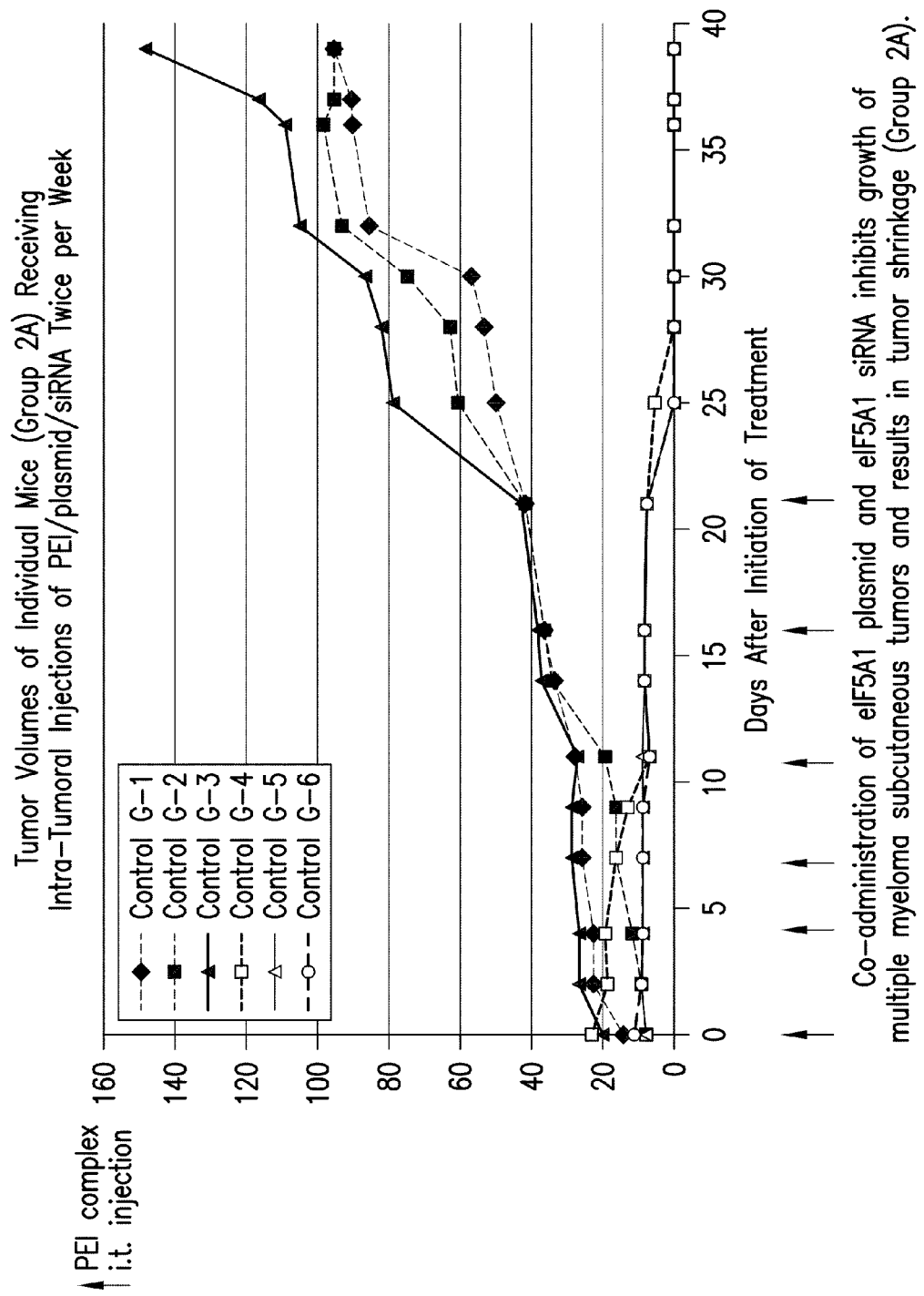
FIG. 11 shows that co-administration of eIF5A1 plasmid and eIF5A1 siRNA delays growth of multiple myeloma subcutaneous tumors and results in tumor shrinkage. See Example 8.

Co-Administration of eIF5A1 Plasmid and eIF5A1 siRNA Delays Growth of Multiple Myeloma Subcutaneous Tumors and Results in Tumor Shrinkage In another study, again SCID mice were injected subcutaneously with KAS cells. Treatment was initiated when palpable tumors were observed. Control mice were injected intra-tumorally 2 times per week with PEI complexes containing pCpG-mcs (empty vector) and control siRNA (control group G-1, G-2 and G-3). Treated mice were injected intra-tumorally 2 times per week with PEI complexes containing the RNAi-resistant plasmid pCpG-eIF5A1k50R (20 µg of plasmid DNA) and eIF5A1 siRNA (10 µg of siRNA)(treated group G-4, G-5 and G-6). The data shown in FIG. 11 is the average tumor volume per group+/−standard error. Asterix denote statistical significance (*=p<0.025; n=3). Six injections over a period of 21 days were given (red arrows).

Example 9

Administration of eIF5A1 siRNA Intra-Venously (i.v.) and PEI/eIF5A1K50R Plasmid Complexes Intra-Tumorally (i.t.) Results in Tumor Shrinkage of Multiple Myeloma Subcutaneous Tumors (Group 2B)

Figure 12:
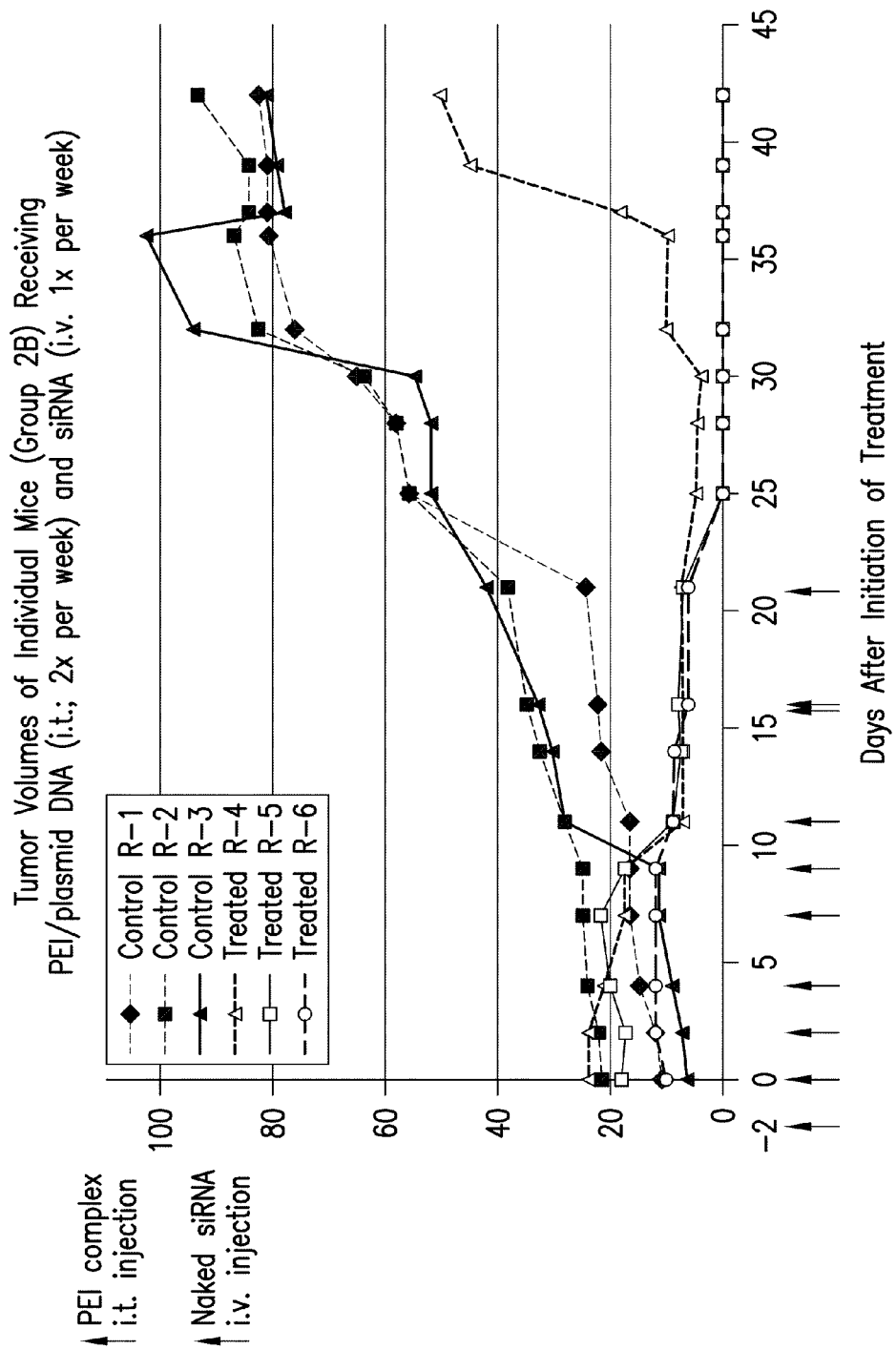
FIG. 12 shows that administration of eIF5A1 siRNA intra-venously (i.v.) and PEI/eIF5A1K50R plasmid complexes intra-tumorally (i.t.) results in tumor shrinkage of multiple myeloma subcutaneous tumors. See example 9.

SCID mice were injected subcutaneously with KAS cells. When palpable tumors were observed treatment was initiated with an initial tail injection of 50 micrograms of either control siRNA (control group) or human eIF5A1 siRNA (treated group). Control Mice were subsequently treated by intra-tumoral injections 2 times per week with PEI complexes containing pCpG-mcs (empty vector; control group; G-1, G-2, and G-3). Treated mice were subsequently treated by intra-tumoral injections 2 times per week with PEI complexes containing the RNAi-resistant plasmid pCpG-eIF5A1k50R (20 µg plasmid DNA) (treated group; G-4, G-5, and G-6). Control mice continued to receive control siRNA (control group R-1, R-2, and R-3) by i.v. injection once per week. Treated mice continued to receive human eIF5A1 siRNA (20 µg) (treated group R-4, R-5, and R-6) by i.v. injection once per week. The data shown in FIG. 12 is the tumor volume for all the mice in each group. Six intramural injections of PEI/DNA (red arrows) and four i.v. injections of siRNA (blue arrows) were given over a period of 21 days.

Figure 13A:
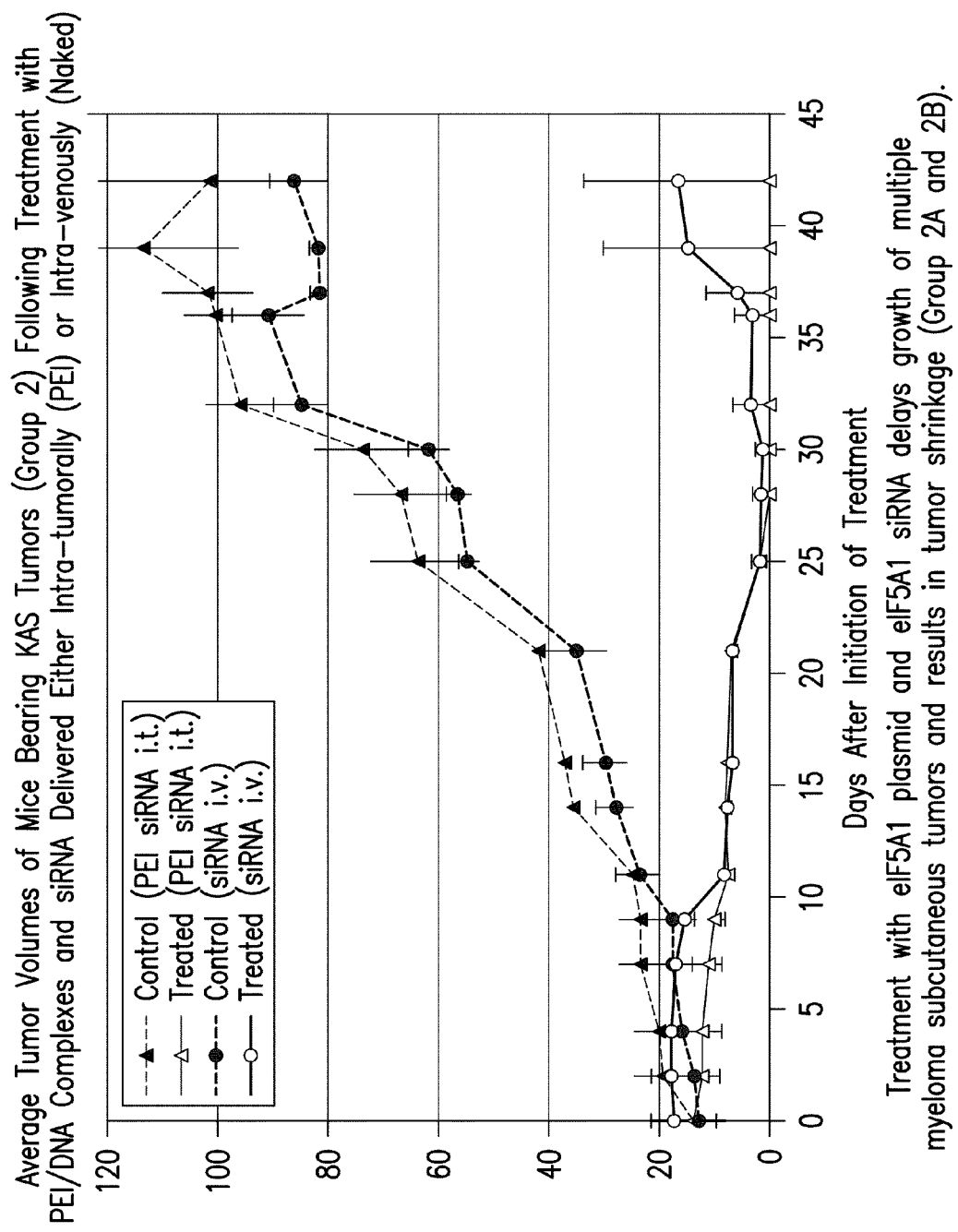
FIG. 13A shows that treatment with eIF5A1 plasmid and eIF5A1 siRNA delays growth of multiple myeloma subcutaneous tumors and results in tumor shrinkage.

FIG. 13 provides an overlay of the results from Example 8 and 9. SCID mice were injected subcutaneously with KAS cells. The data shown in FIG. 13 is the average tumor volume for the mice in each group+/−standard error. Asterix denote statistical significance between treated and control groups (=p<0.01; *=p<0.001; n=3).

Protocol for Forming PEI Complexes:
1. Bring components to room temperature. Keep sterile.
2. Dilute plasmid DNA or plasmid DNA+siRNA into a total volume of 25 μl. Use sterile water to adjust the volume.
   a) For plasmid DNA only complexes:
      Dilute 20 μg of plasmid DNA (10 μl at 2 mg/ml) into a total volume of 25 μl. Use sterile water to make up difference.
   b) For plasmid DNA+siRNA complexes:
      Dilute 20 μg of plasmid DNA (~10 μl at 2 mg/ml) and 10 μg of siRNA (10 μl at 1 mg/ml) into a total volume of 25 μl. Use sterile water to make up difference.
3. Adjust the volume of DNA solution to 50 μl 5% glucose by adding 25 μl of 10% glucose (provided with PEI kit). Vortex gently and centrifuge briefly.
4. Dilute in vivo JETPEI into a total volume of 25 μl of 10% glucose.
   a) For plasmid DNA only complexes:
      Dilute 3.2 μl of in vivo JETPEI into a total volume of 25 μl of 10% glucose. Adjust volume to 50 μl with sterile water to end up with a final concentration of 5% glucose. Vortex gently and centrifuge briefly.
   b) For plasmid DNA+siRNA complexes:
      Dilute 4.8 μl of in vivo JETPEI into a total volume of 25 μl of 10% glucose. Adjust volume to 50 μl with sterile water to end up with a final concentration of 5% glucose. Vortex gently and centrifuge briefly.
5. Immediately add 50 μl of diluted PEI to the 50 μl of diluted DNA (do not reverse the order!). Vortex briefly and immediately spin down.
6. Incubate for 15 minutes prior to injection. Complexes are stable for 6 hours.

Regarding the tail-vein injection of siRNA, the initial siRNA injection was 50 micrograms. siRNA was diluted to 0.4 mg/ml in PBS. 125 μl per mouse (50 μg) was injected into the tail vein. Subsequent injections of serum-stabilised siRNA were given two times per week at 20 μg per mouse. siRNA was diluted to 0.4 mg/ml in PBS. 50 μl per mouse (20 μg) was injected into the tail vein.

Figure 13B:
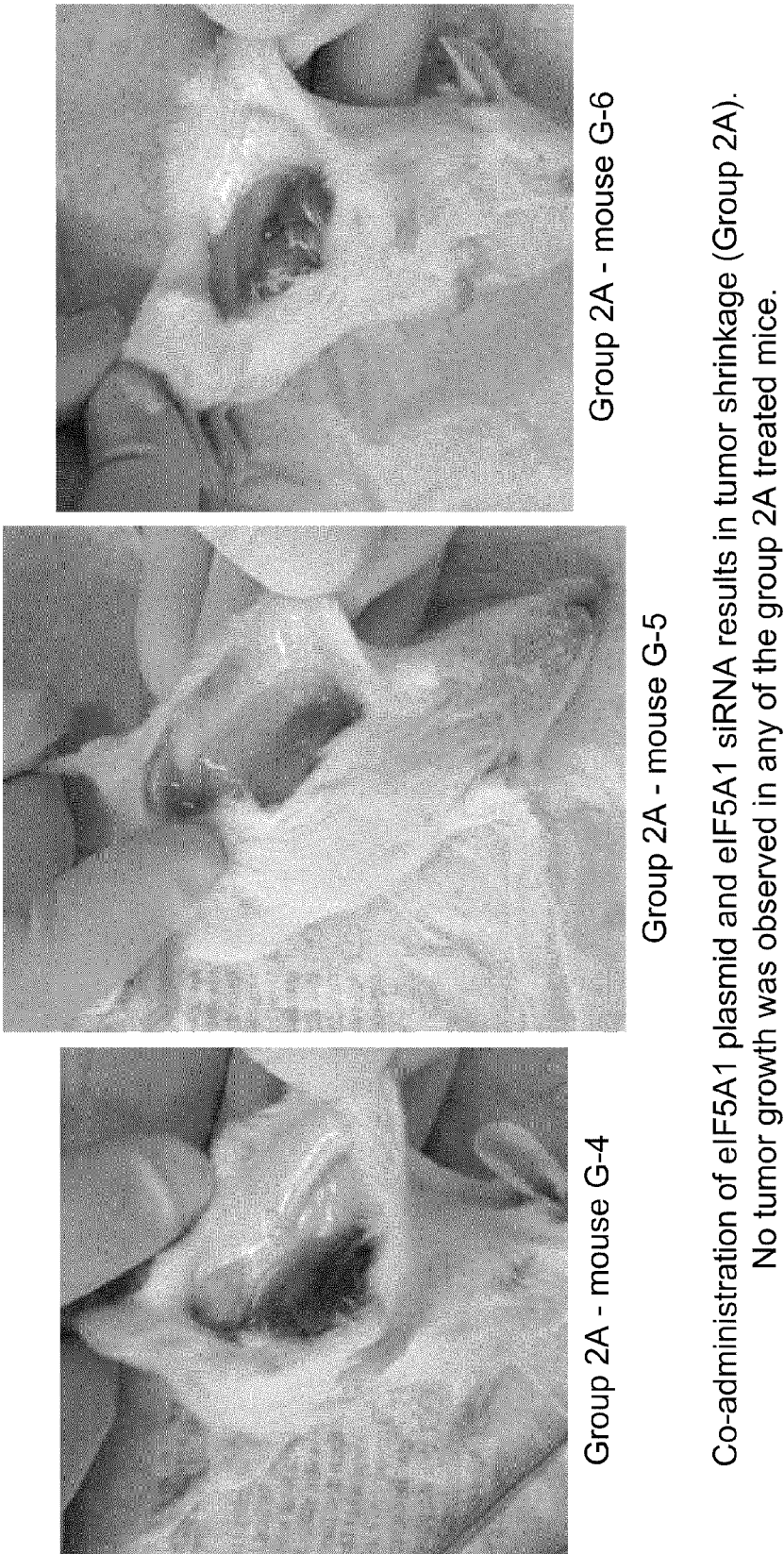
FIG. 13B shows that co-administration of eIF5A1 plasmid and eIF5A1 siRNA results in tumor shrinkage.

FIG. 13B shows that co-administration of eIF5A1 plasmid and eIF5A1 siRNA results in tumor shrinkage. SCID mice were injected subcutaneously with KAS cells. Treatment was initiated when palpable tumors were observed. Mice were injected intra-tumorally 2 times per week with PEI complexes containing the RNAi-resistant plasmid pCpG-eIF5A1k50R and eIF5A1 siRNA (treated group; G-4, G-5, and G-6). Six injections over a period of 21 days were given. Forty-two days after the initiation of treatment the mice were sacrificed and the skin under the tumor site was opened and examined for evidence of tumor growth. No tumor growth was observed in any of the group 2A treated mice.

Figure 13C:
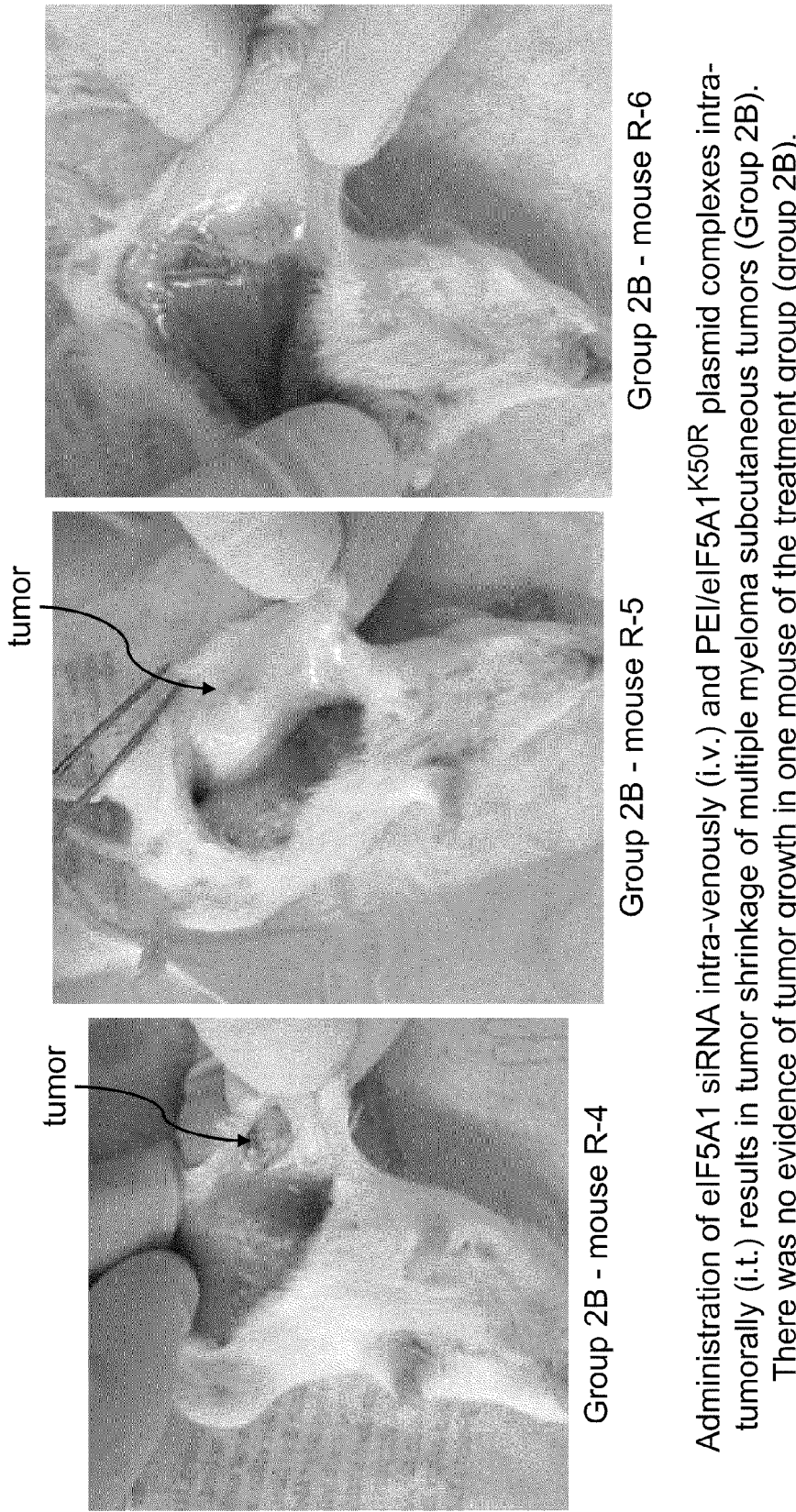
FIG. 13C shows that administration of eIF5A1 siRNA intra-venously (i.v.) and PEI/eIF5A1$^{K50R}$ plasmid complexes intra-tumorally (i.t.) results in tumor shrinkage of multiple myeloma subcutaneous tumors.

FIG. 13C shows that administration of eIF5A1 siRNA intra-venously (i.v.) and PEI/eIF5A1K50R plasmid complexes intra-tumorally (i.t.) results in tumor shrinkage of multiple myeloma subcutaneous tumors. SCID mice were injected subcutaneously with KAS cells. When palpable tumors were observed treatment was initiated with an initial injection of 50 micrograms of human eIF5A1 siRNA (treated group). Mice were subsequently treated by intra-tumoral injections 2 times per week with PEI complexes containing the RNAi-resistant plasmid pCpG-eIF5A1k50R (treated group; R-4, R-5, and R-6). Mice continued to receive human eIF5A1 siRNA by i.v. injection once per week. Treatment ended 21 days after initiation of treatment. Forty-two days after the initiation of treatment the mice were sacrificed and the skin under the tumor site was opened and examined for evidence of tumor growth. There was no evidence of tumor growth in one mouse of the treatment group (group 2B).

Example 10

Figure 14:
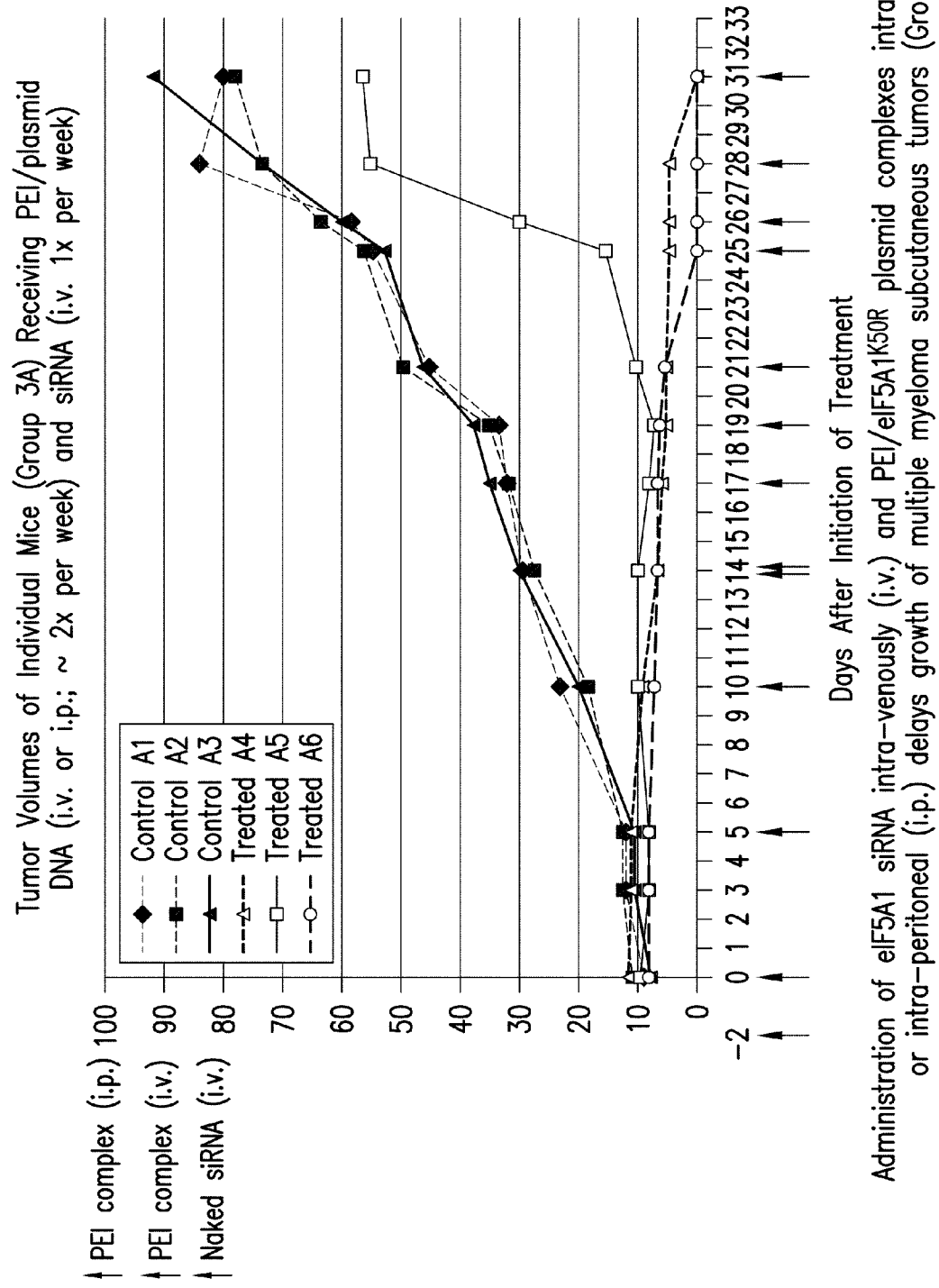
FIG. 14 shows that intra-venous co-administration of eIF5A1 plasmid and eIF5A1 siRNA delays growth of multiple myeloma subcutaneous tumors. See example 10.

Intra-Venous Co-Administration of eIF5A1 Plasmid and eIF5A1 siRNA Delays Growth of Multiple Myeloma Subcutaneous Tumors SCID mice were injected subcutaneously with KAS cells. When palpable tumors were observed treatment was initiated with an initial injection of 50 micrograms of either control siRNA (control group) or human eIF5A1 siRNA (treated group). Mice were subsequently treated by intra-venous (red arrows) or intra-peritoneal injections (green arrow) ~twice per week with either PEI complexes containing pCpG-mcs (empty vector; control group A1, A2, and A3) or PEI complexes containing the RNAi-resistant plasmid pCpG-eIF5A1k50R (treated group; A4, A5, and A6). Mice continued to receive either control siRNA (control group A1, A2, and A3) or human eIF5A1 siRNA (treated group A4, A5, and A6) by i.v. injection (blue arrows) once per week. The data shown is the tumor volume for all the mice in each group. The data shown in FIG. 14 is the tumor volume for all the mice in each group.

Example 11

Figure 15:
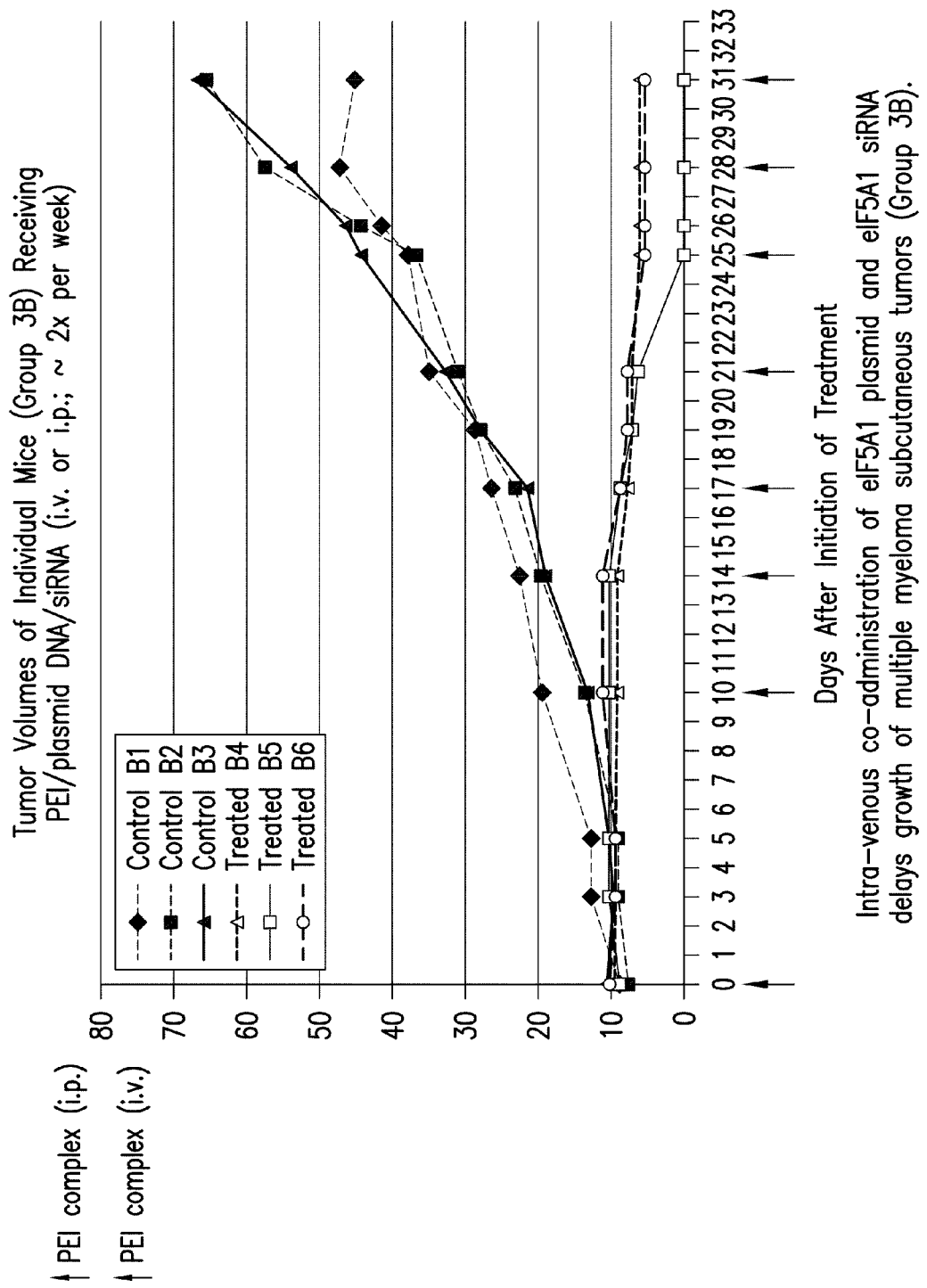
FIG. 15 shows that administration of eIF5A1 siRNA intra-venously (i.v.) and PEI/eIF5A1K50R plasmid complexes intra-venously (i.v.) or intra-peritoneal (i.p.) delays growth of multiple myeloma subcutaneous tumors. See example 11.

Administration of eIF5A1 siRNA Intra-Venously (i.v.) and PEI/eIF5A1K50R Plasmid Complexes Intra-Venously (i.v.) or Intra-Peritoneal (i.p.) Delays Growth of Multiple Myeloma Subcutaneous Tumors SCID mice were injected subcutaneously with KAS cells. When palpable tumors were observed treatment was initiated with an initial injection of 50 micrograms of either control siRNA (control group) or human eIF5A1 siRNA (treated group). Control mice were subsequently treated by intra-venous or intra-peritoneal injections~once per week with PEI complexes containing pCpG-mcs (empty vector; control group was three mice: B1, B2, and B3). Treated mice were subsequently treated by intra-venous or intra-peritoneal injections~once per week with PEI complexes containing the RNAi-resistant plasmid pCpG-eIF5A1$^{K50R}$ (treated group; B4, B5, and B6). Mice continued to receive either control siRNA (control group B1, B2, and B3) or human eIF5A1 siRNA (treated group was three mice: B4, B5, and B6) by i.v. injection once per week. The experiment began with initial siRNA injection of 50 μg (day-2 on graph in FIG. 15). Subsequent injections used 20 micrograms of siRNA once weekly. The siRNA was given naked, i.e. no delivery vehicle. PEI complexes contained 20 μg of plasmid DNA. The initial PEI injection was given i.p. and subsequent injections were given i.v. The data shown in FIG. 15 is the tumor volume for all the mice in each group.

Figure 16:
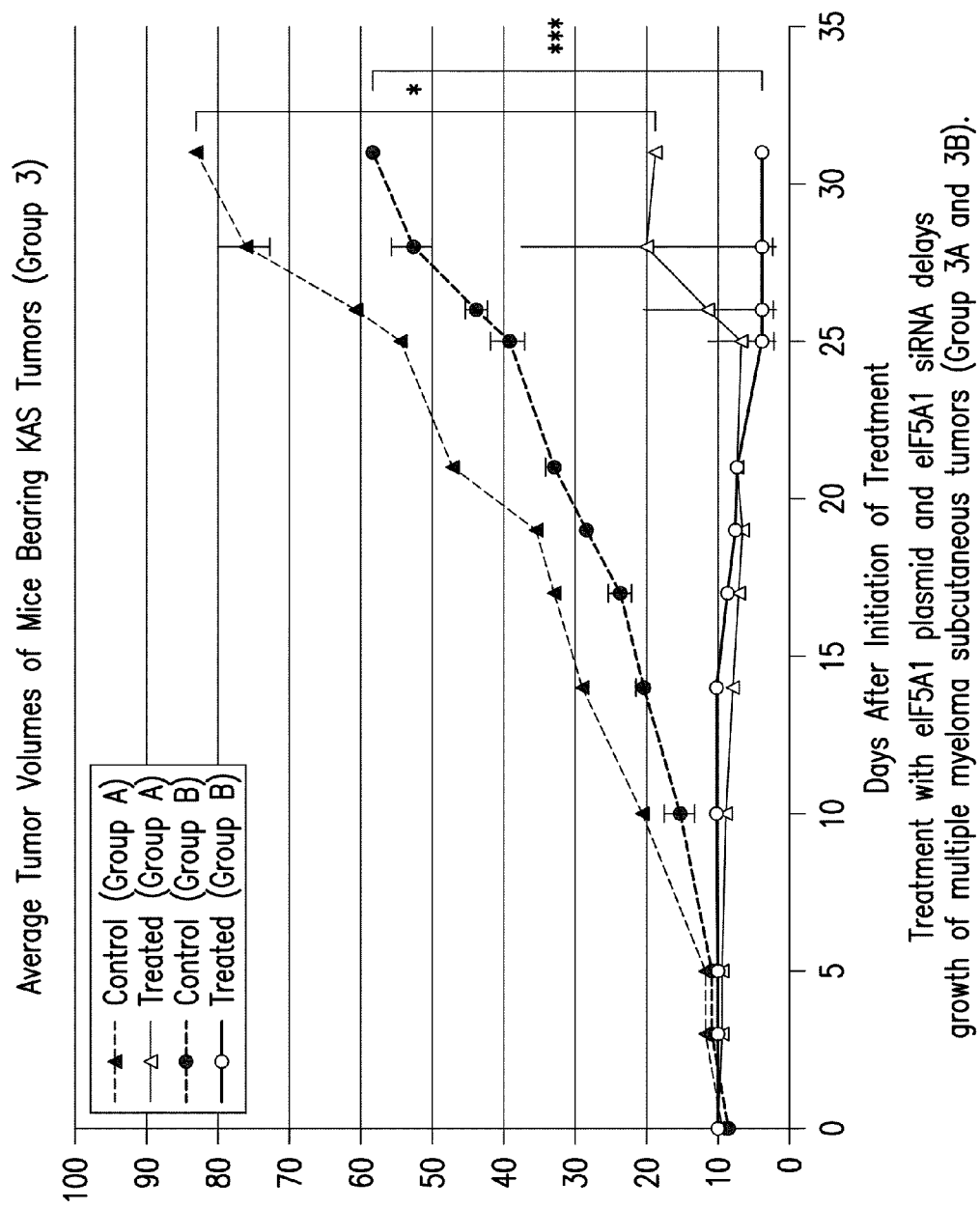
FIG. 16 shows that treatment with eIF5A1 plasmid and eIF5A1 siRNA delays growth of multiple myeloma subcutaneous tumors.

FIG. 16 provides an overlay of Example 10 and 11. SCID mice were injected subcutaneously with KAS cells. Treatment was initiated when palpable tumors were observed. One set of mice received i.v. injections of either control siRNA (control; Group A) or eIF5A1 siRNA (treated; Group A) once per week and either i.v. or i.p. of either PEI complexes containing pCpG-mcs (control; Group A) or PEI complexes containing the RNAi-resistant plasmid pCpG-eIF5A1$^{K50R}$ (treated; Group A). A second set of mice were given i.v. or i.p. injections ~2 times per week with either PEI complexes containing pCpG-mcs (empty vector) and control siRNA (control; Group B.) or PEI complexes containing the RNAi-resistant plasmid pCpG-eIF5A1k50R and eIF5A1 siRNA (treated; Group B). The data shown is the average tumor volume for the mice in each group+/−standard error. Asterix denote statistical significance between treated and control groups (*=p<0.05; ***=p<0.001; n=3).

The protocols for preparing the PEI complexes and the siRNA are as described in previous examples.

Example 12

Figure 17A:
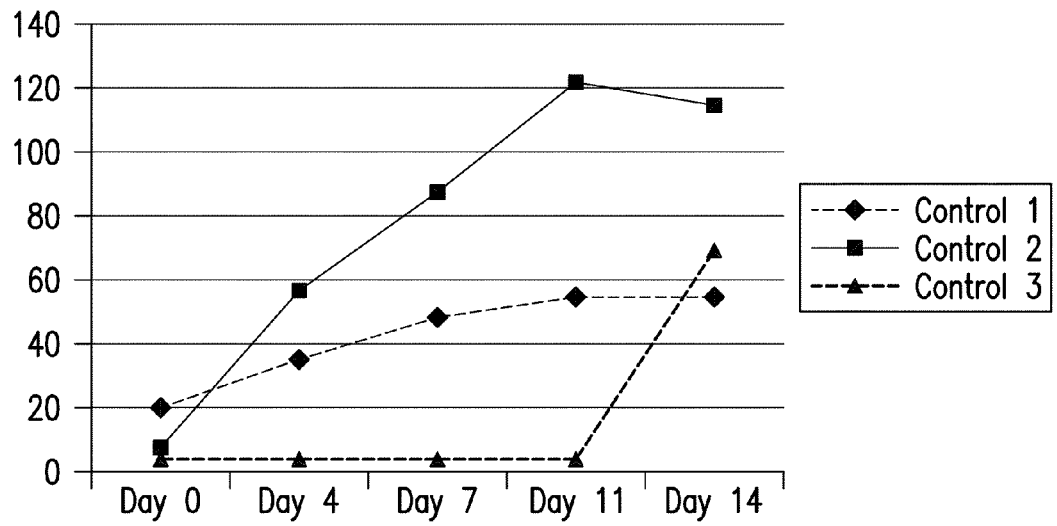
FIG. 17 shows that co-administration of eIF5A1 plasmid and eIF5A1 siRNA delays growth of multiple myeloma subcutaneous tumors and results in tumor shrinkage. See example 12.
Figure 17B:
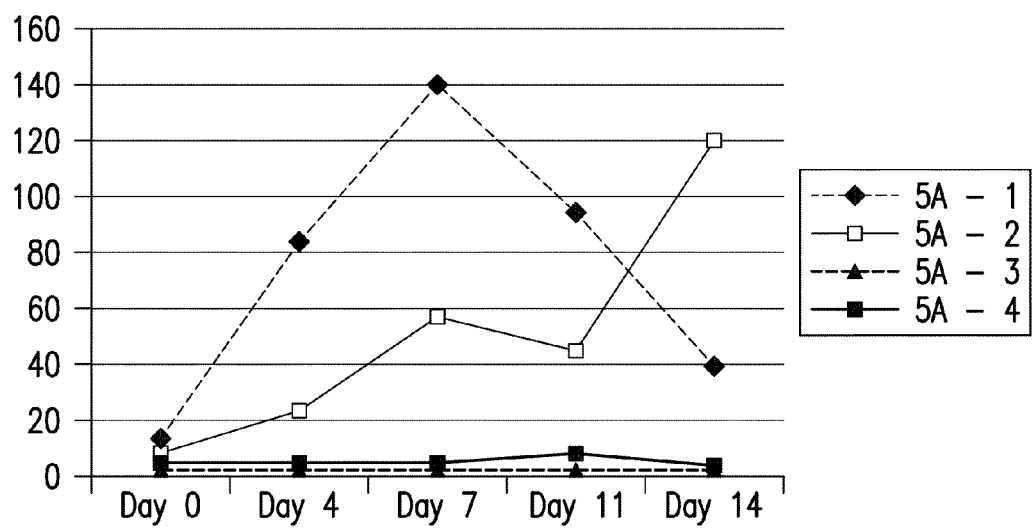

Co-Administration of eIF5A1 Plasmid and eIF5A1 siRNA Delays Growth of Multiple Myeloma Subcutaneous Tumors and Results in Tumor Shrinkage SCID mice were injected subcutaneously with KAS cells. Treatment was initiated when palpable tumors were observed. Control mice were injected intra-tumorally 2 times per week with PEI complexes containing pCpG-mcs (empty vector) and control siRNA (control group had 3 mice: control 1, control 2, and control 3). Treated mice were injected intra-tumorally 2 times per week with PEI complexes containing the RNAi-resistant plasmid pCpG-eIF5A1$^{K50R}$ and eIF5A1 siRNA (treated group contained 4 mice: 5A-1, 5A-2, 5A-3, and 5A-4). The intra-tumoral rejections of PEI complexes contained both 20 μg of plasmid DNA and 10 μg of siRNA. The data shown in FIG. 17 is the tumor volume for all the mice in each group.

Example 13

Administration of eIF5A1 siRNA Intra-Venously (i.v.) and PEI/eIF5A1$^{K50R}$ Plasmid Complexes Intra-Tumorally (i.t.) Results in Tumor Shrinkage of Multiple Myeloma Subcutaneous Tumors SCID mice were injected subcutaneously with KAS cells. When palpable tumors were observed treatment was initiated with an initial injection of 50 micrograms of either control siRNA (control group had three mice: control 1, control 2 and control 3) or human eIF5A1 siRNA (treated group had 3 mice: 5A-1, 5A-2, 5A-3). Control mice were subsequently treated by intra-tumoral injections 2 times per week with PEI complexes containing pCpG-mcs (20 μg) (control group 1-3). Treated mice were subsequently treated by intra-tumoral injections 2 times per week with PEI complexes containing the RNAi-resistant plasmid pCpG-eIF5A1$^{K50R}$ (20 μg) (5A-1, 5A-2, 5A-3). Control mice continued to receive either control siRNA (20 μg) by tail vein i.v. injection twice per week. Treated mice continued to receive human eIF5A1 siRNA (20 μg) by tail vein i.v. injection twice per week. The injections were given 48 hours prior to the intra-tumoral injections. The siRNA was given as naked siRNA, i.e. no delivery vehicle. The data shown in FIG. 18 is the tumor volume for all the mice in each group.

Example 14

Figure 19:
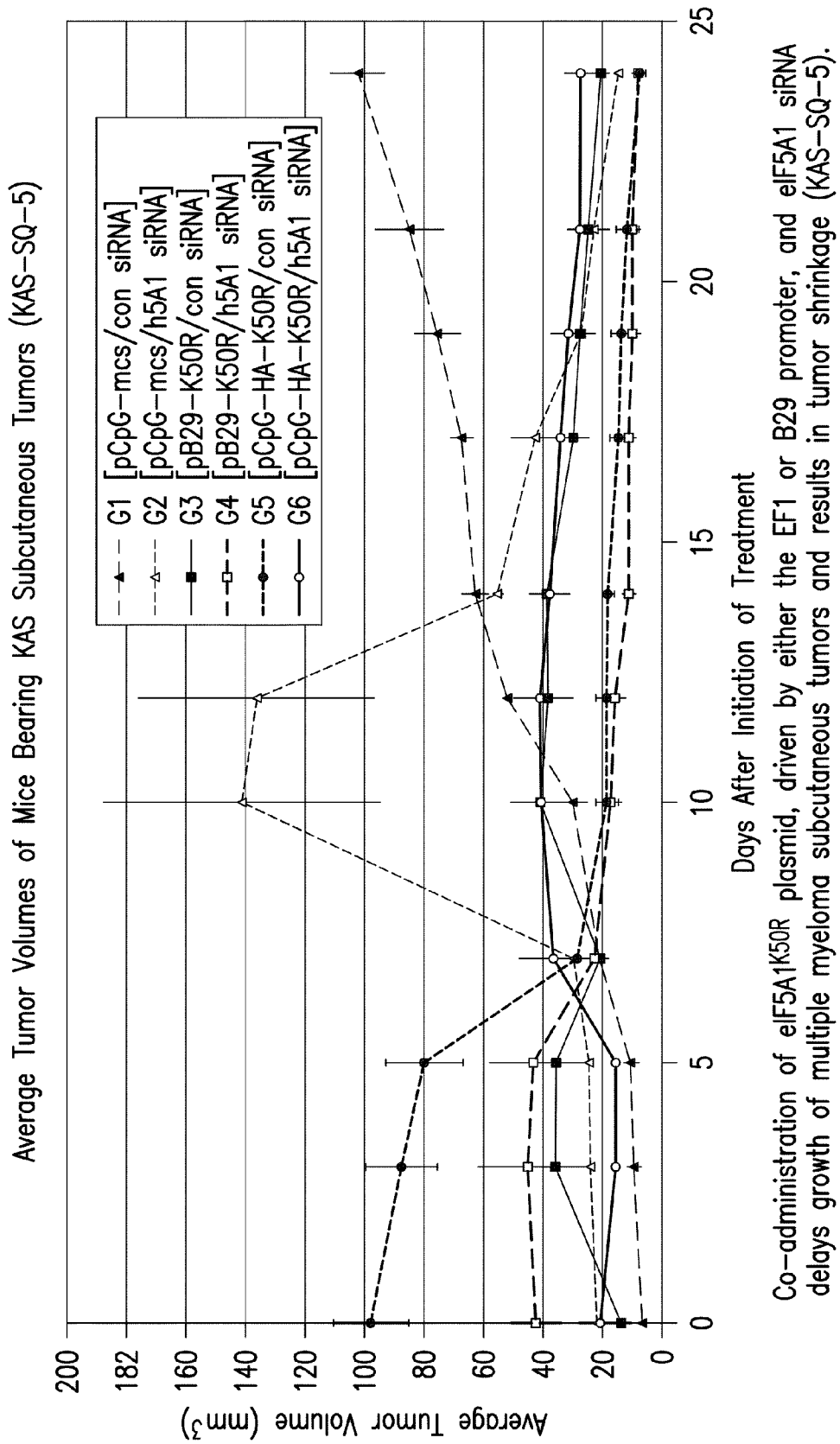
FIG. 19 shows co-administration of eIF5A1$^{K50R}$ plasmid, driven by either the EF1 or B29 promoter, and eIF5A1 siRNA delays growth of multiple myeloma subcutaneous tumors and results in tumor shrinkage (KAS-SQ-5). See example 14.

Co-Administration of eIF5A1$^{K50R}$ Plasmid, Driven by Either the EF1 or B29 Promoter, and eIF5A1 siRNA Delays Growth of Multiple Myeloma Subcutaneous Tumors and Results in Tumor Shrinkage SCID mice were injected subcutaneously with KAS cells. Treatment was initiated when palpable tumors were observed. Mice were injected intra-tumorally 2 times per week with PEI complexes containing either control vector (G1 and G2) or an eIF5A1 plasmid driven by either the B29 promoter (G3 and G4) or the EF1 promoter (G5 and G6) and either control siRNA (G1, G3, G5) or h5A1 siRNA (G2, G4, G6). The data shown is the average tumor volume+/−standard error for each group. Note: the B29 promoter was intended as a B-cell-specific promoter. However, although the B29 promoter/mCMV enhancer used in this study was found to drive high expression of HA-eIF5A1$^{K50R}$ in KAS cells in vitro, it does not appear to be B-cell-specific (likely due to CMV enhancer). See FIG. 19.

Example 15

Figure 20:
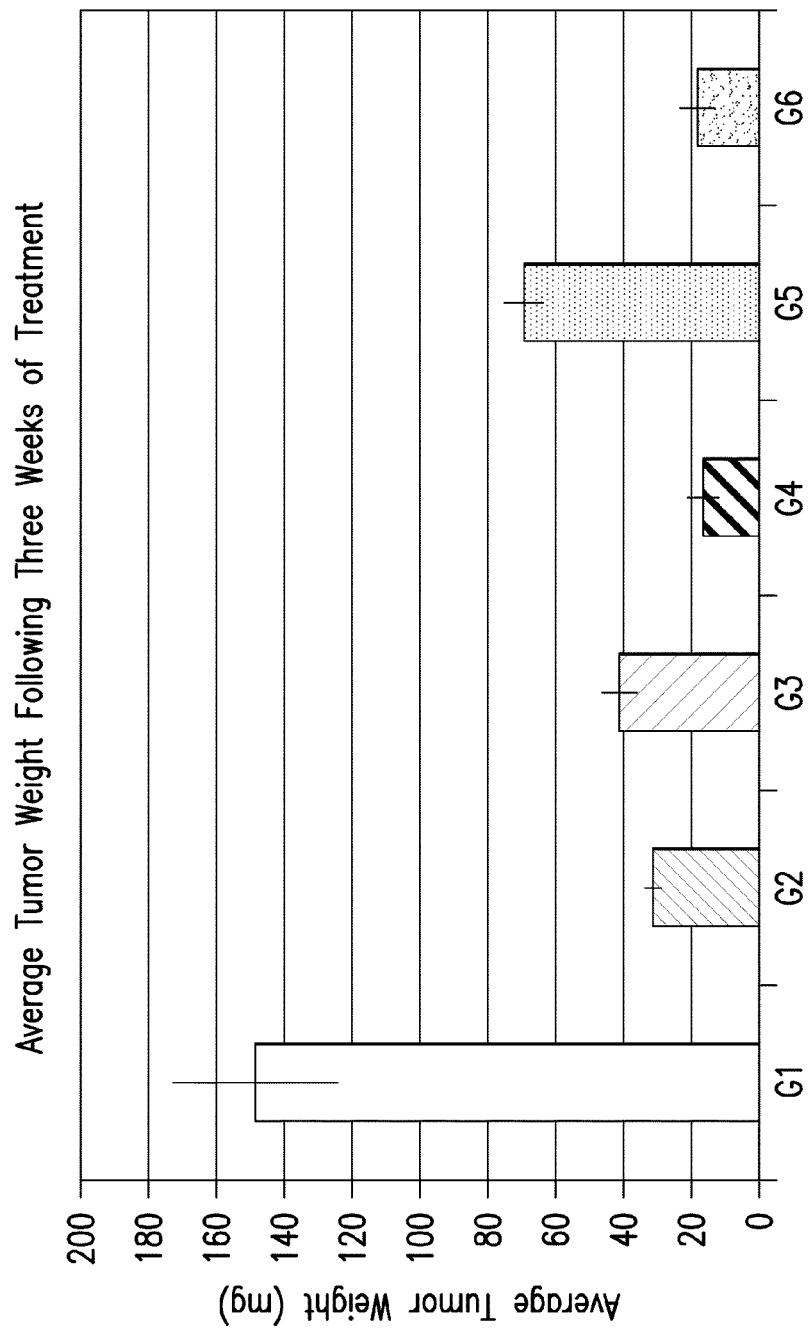
FIG. 20 shows co-administration of eIF5A1 siRNA increases anti-tumor effect of eIF5A1$^{K50R}$ plasmid, driven by either the EF1 or B29 promoter, on multiple myeloma subcutaneous tumors and results in reduced tumor burden (KAS-SQ-5). See example 15.

Co-Administration of eIF5A1 siRNA Increases Anti-Tumor Effect of eIF5A1$^{K50R}$ Plasmid, Driven by Either the EF1 or B29 Promoter, on Multiple Myeloma Subcutaneous Tumors and Results in Reduced Tumor Burden SCID mice were injected subcutaneously with KAS cells. Treatment was initiated when palpable tumors were observed. Mice were injected intra-tumorally 2 times per week with PEI complexes containing either control vector (G1 and G2) or an eIF5A1 plasmid driven by either the B29 promoter (G3 and G4) or the EF1 promoter (G5 and G6) and either control siRNA (G1, G3, G5) or h5A1 siRNA (G2, G4, G6). The mice were sacrificed 24 days after the initiation of treatment and the subcutaneous tumor was removed and weighed. The data shown is the average tumor weight+/−stadard error for all groups. See FIG. 20.

Figure 21:
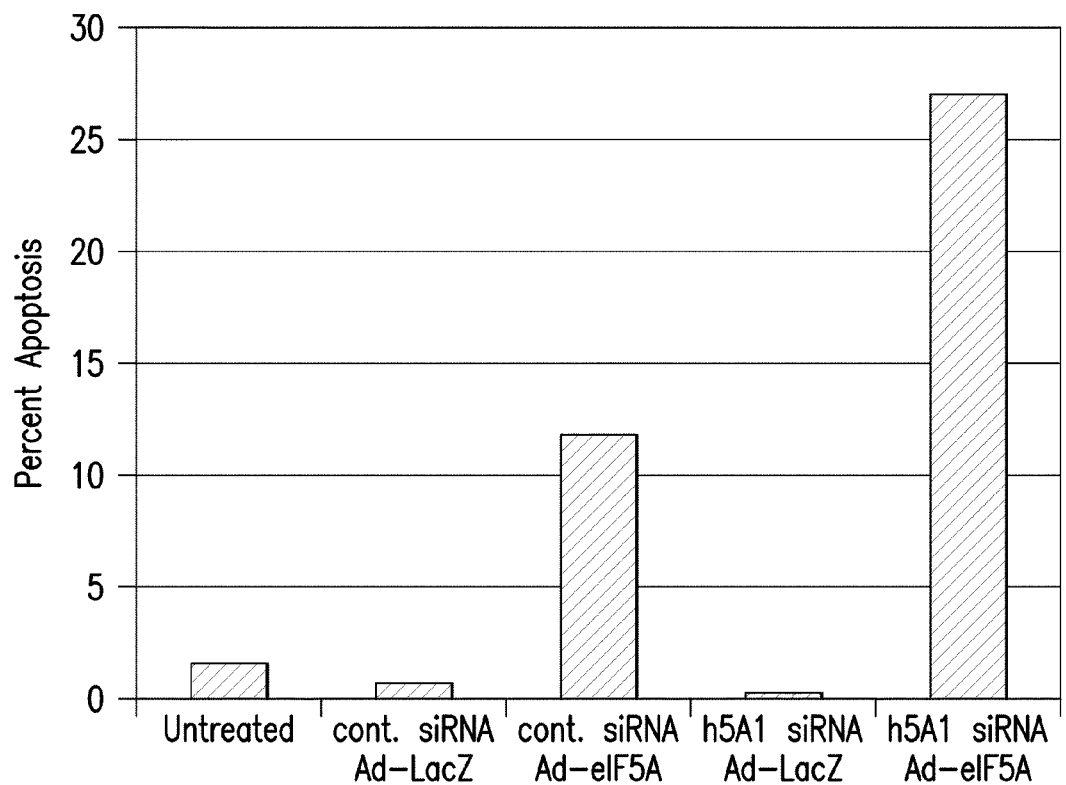
FIG. 21 shows eIF5A1 siRNA synergistically increases apoptosis resulting from infection with Ad-eIF5A in lung adenocarcinoma cells. See example 16.

Example 16 eIF5A1 siRNA Synergistically Increases Apoptosis Induction Resulting from Infection with Ad-eIF5A in Lung Adenocarcinoma Cells A549 cells were infected with either Ad-LacZ or Ad-eIF5A. Cells were transfected with either a control siRNA or an siRNA targeting human eIF5A1 (h5A1) by adding the transfection media to cells immediately following addition of the virus. Four hours after transfection with the siRNA and infection with virus, the media was replaced with fresh media and the cells were incubated for 72 hours prior to labelling with Annexin/PI to detect apoptotic cells. Note: over-expression of eIF5A in this cell line results in the accumulation of unhypusinated eIF5A due to limiting amounts of DHS and DOHH and therefore results in same pro-apoptotic effect as over-expression of eIF5A$^{K50R}$. These data indicate that the synergistic effect in apoptosis caused by simultaneous suppression of hypusinated eIF5A and over-expression of unhypusinated eIF5A is observed in non-myeloma tumor-types as well. See FIG. 21.

Example 17

Construction of Plasmid pExp5A pExp5A is an expression plasmid with reduced CpG dinucleotides designed to drive expression of human eIF5A1$^{K50R}$ predominantly in cells of B cell lineage. The vector is derived from pCpG-LacZ, a plasmid completely devoid of CpG dinucleotides (Invivogen). All the elements required for replication and selection in E. coli are free of CpG dinucleotides. The original CMV enhancer/promoter and LacZ gene from the CpG-LacZ vector have been replaced with a human minimal B cell specific promoter (B29/CD79b; Invivogen) and human eIF5A1$^{K50R}$, respectively, in order to drive B-cell specific expression of eIF5A1$^{K50R}$. The B29 DHS4.4 3' enhancer has been introduced into the plasmid downstream of the eIF5A1 expression cassette in order to enhance activity of the B29 promoter and reduce expression in non-B cells (Malone et al. 2006. B29 gene silencing in pituitary cells is regulated by its 3' enhancer. J. Mol. Biol. 362: 173-183). Incorporation of the B29 minimal promoter, eIF5A1$^{K50R}$, and the B29 DHS4.4 3' enhancer has introduced 32 CpG dinucleotides into the vector.

Elements for Expression in *E. coli*
Origin of replication: *E. coli* R6K gamma ori.
* Due to the presence of the R6K gamma origin of replication, pCpG plasmids can only be amplified in *E. coli* mutant strain expressing a pir mutant gene. They will not replicate in standard *E. coli* strains. Therefore, pCpG plasmids are provided with the *E. coli* GT115 strain, a pir mutant also deficient in Dcm methylation (Invivogen).
Bacterial promoter: EM2K, a CpG-free version of the bacterial EM7 promoter.
Selectable marker: Zeocin™ resistance gene; a synthetic allele with no CpGs.
Elements for Expression in Mammalian Cells
Mammalian promoter: the human −167 bp minimal B29 (CD79b) promoter for tissue-specific expression in B cells. A synthetic intron (I 140) is also present in the 5'UTR.
Polyadenylation signal: a CpG dinucleotide-free version of the late SV40 polyadenylation signal.
3' Enhancer: the human B29 DHS4.4 3' enhancer.
MAR: Two CpG-free Matrix attached regions (MAR) are present between the bacterial and mammalian transcription units. One MAR is derived from the 5' region of the human IFN-βgene and one from the 5' region of the β-globin gene.
The predicted Sequence of pExp5A (3371 bp is provided at FIG. 23.
Amino Acid Sequence of eIF5A1$^{K50R}$ (SEQ ID NO: 6)
* K50R mutation is underlined MADDLDFETGDAGASATFPMQCSALRKNGFVVLKGRPCKIVEMSTSKTG<u>R</u>

HGHAKVHLVGIDIFTGKKYEDICPSTHNMDVPNIKRNDFQLIGIQDGYLS

LLQDSGEVREDLRLPEGDLGKEIEQKYDCGEEILITVLSAMTEEAAVAIK

AMAK

Construction of pExp5A—Outline of Construction:
Step 1: Cloning of B29 DHS4.4 3' enhancer and subcloning into pGEM T easy (Promega)—creates pGEM-4.4enh #8.
Step 2: Subcloning of minimal B29 promoter into pCpG-LacZ (Invivogen)—creates B29-5 #3.
Step 3: Subcloning of HA-eIF5A1$^{K50R}$ into B29-5 #3 vector—creates B29-5#3-eIF5A1$^{K50R}$.
Step 4: Creation of new multiple cloning site in pCpG-mcs (Invivogen)—creates pCpG-Linker4.
Step 5: Subcloning of B29 DS4.4 3' enhancer into pCpG-Linker4—creates pCpG-DHS4.4.
Step 6: Subcloning of B29 promoter+HA-eIF5A1$^{K50R}$+SV40 pA expression cassette into pCpG-DHS4.4 creates pExp-5.
Step 7: Replacement of HA-eIF5A1$^{K50R}$ in pExp-5 with non-HA eIF5A1$^{K50R}$ creates final vector, pExp5A.
Construction in Detail:
Step 1: Cloning of B29 DHS4.4 3' Enhancer and Subcloning into pGEM T Easy (Promega)—Creates pGEM-4.4enh #8.

The B29 DHS4.4 3' enhancer was cloned by PCR from genomic DNA isolated from KAS cells (human multiple myeloma cell line) using the following primers: forward 5'-CAGCAAGGGAGCACCTATG-3' (SEQ ID NO: 7) and reverse 5'-GTTGCAGTGAGCGGAGATG-3' (SEQ ID NO: 8). The primers were designed using the sequence of the human CD79B/GH-1 Intergenic region (Accession AB062674). The resulting 608 bp PCR fragment was subcloned into the pGEM® T easy cloning vector (Promega) and sequenced. Komatsu et al. 2002. Novel regulatory regions found downstream of the rat B29/Ig-b gene. Eur. J. Biochem. 269: 1227-1236.

Sequence of B29 DHS4.4 3' Enhancer PCR Fragment (297 bp) in pGEM-4.4enh #8 (SEQ ID NO: 9)

ACCACCCTGGGCCAGGCTGGGCCAAGCCAGGCGGCCCCTGTGTTTTCCCC

AGTCTCTGGGCTGCTGGAGGGAACCAGG<u>TTGTTT</u>TGG<u>CATCAGC</u>CTCTAC

TGAGCCGGAGCCCTTCCTTTCCTGCTGCTTTGCATAGTGGCACTAATTCC

GTCCTCCTACCTCCACCAGGGACCTAGGCAGCCGGGTAGATGGTGGGAGG

AGGCTTCACTTCTCCCCCAAGCAGGGTCTCCACCTGCTT*GAGGCTGCCCT*

GGGTTGGGGGAGGCCTTGGCTTTACCTAAAGACTTTTTAACACCTCT

+4.4 regions contains several transcription factor binding sites

| SRY | <u>GTTGTTT</u> |
| --- | --- |
| GATA | <u>CATCAGC</u> |
| OCT-X | GCTGCTTTGCATAG (residues 124-137 of SEQ ID NO: 9) |
| NF-KB | *GAGGCTGCCC* (residues 240-249 of SEQ ID NO: 9) |

Alignment of B29 DHS4.4 3' Enhancer PCR Fragment (297 bp (SEQ ID NO: 9)) in pGEM-4.4enh #8 with Sequence of the Human CD79B/GH-1 Intergenic Region (Accession AB062674) (SEQ ID NO: 10)). The consensus sequence is disclosed as SEQ ID NO: 9.

```
         1       10        20        30        40        50        60        70        80        90       100       110       120      130
         |--------+---------+---------+---------+---------+---------+---------+---------+---------+---------+---------+---------+---------|
genb     GGGAACAGCTGCCAGCTGGGAGACCAAGTGCAATCAACCTGCACGTGCAAAGCCTCCCCTGTGCTTCCACTTGTTGACCCTGGAGGGAATCCTTCGAGGCCCCTGCTATTCCTG
PCR
Consensus 131     140       150       160       170       180       190       200       210       220       230       240       250      260
         |--------+---------+---------+---------+---------+---------+---------+---------+---------+---------+---------+---------+---------|
genb     CTCTGAATTCCAGCAAGGGAGCACCTATGCTGCTGTGGGAGCTGCCAGTTTAACTGGGAATCAAGACCAGGGAACAGTGAGAACAGTGCCAATTTTCACCAGAATTCCTGGAATTCCAGTTGG
PCR
Consensus 261     270       280       290       300       310       320       330       340       350       360       370       380      390
         |--------+---------+---------+---------+---------+---------+---------+---------+---------+---------+---------+---------+---------|
genb     GGCAGGTGGGTTATTAAGGCCTCTGCACGCTCAGTTTCAGTTAAATCTCTCCACACCCCTGGGCCAGGCTGGGCCAAGCCAGGCGGCCCCTGTGTTTTTCCCCAGTCTCTGGGCTGCTGGAGGGAACCAGGTTGT
PCR                                                                   ACCACCCTGGGCCAGGCCAGGCCGGCCCCTGTGTTTTTCCCCAGTCTCTGGGCTGCTGGAGGGAACCAGGTTGT
Consensus                                                             ACCACCCTGGGCCAGGC CAGGC GGCCCCTGTGTTTTTCCCCAGTCTCTGGGCTGCTGGAGGGAACCAGGTTGT 391     400       410       420       430       440       450       460       470       480       490       500       510      520
         |--------+---------+---------+---------+---------+---------+---------+---------+---------+---------+---------+---------+---------|
genb     TTTGGCATCAGCCTCTACTGAGCCGGAGCCCCTTTCCTGCTGCTTTGCATAGTGGCACTAGGCAGCCTCCTCCTCCTCCTCGTCCTCCACCAGGACCTAGGCACTAATTCCGTCCTCCTCCACCAGGCTTCACTTC
PCR      TTTGGCATCAGCCTCTACTGAGCCGGAGCCCCTTTCCTGCTGCTTTGCATAGTGGCACTAGGCAGCCTCCTCCTCCTCCTCGTCCTCCACCAGGACCTAGGCACTAATTCCGTCCTCCTCCACCAGGCTTCACTTC
Consensus TTTGGCATCAGCCTCTACTGAGCCGGAGCCCCTTTCCTGCTGCTTTGCATAGTGGCACTAGGCAGCCTCCTCCTCCTCCTCGTCCTCCACCAGGACCTAGGCACTAATTCCGTCCTCCTCCACCAGGCTTCACTTC 521     530       540       550       560       570       580       590       600       610       620       630       640      650
         |--------+---------+---------+---------+---------+---------+---------+---------+---------+---------+---------+---------+---------|
genb     TCCCCAAGCAGGGTCTCCACCTGCTCTCCACTGCTTGAGGCTGCCCTGGGTTGGGGGAGGCCTTGGCCTTGCTTTACCTTACTCAGACTTTTAAGACAACACAGTTTCCCTGAGACTTTGAAGCTCTCTGTTTATTTA
PCR      TCCCCAAGCAGGGTCTCCACCTGCTCTCCACTGCTTGAGGCTGCCCTGGGTTGGGGGAGGCCTTGGCCTTGCTTTACCTTACTCAGACTTTTAAGACAACACAGTTTCCCTGAGACTTTGAAGCTCTCTGTTTATTTA
Consensus TCCCCAAGCAGGGTCTCCACCTGCTCTCCACTGCTTGAGGCTGCCCTGGGTTGGGGGAGGCCTTGGCCTTGCTTTACCTTACTCAGACTTTT AAGACTTTTTAACACCTCT 651     660       670       680       690       700       710       720       730       740       750       760       770      780
         |--------+---------+---------+---------+---------+---------+---------+---------+---------+---------+---------+---------+---------|
genb     TTTATTTATTTATTTATTTATTATTATTTATTTGAGACAGAGTCTCACTCTGTTGCCCAGACTGGAGTGCAGTGGCACCATCTCGCTCATGCAACCTCCGCCTCCTGAGTTCAAGCAATTCTCCT
PCR
Consensus 781     790       800
         |--------+---------|
genb     GCCTCAGCCTCCAAAGTACC
PCR
Consensus
```

Step 2: Subcloning of Minimal B29 Promoter into pCpG-LacZ (Invivogen)—Creates B29-5 #3.

The minimal −167 human B29 promoter was amplified from a commercial plasmid bearing the full length human B29 promoter (pDrive-hB29; Invivogen) using the following primers: forward 5'-CCAACTAGTGCGACCGCCAAACCTTAGC-3' (SEQ ID NO: 11); reverse: 5'-CAAAAGCTTGACAACGTCCGAGGCTCCTTGG-3' (SEQ ID NO: 12). The resulting PCR fragment was digested with SpeI and HindIII and ligated into the SpeI and HindIII sites of the pCpG-LacZ vector (Invivogen) to create B29-5 #3.

Sequence of B29 Minimal Promoter PCR Fragment (188 bp) in B29-5 #3 (SEQ ID NO: 13)

GCGACCGCCAAACCTTAGCGGCCCAGCTGACAAAAGCCTGCCCTCCCCCA

GGGTCCCCGGAGAGCTGGTGCCTCCCCTGGGTCCCAATTTGCATGGCAGG

AAGGGGCCTGGTGAGGAAGAGGCGGGGAGGGGACAGGCTGCAGCCGGTGC

AGTTACACGTTTTCCTCCAAGGAGCCTCGGACGTTGTC

Alignment of B29 Minimal Promoter PCR Fragment (B29_min) in B29-5 #3 (SEQ ID NO: 13) with Full Length Human B29 Promoter from pDrive-hB29 (SEQ ID NO: 14). The consensus Sequence is Disclosed as SEQ ID NO: 13.

```
                    10         20         30         40         50         60         70         80         90        100        110        120  130
            1    ----+----|----+----|----+----|----+----|----+----|----+----|----+----|----+----|----+----|----+----|----+----|----+----|----+
B29_pron         CCTGCAGGGCCCACTAGTAACGGAGGGTTGTGAGGAGTGGACAGAGGCACCGACGATTTAGCATCTCTTCCTCTCCTGGGGTGCAGGATGAGAGACAAAAAGAAGCTGCCAGGAAAC
B29_nin
Consensus        .................................................................................................................

140        150        160        170        180        190        200        210        220        230        240        250  260
            131  ----+----|----+----|----+----|----+----|----+----|----+----|----+----|----+----|----+----|----+----|----+----|----+----|----+
B29_pron         ATAAAATTCAGAGGAGGGCTGCAGTGCAGGGCTGAGGTCTGCAAGCATGCTGTGTACATTGTGCATGTCTGCCCTGCACAGGAGCATCTGAAGGGCCACACAGAGGCGGGCCAAAGT
B29_nin
Consensus        .................................................................................................................

270        280        290        300        310        320        330        340        350        360        370        380  390
            261  ----+----|----+----|----+----|----+----|----+----|----+----|----+----|----+----|----+----|----+----|----+----|----+----|----+
B29_pron         GAGTTTATATCAGTTCCTGAGCACTGTGCTCCATCCAGCACTCTGAGACACAGCAGGATACAGCTGAGGACCTGAGGGCTCCCCCACCACCAGCTCCTGTTCCCTGCCAAAGACCCCTGGACCTGCAG
B29_nin
Consensus        .................................................................................................................

400        410        420        430        440        450        460        470        480        490        500        510  520
            391  ----+----|----+----|----+----|----+----|----+----|----+----|----+----|----+----|----+----|----+----|----+----|----+----|----+
B29_pron         ACAACAATTCAACGCACTCAGAGTTCCCACAGTTAAGAACTCCCTGAAGAACCCCCAGTGGCTGCCTGGTGGATTTTCCAAAGCTGTCTCCACTACATCCACCCTGTTTGCAGCCCTACATACTCT
B29_nin
Consensus        .................................................................................................................

530        540        550        560        570        580        590        600        610        620        630        640  650
            521  ----+----|----+----|----+----|----+----|----+----|----+----|----+----|----+----|----+----|----+----|----+----|----+----|----+
B29_pron         TTCACAGCATGAGAAGGAGGCCTCTCACCAAGAACCTGACTGAATTCTTCTCCAGAACCTGACTCTTGCTGCCACACCTGTGTCCAGTGGTGCCACAACCTCTGTTGTCCAGAGGGTCAACTTCCAAC
B29_nin
Consensus        .................................................................................................................

660        670        680        690        700        710        720        730        740        750        760        770  780
            651  ----+----|----+----|----+----|----+----|----+----|----+----|----+----|----+----|----+----|----+----|----+----|----+----|----+
B29_pron         ATGGCTGCCTGCTGCTCCAGCAGCCTGCTGCTCTCGGGCCCCCTCCAGATGCCTGACCTGGGTGTGGCTGCCGCCCTGTCTCCTTCCCGCTGCTCTTCCCGCTGCTCTTCAGTGCTCCCGTCTGAGGTGAGGAATAGTTCAGGAGGACAGAGG
B29_nin
Consensus        .................................................................................................................
```

-continued

```
                781  790       800       810       820       830       840       850       860       870       880       890       900       910
                |----+---------+---------+---------+---------+---------+---------+---------+---------+---------+---------+---------+---------+----|
B29_pron        AGCTAAGTTCAGGTTCATTCATAGGACAGGTGCTGCCTATTTCGTTCGTTCGCCGGCCCAGGAATAGAGACTTGCCGGCTCGGCTTCGGGGAGTTGCCCCCTTCGCGGAGTTGGCAGACGAGAGGGGAGCATGCTGCTGCCCAGGGGATGA
B29_nin
Consensus       ................................................................................................................................................

911  920       930       940       950       960       970       980       990       1000      1010      1020      1030      1040
                |----+---------+---------+---------+---------+---------+---------+---------+---------+---------+---------+---------+---------+----|
B29_pron        CCACCGGGTGGGTAAGCACAGAGAGGGAGCACAGGCTTCCCCCAAGAAGACTGAGAGGCCCCCAGAGGCATCCACAGAGGAGGCACCCCCAGCTGTGCTGCCCAAGCTGGGCGACCGCCAAGCTTAGCGGC
B29_nin                                                                                                                     GCGACCGCCAAACCTTAGCGGC
Consensus       .....................................................................................................................GCGACCGCCAAACCTTAGCGGC 1041 1050      1060      1070      1080      1090      1100      1110      1120      1130      1140      1150      1160      1170
                |----+---------+---------+---------+---------+---------+---------+---------+---------+---------+---------+---------+---------+----|
B29_pron        CCAGCTGACAAAAGCCTGCCCTCCCCAGGTCCCCAGGGTCCTGGTGCCTCCCCTGGTCCATTTGCATGCAGGCAGGAAGGGCCTGGTGAGGAAGAGGCGGGAGGGGCAGGCTGCAGCCGTGCAG
B29_nin         CCAGCTGACAAAAGCCTGCCCTCCTCCTCCCCAGGGTCCCTGGTGCCTCCCCTGGTCCAATTTGCATGCAGGCAGGAAGGGCCTGGTGAGGAAGAGGCGGGAGGGGCAGGCTGCAGCCGTGCAG
Consensus       CCAGCTGACAAAAGCCTGCCCTCC.CC.CCCCAGG.TCC.TGGTGCCTCCCCTGGTCCAATTTGCATGCAGGCAGGAAGGGCCTGGTGAGGAAGAGGCGGGAGGGGCAGGCTGCAGCCGTGCAG 1171 1180      1190      1200      1210      1220      1230 1237
                |----+---------+---------+---------+---------+---------+----+---|
B29_pron        TTACACGTTTTCCTCCAAGGAGCCTCGGACGTTGTCAGGGTTTGGGGTCGGGGACAGAGCGGTGAC
B29_nin         TTACACGTTTTCCTCCAAGGAGCCTCGGAGCCTCGGACGTTGTC
Consensus       TTACACGTTTTCCTCCAAGGAGCCTCGGACGTTGTC.............................
```

Step 3: Subcloning of HA-eIF5A1$^{K50R}$ into B29-5 #3 Vector—Creates pB29-eIF5A1K50R_7.

HA-eIF5A1$^{K50R}$ was amplified by PCR using the pHM6-eIF5A1$^{K50R}$ as a DNA template and the following primers: forward 5'-CGCCATGGACATGTACCCTTACGACGTC-CCAGACTACGCTGCAGATGATTTGGACTTCGAG-3' (SEQ ID NO: 15) and reverse 5'-CGC GCTAGCCAGTTATTTTGCCATCGCC-3' (SEQ ID NO: 16). The resulting PCR fragment was digested with NcoI and NheI and subcloned into the NcoI and NheI sites of B29-5 #3 to replace LacZ.

Sequence of HA-eIF5A1$^{K50R}$ PCR Fragment (497 bp) in pB29-eIF5A1K50R_7 (SEQ ID NO: 17)

```
ACATGTACCCTTACGACGTCCCAGACTACGCTGCAGATGATTTGGACTTC
GAGACAGGAGATGCAGGGGCCTCAGCCACCTTCCCAATGCAGTGCTCAGC
ATTACGTAAGAATGGTTTTGTGGTGCTCAAGGGCCGGCCATGTAAGATCG
TCGAGATGTCTACTTCGAAGACTGGCAGGCATGGCCATGCCAAGGTCCAT
CTGGTTGGCATTGATATTTTTACTGGGAAGAAATATGAAGATATCTGCCC
GTCGACTCATAACATGGATGTCCCCAACATCAAAAGGAATGATTTCCAGC
TGATTGGCATCCAGGATGGGTACCTATCCCTGCTCCAGGACAGTGGGGAG
GTACGAGAGGACCTTCGTCTGCCTGAGGGAGACCTTGGCAAGGAGATTGA
GCAGAAGTATGACTGTGGAGAAGAGATCCTGATCACAGTGCTGTCCGCCA
TGACAGAGGAGGCAGCTGTTGCAATCAAGGCGATGGCAAAATAACTG
```

Translation of HA-eIF5A1$^{K50R}$ PCR Fragment in pB29-eIF5A1K50R_7 (SEQ ID NO: 18)
HA Epitope
eIF5A1$^{K50R}$
K50R MD<u>MYPYDVPDY</u>AADDLDFETGDAGASATFPMQCSALRKNGFVVLKGRPCK

IVEMSTSKTGRHGHAKVHLVGIDIFTGKKYEDICPSTHNMDVPNIKRNDF

QLIGIQDGYLSLLQDSGEVREDLRLPEGDLGKEIEQKYDCGEEILITVLS

AMTEEAAVAIKAMAK

Alignment of HA-eIF5A1$^{K50R}$ PCR Fragment in pB29-eIF5A1K50R_7 (SEQ ID NO: 18) with Human eIF5A1 (Accession #NP_001961 (SEQ ID NO: 19)). The Consensus Sequence is Disclosed as Residues 12-165 of SEQ ID NO: 18.

```
                    1         10        20        30        40        50        60        70        80
                    |---------+---------+---------+---------+---------+---------+---------+---------+--------
          eIF5A                 MADDLDFETGDAGASATFPMQCSALRKNGVVLKGRPCKIVEMSTSKTGKHGHAKVHLVGIDIFTGKKYEDICPSTHN
       HA-5A-K50R    MDMYPYDVPDYAADDLDFETGDAGASATFPMQCSALRKNGVVLKGRPCKIVEMSTSKTGKHGHAKVHLVGIDIFTGKKYEDICPSTHN
       Consensus    ...........aADDLDFETGDAGASATFPMQCSALRKNGVVLKGRPCKIVEMSTSKTGKHGHAKVHLVGIDIFTGKKYEDICPSTHN 90        100       110       120        130 131      140       150       160  165
                   +---------+---------+---------+---------+---------||--------+---------+---------+----|
         eIF5A     MDVPNIKRNDFQLIGIQDGYLSLLQDS6EVREDLRLPEGDLGKEIEQKYDCGEEILITVLSAMTEEAAVAIKAMAK
      HA-5A-K50R   MDVPNIKRNDFQLIGIQDGYLSLLQDS6EVREDLRLPEGDLGKEIEQKYDCGEEILITVLSAMTEEAAVAIKAMAK
      Consensus    MDVPNIKRNDFQLIGIQDGYLSLLQDS6EVREDLRLPEGDLGKEIEQKYDCGEEILITVLSAMTEEAAVAIKAMAK
```

Step 4: Creation of New Multiple Cloning Site in pCpG-mcs (Invivogen)—Creates pCpG-Linker4.

The pCpG cloning vector, pCpG-mcs G2 (Invivogen), was digested with EcoRI to remove the mammalian expression cassette containing the mCMV enhancer, the hEF1 promoter, the synthetic intron, the multiple cloning site, and the SV40 polyadenylation signal. The EcoRI-digested pCpG-mcs G2 vector was then ligated to a synthetic linker with EcoRI sticky ends to create a promoterless vector with a new multiple cloning site (pCpG-Linker4). SEQ ID NOS 20-21 are disclosed below, respectively, in order of appearance.

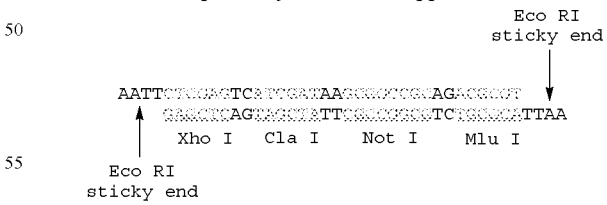

Synthetic linker, Linker4 with two Eco RI sticky ends

Sequence of Region Surrounding New Multiple Cloning Site in pCpG-Linker4 (SEQ ID NO: 22)

```
  1  GGCATGTGAACTGGCTGTCTTGGTTTTCATCTGTACTTCATCTGCTACCT   50
 51  CTGTGACCTGAAACATATTTATAATTCCATTAAGCTGTGCATATGATAGA  100
```

```
  101  TTTATCATATGTATTTTCCTTAAAGGATTTTTGTAAGAACTAATTGAATT   150

151  GATACCTGTAAAGTCTTTATCACACTACCCAATAAATAATAAATCTCTTT   200

201  GTTCAGCTCTCTGTTTCTATAAATATGTACAAGTTTTATTGTTTTTAGTG   250

251  GTAGTGATTTTATTCTCTTTCTATATATATACACACACATGTGTGCATTC   300

301  ATAAATATATACAATTTTTATGAATAAAAAATTATTAGCAATCAATATTG   350

351  AAAACCACTGATTTTTGTTTATGTGAGCAAACAGCAGATTAAAAGGAATT   400

401  CTCGAGTCATCGATAAGCGGCCGCAGACGCGTAATTCAGTCAATATGTTC   450

451  ACCCCAAAAAAGCTGTTTGTTAACTTGCCAACCTCATTCTAAAATGTATA   500

501  TAGAAGCCCAAAAGACAATAACAAAAATATTCTTGTAGAACAAAATGGGA   550

551  AAGAATGTTCCACTAAATATCAAGATTTAGAGCAAAGCATGAGATGTGTG   600

601  GGGATAGACAGTGAGGCTGATAAAATAGAGTAGAGCTCAGAAACAGACCC   650

651  ATTGATATATGTAAGTGACCTATGAAAAAAATATGGCATTTTACAATGGG   700

701  AAAATGATGATCTTTTTCTTTTTAGAAAAACAGGGAAATATATTTATAT   750

751  GTAAAAAATAAAAGGGAACCCATATGTCATACCATACACACAAAAAAAAT   800

801  TCCAGTGAATTATAAGTCTAAATGGAGAAGGCAAAACTTTAAATCTTTTA   850

851  GAAAATAATATAGAAGCATGCCATCAAGACTTCAGTGTAGAGAAAAATTT   900

901  CTTATGACTCAAAGTCCTAACCACAAAGAAAAGATTGTTAATTAGATTGC   950

951  ATGAATATTAAGACTTATTTTTAAAATTAAAAAACCATTAAGAAAAGTCA  1000

1001  GGCCATAGAATGACAGAAAATATTTGCAAC                     1030
```

The numbering of the sequence above is for ease of reference to the following features: βGlo MAR (nucleotides 1-380); EcoRI recognition sequence (nucleotides 396-401); XhoI recognition sequence (nucleotides 401-406); ClaI recognition sequence (nucleotides 409-414); NotI recognition sequence (nucleotides 417-424); MluI recognition sequence (nucleotides 427-432); IFNβ S/MAR (nucleotides 438-1,030).

Step 5: Subcloning of B29 DS4.4 3' Enhancer into pCpG-Linker4—Creates pCpG-DHS4.4.

The B29 DHS4.4 3' enhancer was amplified by PCR using pGEM-4.4enh #8 as a template and the following primers: forward 5'-GAAGCGGCCGCACCACCCTGGGCCAGGCTGG-3' (SEQ ID NO: 23); and reverse 5'-CCACGCGTAGAGGTGTTAAAAAGTCTTTAGGTAAAG-3' (SEQ ID NO: 24). The resulting PCR fragment was digested with NotI and MluI and ligated into the NotI and MluI sites in the new multiple cloning site of pCpG-Linker4 to create pCpG-DHS4.4.

>pCpG-DHS4.4 full-length sequences (2,282 bp (SEQ ID NO: 25))

```
   1  TTAATTAAAATTATCTCTAAGGCATGTGAACTGGCTGTCTTGGTTTTCAT    50

51  CTGTACTTCATCTGCTACCTCTGTGACCTGAAACATATTTATAATTCCAT   100

101  TAAGCTGTGCATATGATAGATTTATCATATGTATTTTCCTTAAAGGATTT   150

151  TTGTAAGAACTAATTGAATTGATACCTGTAAAGTCTTTATCACACTACCC   200

201  AATAAATAATAAATCTCTTTGTTCAGCTCTCTGTTTCTATAAATATGTAC   250

251  AAGTTTTATTGTTTTTAGTGGTAGTGATTTTATTCTCTTTCTATATATAT   300

301  ACACACACATGTGTGCATTCATAAATATATACAATTTTTATGAATAAAAA   350

351  ATTATTAGCAATCAATATTGAAAACCACTGATTTTTGTTTATGTGAGCAA   400

401  ACAGCAGATTAAAAGGAATTCTCGAGTCATCGATAAGCGGCCGCACCACC   450

451  CTGGGCCAGGCTGGGCCAAGCCAGGCGGCCCCTGTGTTTTCCCCAGTCTC   500

501  TGGGCTGCTGGAGGGAACCAGGTTGTTTTGGCATCAGCCTCTACTGAGCC   550

551  GGAGCCCTTCCTTTCCTGCTGCTTTGCATAGTGGCACTAATTCCGTCCTC   600
```

```
-continued
 601 CTACCTCCACCAGGGACCTAGGCAGCCGGGTAGATGGTGGGAGGAGGCTT   650

651 CACTTCTCCCCCAAGCAGGGTCTCCACCTGCTTGAGGCTGCCCTGGGTTG   700

701 GGGGAGGCCTTGGCTTTACCTAAAGACTTTTTAACACCTCTACGCGTAAT   750

751 TCAGTCAATATGTTCACCCCAAAAAAGCTGTTTGTTAACTTGCCAACCTC   800

801 ATTCTAAAATGTATATAGAAGCCCAAAAGACAATAACAAAAATATTCTTG   850

851 TAGAACAAAATGGGAAAGAATGTTCCACTAAATATCAAGATTTAGAGCAA   900

901 AGCATGAGATGTGTGGGGATAGACAGTGAGGCTGATAAAATAGAGTAGAG   950

951 CTCAGAAACAGACCCATTGATATATGTAAGTGACCTATGAAAAAAATATG  1000

1001 GCATTTTACAATGGGAAAATGATGATCTTTTCTTTTTTAGAAAAACAGG   1050

1051 GAAATATATTTATATGTAAAAAATAAAAGGGAACCCATATGTCATACCAT  1100

1101 ACACACAAAAAAATTCCAGTGAATTATAAGTCTAAATGGAGAAGGCAAAA  1150

1151 CTTTAAATCTTTTAGAAAATAATATAGAAGCATGCCATCAAGACTTCAGT  1200

1201 GTAGAGAAAAATTTCTTATGACTCAAAGTCCTAACCACAAAGAAAAGATT  1250

1251 GTTAATTAGATTGCATGAATATTAAGACTTATTTTTAAAATTAAAAAACC  1300

1301 ATTAAGAAAAGTCAGGCCATAGAATGACAGAAAATATTTGCAACACCCCA  1350

1351 GTAAAGAGAATTGTAATATGCAGATTATAAAAAGAAGTCTTACAAATCAG  1400

1401 TAAAAAATAAAACTAGACAAAAATTTGAACAGATGAAAGAGAAACTCTAA  1450

1451 ATAATCATTACACATGAGAAACTCAATCTCAGAAATCAGAGAACTATCAT  1500

1501 TGCATATACACTAAATTAGAGAAATATTAAAAGGCTAAGTAACATCTGTG  1550

1551 GCTTAATTAAAACAGGTAGTTGACAATTAAACATTGGCATAGTATATCTG  1600

1601 CATAGTATAATACAACTCACTATAGGAGGGCCATCATGGCCAAGTTGACC  1650

1651 AGTGCTGTCCCAGTGCTCACAGCCAGGGATGTGGCTGGAGCTGTTGAGTT  1700

1701 CTGGACTGACAGGTTGGGGTTCTCCAGAGATTTTGTGGAGGATGACTTTG  1750

1751 CAGGTGTGGTCAGAGATGATGTCACCCTGTTCATCTCAGCAGTCCAGGAC  1800

1801 CAGGTGGTGCCTGACAACACCCTGGCTTGGGTGTGGGTGAGAGGACTGGA  1850

1851 TGAGCTGTATGCTGAGTGGAGTGAGGTGGTCTCCACCAACTTCAGGGATG  1900

1901 CCAGTGGCCCTGCCATGACAGAGATTGGAGAGCAGCCCTGGGGGAGAGAG  1950

1951 TTTGCCCTGAGAGACCCAGCAGGCAACTGTGTGCACTTTGTGGCAGAGGA  2000

2001 GCAGGACTGAGGATAACCTAGGAAACCTTAAAACCTTTAAAAGCCTTATA  2050

2051 TATTCTTTTTTTCTTATAAAACTTAAAACCTTAGAGGCTATTTAAGTTG   2100

2101 CTGATTTATATTAATTTTATTGTTCAAACATGAGAGCTTAGTACATGAAA  2150

2151 CATGAGAGCTTAGTACATTAGCCATGAGAGCTTAGTACATTAGCCATGAG  2200

2201 GGTTTAGTTCATTAAACATGAGAGCTTAGTACATTAAACATGAGAGCTTA  2250

2251 GTACATACTATCAACAGGTTGAACTGCTGATC   2282
```

The numbering of the sequence above is for ease of reference to the following features: βGlo MAR (nucleotides 1-400); EcoRI recognition sequence (nucleotides 416-421); XhoI recognition sequence (nucleotides 421-426); ClaI recognition sequence (nucleotides 429-434); NotI recognition sequence (nucleotides 437-444); DHS4.4 (nucleotides 445-741); MluI recognition sequence (nucleotides 742-747); IFNβ S/MAR (nucleotides 753-1,569).

Step 6: Subcloning of B29 Promoter+HA-eIF5A1$^{K50R}$+ SV40 pA Expression Cassette into pCpG-DHS4.4—Creates pExp-5.

The B29-eIF5A1 expression cassette containing the minimal B29 promoter, the synthetic intron, HA-eIF5A1$^{K50R}$, and the SV40 pA, was amplified from pB29-eIF5A1K50R__7 (Step 3) by PCR using the following primers: forward 5'-GT-TATCGATACTAGTGCGACCGCCAAACC-3' (SEQ ID NO: 26); and reverse 5'-CAAGCGGCCGCCATACCA-CATTTGTAGAGGTTTTAC-3' (SEQ ID NO: 27). The resulting PCR fragment was digested with ClaI and NotI and subcloned into the ClaI and NotI sites in the multiple cloning site of pCpG-DHS4.4 to create pExp-5.

Step 7: Replacement of HA-eIF5A1$^{K50R}$ in pExp-5 with Non-HA eIF5A1$^{K50R}$ Creates Final Vector, pExp5A.

The pExp-5 plasmid was digested with NcoI and NheI to remove HA-eIF5A1$^{K50R}$. A non-HA-tagged eIF5A1$^{K50R}$ PCR fragment was amplified from pHM6-eIF5A1$^{K50R}$ by PCR using the following primers: forward 5'-CACCATG-GCAGATGATTTGGACTTC-3' (SEQ ID NO: 28); and reverse 5'-CGCGCTAGCCAGTTATTTTGCCATCGCC-3' (SEQ ID NO: 16). The resulting PCR product was digested with NcoI and NheI and ligated into the NcoI and NheI sites of B29-5 #3 to generate B29-K50R. B29-K50R was digested with NcoI and NheI and the 470 bp eIF5A1$^{K50R}$ fragment was gel purified and ligated to NcoI/NheI-digested pExp-5 to generate the final expression vector, pExp5A.

Example 18

Testing of pExp5A

Figure 24B:
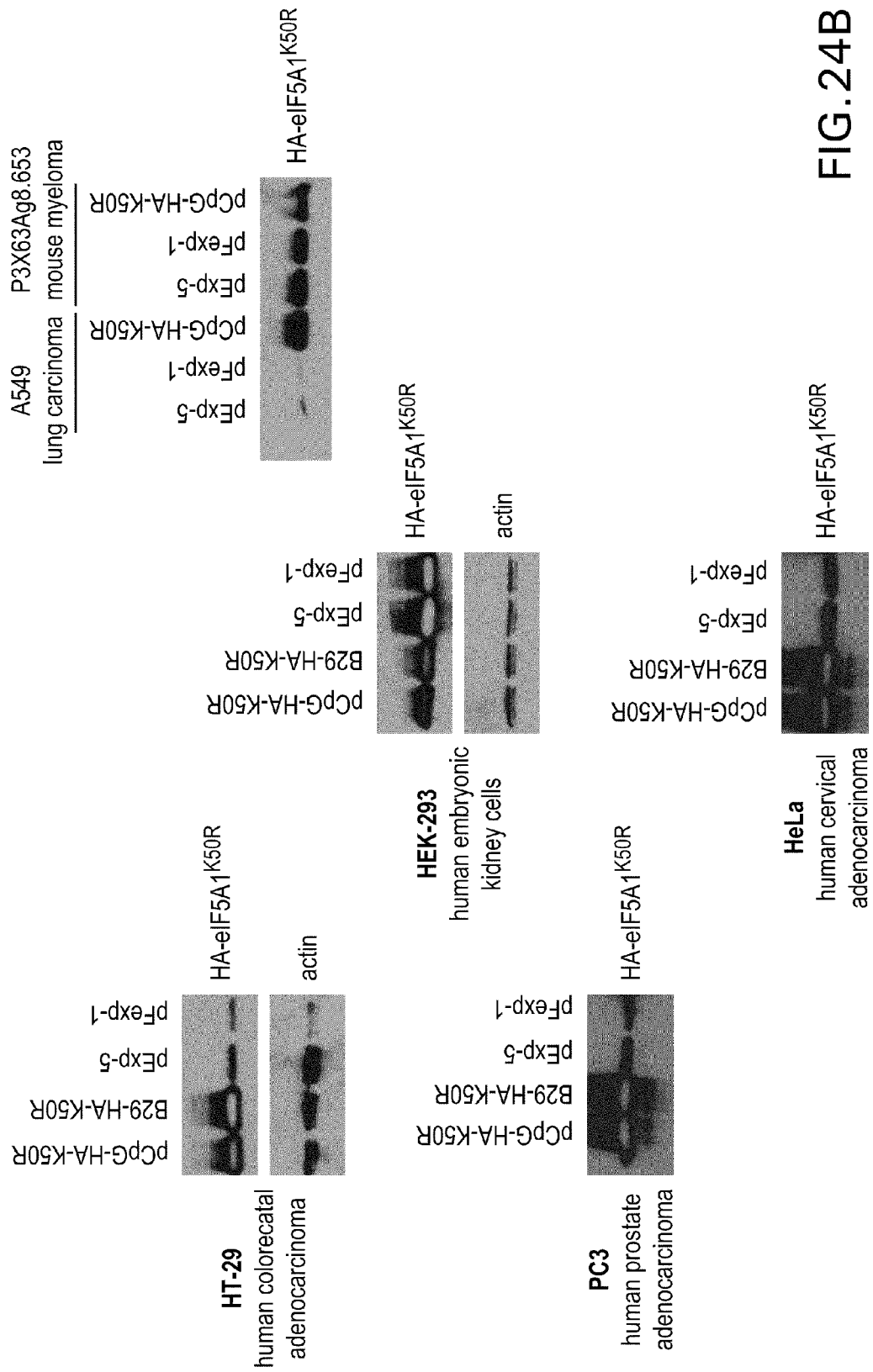
FIG. 24 shows the rexpression of eIF5A1$^{K50R}$ in various cell lines. See example 18.

Various cell lines were transfected with plasmids using Lipofectamine 2000 and expression of HA-eIF5A1K50R was determined 24 hours following transfection by Western blotting with an anti-HA antibody (Roche). Different cells lines tested were P3X63Ag8.653 (mouse B lymphoblast—myeloma), KAS (human myeloma), HepG2 (huma liver hepatocellular carcinoma), T24 (human bladder carcinoma); HT-29 (human colorectal adenocarcinoma), HEK-293 (human embryonic kidney cells), PC3 (human prostate adenocarcinoma); HeLa (human cervical adenocarcinoma), and A549 (lung carcinoma). See FIG. 24.

pExp-5 plasmid expresses HA-eIF5A1$^{K50R}$ in both human and mouse myeloma cell lines at comparable levels to a plasmid with the constitutive EF1 promoter (CpG-eIF5A1$^{K50R}$). However expression of HA-eIF5A1$^{K50R}$ driven by pExp-5 is limited in non-B cell lines compared to expression by a constitutive promoter. The one exception was in HEK-293 cells, a human embryonic kidney cell line where high levels of HA-eIF5A1$^{K50R}$ expression was observed following pExp-5 transfection—this may be due to the embryonic nature of the cell line; at this time we do not know if pExp-5 expresses in adult kidney cells. The final plasmid for use in toxicity studies and clinical trial will be a version of pExp-5 in which HA-eIF5A1$^{K50R}$ has been replaced by non-HA tagged eIF5A1$^{K50R}$ (pExp5A). pExp-5 contains HA-tagged eIF5A1$^{K50R}$ under the control of the minimal human B29 promoter/enhancer; expression of HA-eIF5A1$^{K50R}$ was compared to that driven by plasmids with constitutive expression as well as to a plasmid containing the full-length B29 promoter Example 19

Formation of In Vivo JETPEI™ Nanoparticle

This example given is for formation of the in vivo JET-PEI™ nanoparticle complex for injection into 20 g mouse for a dose of 1.5 mg/kg (0.1 mL)—1.5 mg/kg=1.0 mg pExp5A/kg+0.5 mg h5A1/kg—DNA:siRNA ratio=2:1.

Dilute plasmid DNA and siRNA into a total volume of 25 ml. Use sterile water to adjust the volume. * Dilute 20 mg of plasmid DNA (10 ml at 2 mg/ml) and 10 mg of siRNA (10 ml at 1 mg/ml) into a total volume of 25 ml. Use sterile water to make up difference. Adjust the volume of DNA solution to 50 ml 5% glucose by adding 25 ml of 10% glucose (provided with PEI kit). Vortex gently and centrifuge briefly. Dilute in vivo JETPEI™ into a total volume of 25 ml of water. * Dilute 3.6 ml of in vivo JETPEI™ into a total volume of 25 ml of water. Adjust final volume to 50 ml with 10% glucose to end up with a final concentration of 5% glucose. Vortex gently and centrifuge briefly. Immediately add 50 ml of diluted PEI to the 50 ml of diluted DNA (do not reverse the order!). Vortex briefly and immediately spin down.

After formation the complex is stable for 8 to 10 hours. The N/P ratio of the complex should be 6. The N/P ratio is the ratio of the number of positively charged nitrogen residues of in vivo-jetPEI to the number of negatively charged phosphate residues of DNA and siRNA. DNA and siRNA contain the same number of phosphate groups per gram. The N/P ratio is therefore a measure of the ionic balance within the complex. Increasing the N/P ratio of the complex can increase the toxicity of the complex. In vivo JET-PEI is provided as a 150 mM solution (expressed as nitrogen residues) while DNA contains 3 nmoles of anionic phosphate in 1 mg. The final concentration of DNA in the final volume should not exceed 0.5 mg/ml. The DNA should be of high quality and prepared in water. In vivo-jetPEI and 10% glucose should be brought to room temperature prior to use.

Example 20

Figure 22:
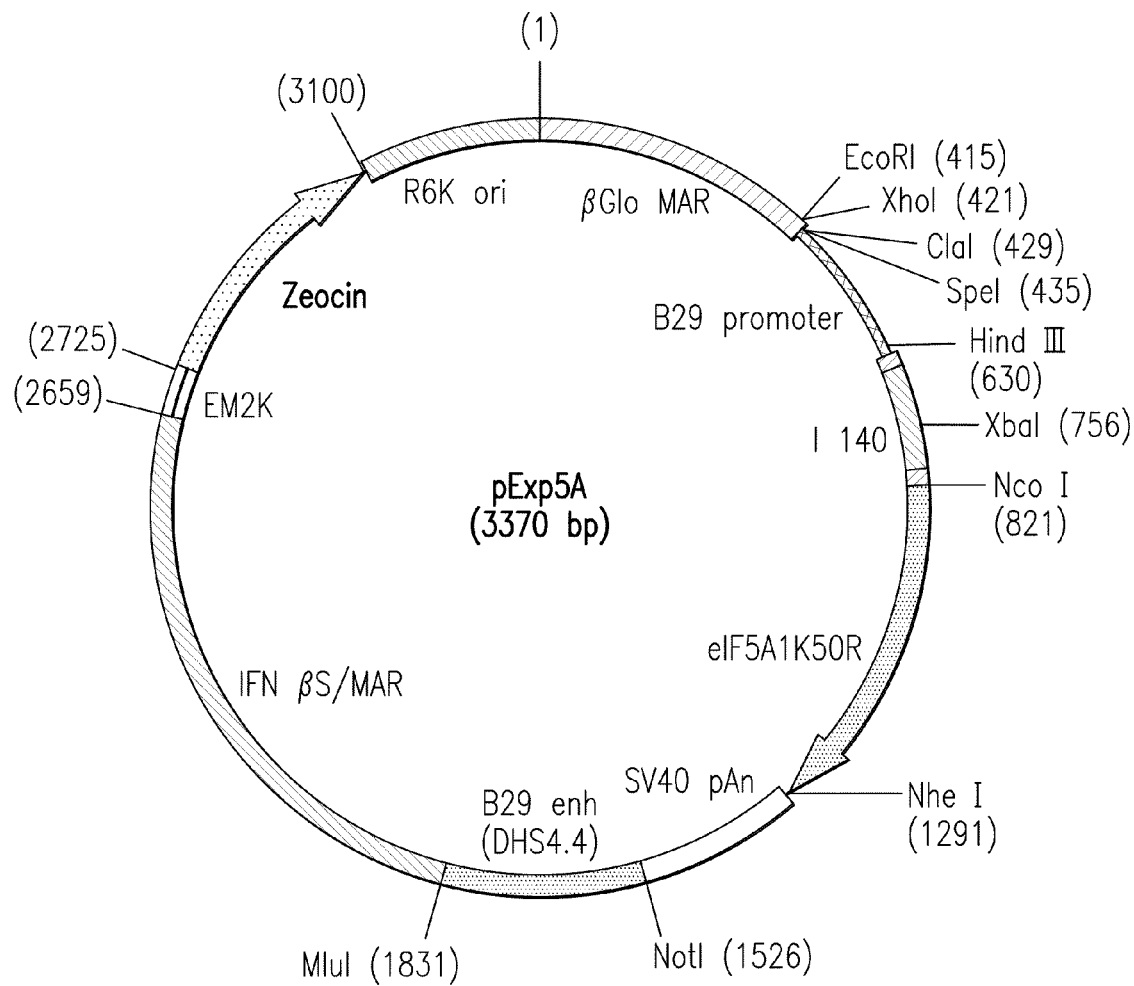
FIG. 22 shows the map of pExp5A, the construction of which is described in Example 17.

Dose Range-Finding and Repeat Dose Studies with Intra-Venous SNS01 and SNS-EF1/UU in Mice SNS01 is one embodiment of the present invention—it is a cancer therapy biologic targeted to the treatment of multiple myeloma. SNS01 is comprised of three components: a DNA vector expressing a pro-apoptotic mutant of eIF5A (see FIG. 22); an siRNA that targets the native eIF5A that promotes growth/anti-apoptosis of cancer cells (see the sequence in FIG. 25); and a synthetic polymer called polyethylenimine (In vivo-jetPEI; Polyplus Transfection Inc.) that acts as a delivery vehicle.

The purpose of the studies was to determine the maximum tolerated dose and the feasibility of long-term administration of therapeutic doses of intra-venous SNS01 into mice. Two separate studies were performed. The maximum tolerated dose (Study ID: MTD) study was an 8-day study in which mice received two intra-venous doses of increasing amounts of SNS01 (from 2.2 mg/kg to 3.7 mg/kg) and toxicity was assessed by monitoring clinical signs, body weight, organ weight and liver enzymes. The 9-week repeated dose study (Study ID: EX6) was a study designed to assess toxicity following long-term administration of twice-weekly therapeutic doses (1.5 mg/kg) of SNS-EF1/UU and as well as it's various components. SNS-EF1/UU is a preclinical version of SNS01 and differs mainly in that expression of eIF5A$^{K50R}$ is driven by a constitutive promoter (one that expresses in all tissues at all times) rather than a B-cell-specific promoter as in the SNS01 complex. The use of the B cell-specific B29 promoter in SNS01 was designed to enhance the safety of the therapeutic by limiting expression of the pro-apoptotic eIF5A mutant to cells of B-cell origin, including myeloma cells. The EX6 study also included a group of mice that were dosed with a mouse-specific eIF5A siRNA to determine whether there were any toxic effects of suppressing eIF5A in mouse tissues. Toxicity in the repeated dose study was assessed by monitoring clinical signs, body weight, hematology, liver enzymes, as well as histopathology.

| Study ID | Animal Model | Injection Schedule | Duration of Treatment | Test Article |
|---|---|---|---|---|
| MTD | CD-1 (female) | Twice weekly Intra-venous | 8-Days (2 injections) | SNS01 |
| EX6 | Balb/c (female) | Twice weekly Intra-venous | 9-Weeks | SNS-EF1/UU SNS-EF1/UU components tested individually Mouse eIF5A siRNA |

| Test Article | Plasmid DNA | siRNA | Vehicle | Material Grade |
|---|---|---|---|---|
| SNS01[a] | pExp5A[c] (eIF5A$^{K50R}$ expression driven by B29 B-cell-specific promoter) | eIF5A siRNA (dTdT overhang[d]) human-specific eIF5A siRNA | In vivo-jetPEI™ | GLP-grade materials |
| SNS-EF1/UU[b] | pCpG-HA-eIF5A$^{K50R}$ (HA-eIF5A$^{K50R}$ expression driven by ubiquitous EF1 promoter) | h5A1 (UU overhang[d]) human-specific eIF5A siRNA | In vivo-jetPEI™ | Research-grade materials |

[a] SNS01 contains GLP-grade materials and is being developed for the clinic
[b] SNS-EF1/UU is a test article used in preclinical research that led to the development of SNS01
[c] the pExp5A plasmid is RNAi-resistant due to the fact that the plasmid contains only the open reading frame of eIF5A while the eIF5A siRNA (h5A1) targets the 3' UTR of eIF5A
[d] the sequence of the SNS01 eIF5A siRNA and the h5A1 siRNA are identical except for the presencee of a dTdT overhang rather than a UU overhang on the 3' terminal ends of the siRNA; the dTdT overhang does not affect the target selectivity or efficacy of the siRNA but has been proposed to enhance stability Preclinical experiments have indicated that SNS01 is therapeutic at doses of 0.75 mg/kg to 1.5 mg/kg (Study EX9). In the 8-day dose range-finding study (Study ID: MTD) significantly higher doses than the therapeutic range was tested to determine the upper limit of the dose range. Twice-weekly intra-venous doses of the test article was well tolerated at the lower dose levels of 2.2 mg/kg and 2.9 mg/kg although one mouse reached morbidity at the 2.9 mg/kg and was euthanized. Doses at 3.3 mg/kg or above resulted in survival rates of approximately 20-25%. Therefore, the maximum tolerated dose is between 2.2 mg/kg and 2.9 mg/kg and is well above the therapeutic range of 0.75 mg/kg to 1.5 mg/kg.

In the 9-week repeated dose study (Study ID: EX6) the mice received twice weekly tail vein injections of therapeutic doses (1.5 mg/kg) of SNS-EF1/UU and no test article-related toxic effects were observed over the period of the study. The DNA and siRNA were also tested separately in this study and both were well tolerated by the mice. Since the human eIF5A siRNA is not active in mice, a mouse eIF5A-specific siRNA was also included in this study. No toxic effects related to chronic administration of the mouse eIF5A siRNA were observed over the 9-week period. These results indicate that therapeutic doses of SNS01 and SNS-EF1/UU are non-toxic to mice even when administered over long periods.

Test Article and Vehicle

| Test Article | Manufacturer of Plasmid DNA component | Manufacturer of siRNA component | Manufacturer of PEI component | Formation of Test Article |
|---|---|---|---|---|
| SNS01 | VGXI Lot # pExp5A.08L007 | Avecia | Polyplus Transfection Inc GLP-Grade | Components were combined with 10% glucose to form nano—complexes; complexes were injected within 2-4 hours |
| SNS-EF1/UU | Qiagen EndoFree Plasmid Mega Kit <0.1 EU/μg DNA | ThermoScientific Dharmacon RNAi Technologies | Polyplus Transfection Inc. Research-Grade | Components were combined with 10% glucose to form nano-complexes; complexes were injected |

-continued

| Test Article | Manufacturer of Plasmid DNA component | Manufacturer of siRNA component | Manufacturer of PEI component | Formation of Test Article |
|---|---|---|---|---|
| Storage Conditions (Stability) | −20° C. (≧1 year) | −20° (≧1 year) | 4° (≧1 year) | within 2-4 hours Room Temperature (≧6 hours) |

Test Systems and Study Designs

All aspects of this study were conducted in accordance with the guidelines set out by the University of Waterloo Animal Care Committee (Waterloo, Ontario, Canada) as established by the Canadian Council on Animal Care and the Province of Ontario Animals for Research Act.

The CD-1 and BALB/c mice were obtained from Charles River Laboratories (Quebec, Canada). Mice from both studies received the test article twice-weekly via tail vein intravenous injections. Slow injections (~2-3 minutes) were used to deliver volumes greater than 0.2 ml.

The mice for the 8-day study were approximately 6-9 weeks old at the start of study. The mice for the 9-week repeated dose study were approximately 5-6 weeks old at the initiation of the study.

STUDY ID: MTD

| Group | No. Animals (female) | Test Article | N/P ratio[a] | Dose level (mg/kg) | Injection Volume | Total # injections |
|---|---|---|---|---|---|---|
| MTD-C | 5 | 5% Glucose | — | — | 0.33 mL | 2 |
| MTD-PA | 5 | SNS01 | 6 | 2.2 mg/kg | 0.20 mL | 2 |
| MTD-PB | 5 | SNS01 | 6 | 2.9 mg/kg | 0.27 mL | 2 |
| MTD-PC | 4 | SNS01 | 6 | 3.3 mg/kg | 0.30 mL | 1[b] |
| MTD-PD | 5 | SNS01 | 6 | 3.7 mg/kg | 0.33 mL | 1[b] |

[a]N/P ratio = ratio of positively-charged nitrogens on PEI to the negatively-charged phosphate groups of the nucleic acids
[b]due to toxicity the surviving mice were not given a second injection

STUDY ID: EX6

| Group | No. Animals (female) | Test Article | N/P ratio | Dose level (mg/kg) | Injection Volume | Total # injections |
|---|---|---|---|---|---|---|
| Ex6-G1 | 4 | 5% Glucose | — | — | 0.10 mL | 20 |
| Ex6-G2 | 5 | Vehicle Control[a] | 8 | 1.5 mg/kg | 0.10 mL | 20 |
| Ex6-G3 | 5 | siRNA[b] | 8 | 1.5 mg/kg | 0.10 mL | 20 |
| Ex6-G4 | 6 | DNA[c] | 8 | 1.5 mg/kg | 0.10 mL | 20 |
| Ex6-G5 | 4 | SNS-EF1/UU | 8 | 1.5 mg/kg | 0.10 mL | 20 |
| Ex6-G6 | 6 | Mouse siRNA[d] | 8 | 1.5 mg/kg | 0.10 mL | 20 |

[a]PEI complex containing a non-expressing plasmid (same vector background as pExp5A) and a non-targeting siRNA
[b]PEI complex containing a non-expressing plasmid (same vector background as pExp5A) and the h5A1 siRNA
[c]PEI complex containing pCpG-HA-eIF5A$^{K50R}$ plasmid and a non-targeting siRNA
[d]PEI complex containing a non-expressing plasmid (same vector background as pExp5A) and a mouse-specific eIF5A siRNA (the human eIF5A siRNA is not active in mouse)

8-Day Maximum Tolerated Dose Study (MTD)

The two-dose 8-day study was a dose range-finding study designed to determine the maximum tolerated dose of SNS01. The dose range was 2.2 mg/kg to 3.7 mg/kg and is well above the therapeutic dose range of 0.75 mg/kg to 1.5 mg/kg. At the lowest dose (2.2 mg/kg) of SNS01 no clinical signs of toxicity were observed except for one mouse that exhibited slightly ruffled fur and decreased activity that resolved within one hour. No clinical signs of toxicity were observed following the $2^{nd}$ injection of 2.2 mg/kg of SNS01. All the mice maintained their weight throughout the study. No macroscopic changes in the organs were observed. The organ weight to body weight ratios were unchanged from the control group except for a modest increase in the ratio of the liver weight:body weight ratio. However, since an increase in this ratio was not observed in any of the higher dose level groups it is unlikely to be related to the test article.

Four out of five mice tolerated 2.9 mg/kg of SNS01 with no clinical signs of toxicity. However, one mouse experienced convulsions and mild respiratory distress within 1 hour of injection and had to be humanely euthanized. No clinical signs of toxicity were observed following the $2^{nd}$ injection of SNS01 in the remaining mice. The mice maintained their weight throughout the study and no macroscopic changes in the organs or changes in the organ weight to body weight ratios were observed. There was a slight increase in the serum levels of ALT following two doses of 2.9 mg/kg SNS01.

As expected, doses of SNS01 at or above 3.3 mg/kg were not well tolerated and in both groups all mice but one had to be humanely euthanized. In all cases where mice were humanely euthanized due to morbidity the clinical signs appeared within 1 hour of injection and were consistent with other reported studies using high doses of PEI. The surviving mice of the 3.3 mg/kg and 3.7 mg/kg recovered completely within 4 hours after the injection and maintained their weight throughout the study, although they did not receive a $2^{nd}$ dose. The maximum tolerated dose of SNS01 therefore appears to be between 2.2 mg/kg and 2.9 mg/kg.

9-Week Repeated Dose Study (EX6)

The purpose of the 9-week repeated dose study was to assess the safety of chronic administration of therapeutic doses (1.5 mg/kg) of SNS-EF1/UU, a complex that was used for preclinical studies during development of SNS01. SNS-EF1/UU does not differ significantly from SNS01, the major difference being that the materials are research-grade and that eIF5A$^{K50R}$ expression is driven by the constitutive human EF1 promoter that is active in all cell types. Although SNS01 uses a B-cell-specific promoter to drive eIF5A$^{K50R}$ expression, the use of a constitutive promoter in this safety study allows for the assessment of toxicity resulting from the accumulation of the mutant eIF5A$^{K50R}$ protein in non-B-cell tissues. Another aspect of the 9-week repeated dose study was the inclusion of groups to test the safety of the individual components of SNS-EF1/UU. The DNA group (Ex6-G3) was dosed with a complex containing the eIF5A plasmid and a non-targeting control siRNA while the siRNA group (Ex6-G4) was dosed with a complex containing the human eIF5A (h5A1) siRNA and a non-expressing plasmid. Since the test article SNS-EF1/UU contains a human eIF5A siRNA that will not affect expression of the endogenous mouse eIF5A, another feature of this study was the inclusion of a group (Ex6-G6) that was dosed with PEI complexes containing a non-expressing plasmid and an siRNA that efficiently targets mouse eIF5A. This group allowed assessment of the safety of chronic administration of an active eIF5A siRNA.

All animals survived to the scheduled sacrifice date. No clinical signs of toxicity were observed in any of the groups over the course of the 9-week study and the mice in all groups continued to gain weight during the study period. Red and white blood cell counts were measured three and six weeks after the initiation of treatment and were normal for all dosing groups. Serum liver enzyme levels were measured following sacrifice and were within the normal range for all mice. No changes in the macroscopic appearance of the organs were observed in any of the groups. Histopathological analysis of the major organs was conducted by an independent pathologist (and revealed no toxicity attributable to the test article.

Chronic administration of therapeutic doses of SNS-EF1/UU is well tolerated by mice and no adverse effects were observed. In addition, chronic administration of a mouse-specific eIF5A siRNA revealed no toxic effects, indicating that the administration of PEI complexes containing a human eIF5A siRNA should be safe for humans.

Example 21

Therapeutic Efficacy Studies with Intra-Venous SNS-B29/UU and SNS01 in Multiple Myeloma Tumor-Bearing Mice SNS01 is as described above. The test article SNS-B29/UU is a preclinical version of SNS01. SNS-B29/UU differs very little from SNS01, the chief difference being that the components are of research-grade rather than GLP-grade. The purpose of the study reported here was to determine the minimum effective dose of SNS-B29/UU and to confirm that the GLP-grade materials that comprise SNS01 perform as well as the research-grade materials that were used for the preclinical studies. The repeated dose tumor study (Study ID: EX9) was a 5-week study in which the ability of increasingly smaller twice-weekly doses of SNS-B29/UU to inhibit subcutaneous tumor growth in mice was assessed in order to determine the optimal therapeutic dose of SNS01. The treated animals were also assessed for signs of toxicity by monitoring clinical signs, body weight and organ weight.

| Study ID | Animal Model | Injection Schedule | Duration of Treatment | Test Article |
|---|---|---|---|---|
| Ex9 | C.B17 (SCID) (female) mice bearing subcutaneous human multiple myeloma tumors (KAS-6/1) | Twice weekly Intra-venous<br>Twice weekly Intra-venous | 35 Days<br>25 Days | SNS-B29/UU<br>SNS01 |

| Test Article | Plasmid DNA | siRNA | Vehicle | Material Grade |
|---|---|---|---|---|
| SNS01[a] | pEXp5A[c] (eIF5A$^{K50R}$ expression driven by B29 B-cell-specific promoter) | eIF5A siRNA[d] (dTdT overhang[e]) human-specific eIF5A siRNA | In vivo-jetPEI ™ | GLP-grade materials |
| SNS-B29/UU[b] | pExp5A[c] | h5A1 (UU overhang[e]) human-specific eIF5A siRNA | In vivo-jetPEI ™ | Research-grade materials |

Figure 26:
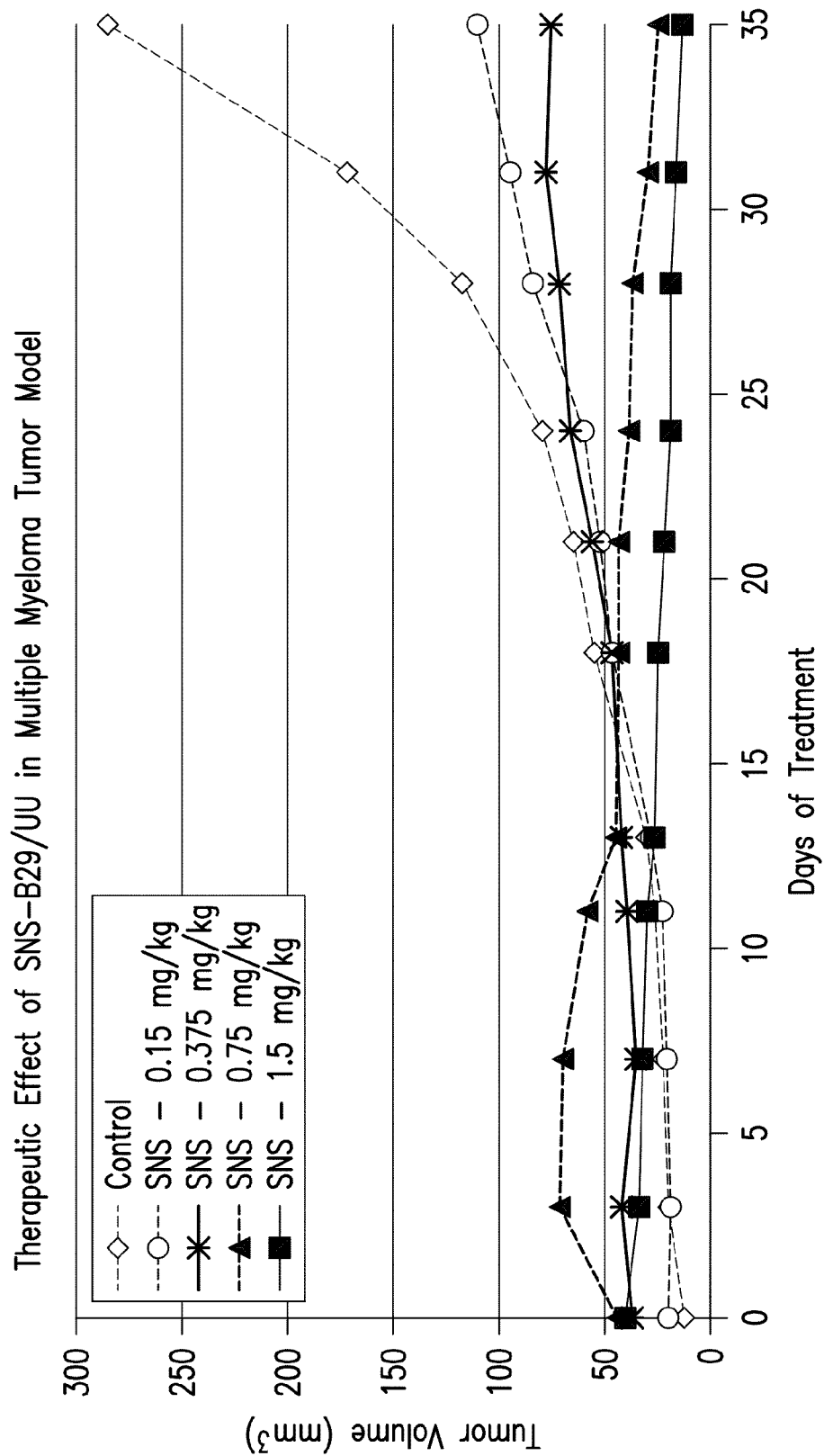
FIG. 26 provides the results of efficacy studies in multiple myeloma. See example 21.
Figure 27:
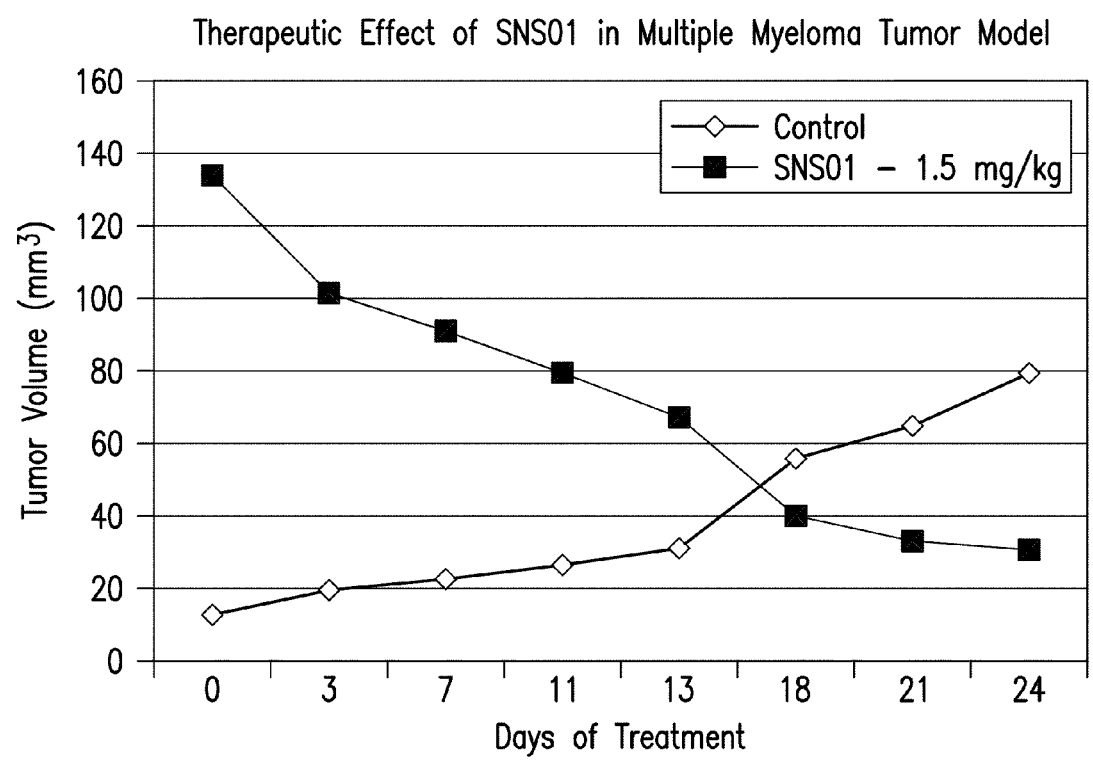
FIG. 27 provides the results of efficacy studies in multiple myeloma. See example 21.

[a] SNS01 contains GLP-grade materials and is being developed for the clinic
[b] SNS-B29/UU is a test article used in preclinical research that led to the development of SNS01
[c] the pExp5A plasmid is RNAi-resistant due to the fact that the plasmid contains only the open reading frame of eIF5A while the eIF5A siRNA (h5A1) targets the 3' UTR of eIF5A
[d] the sequence of the eIF5A siRNA and the h5A1siRNAs are identical except for the presencee of a dTdT overhang rather than a UU overhang on the 3' terminal ends of the siRNA; the dTdT overhang does not affect the target selectivity or efficacy of the siRNA but has been proposed to enhance stability The therapeutic range of SNS-B29/UU was determined in SCID mice bearing subcutaneous human multiple myeloma tumors. Doses of SNS-B29/UU between 0.15 mg/kg and 1.5 mg/kg were tested. The anti-tumoral efficacy of the test article was determined by twice-weekly tumor volume measurements and by excising and weighing tumor tissue following sacrifice. SNS-B29/UU doses of 0.75 mg/kg and 1.5 mg/kg resulted in significant tumor shrinkage indicating that the therapeutic range of SNS-B29/UU lies between 0.75 mg/kg and 1.5 mg/kg. Effective inhibition of growth of subcutaneous tumors was also observed at 0.38 mg/kg SNS-B29/UU although no tumor shrinkage was observed. Some inhibition of tumor growth was even observed at doses as low as 0.15 mg/kg SNS-B29/UU indicating a broad therapeutic range. See FIGS. 26 and 27.

The efficacy of SNS01 made using GLP-grade components was compared to SNS-B29/UU and was found have a comparable efficacy in the inhibition of tumor growth. Treatment of tumor-bearing SCID mice with SNS01 and SNS-B29/UU was well tolerated and the mice continued to gain weight throughout the study.

Test Article and Vehicle

| Test Article | Manufacturer of Plasmid DNA component | Manufacturer of siRNA component | Manufacturer of PEI component | Formation of Test Article |
|---|---|---|---|---|
| SNS01 | VGXI Lot # pExp5A.08L007 | Avecia | Polyplus Transfection Inc GLP-Grade | Components were combined with 10% glucose to form |

| Test Article | Manufacturer of Plasmid DNA component | Manufacturer of siRNA component | Manufacturer of PEI component | Formation of Test Article |
|---|---|---|---|---|
| SNS-B29/UU | Qiagen EndoFree Plasmid Mega Kit <0.1 EU/µg DNA | ThermoScientific Dharmacon RNAi Technologies | Polyplus Transfection Inc. Research-Grade | nano-complexes; complexes were injected within 2-4 hours Components were combined with 10% glucose to form nano-complexes; complexes were injected within 2-4 hours |
| Storage Conditions (Stability) | −20° C. (≧1 year) | −20° (≧1 year) | 4° (≧1 year) | Room Temperature (≧6 hours) |

Test Systems and Study Design

The female C.B.17/IcrHsd-Prkdc (SCID) mice were obtained from Harlan (Indianapolis, Ind., USA). Subcutaneous tumors were established by injecting 10×10$^6$ viable KAS-6/1 (human multiple myeloma) cells into the right flank of 5 to 6 week-old mice. Treatment with SNS-B29/UU began when the tumors reached an approximate size of 20 to 40 mm$^3$ (approximately 4 weeks after tumor cell injection). Treatment with SNS01 began when the tumors reached an approximate size of 130 mm$^3$ (approximately 6 weeks after tumor cell injection). Mice received the test article twice-weekly via tail vein intra-venous injection.

| | | STUDY ID: EX9 | | | | |
|---|---|---|---|---|---|---|
| Group | No. Animals (female) | Test Article | N/P ratio | Dose level (mg/kg) | Injection Volume | Total # injections |
| Ex9-G1 | 3 | Control$^a$ | 6 | 1.5 mg/kg | 0.1 mL | 11 |
| Ex9-G2 | 4 | SNS-B29/UU | 6 | 1.5 mg/kg | 0.1 mL | 11 |
| Ex9-G3 | 4 | SNS-B29/UU | 6 | 0.75 mg/kg | 0.05 mL | 11 |
| Ex9-G4 | 4 | SNS-B29/UU | 6 | 0.38 mg/kg | 0.025 mL | 11 |
| Ex9-G5 | 3 | SNS-B29/UU | 6 | 0.15 mg/kg | 0.01 mL | 11 |
| Ex9-G9 | 3 | SNS01 | 6 | 1.5 mg/kg | 0.1 mL | 7 |

$^a$PEI complex containing a non-expressing plasmid (same vector background as pExp5A) and a non-targeting siRNA Repeated Dose Tumor Study The repeated dose tumor study was designed to determine the minimum effective therapeutic dose of SNS-B29/UU and to confirm that the GLP-grade SNS01 test article retained the tumor inhibition activity demonstrated by the research-grade test article SNS-B29/UU. A secondary objective was to assess any toxic effects of the treatment by monitoring the treated mice for clinical signs, body weight, and organ weight. Test article therapeutic anti-tumoral activity was monitored by twice-weekly tumor volume measurements using digital calipers. Upon sacrifice the tumors were excised and weighed.

All the mice survived to the scheduled sacrifice date. Control mice that were treated with PEI nanocomplexes containing a non-expressing plasmid and a non-targeting siRNA had an average tumor volume of 284 mm$^3$ at the time of sacrifice while mice treated with 1.5 mg/kg SNS-B29/UU had an average tumor volume of only 13 mm$^3$, a 95% (*p=0.026) reduction in tumor growth. However, when it was attempted to excise the tumors from mice that had been treated with 1.5 mg/kg SNS-B29/UU, no evidence of a tumor was found in any of the mice. Decreasing the dose of SNS-B29/UU by half to 0.75 mg/kg still resulted in a 91% (*p=0.03) and 87% (*p=0.04) decrease in tumor volume and weight, respectively, and in one mouse the tumor had completely disappeared. Therefore, the optimum therapeutic dose for twice-weekly injections of SNS-B29/UU appears to be between 0.75 mg/kg and 1.5 mg/kg. Twice-weekly doses of SNS-B29/UU doses as low as 0.15 mg/kg still resulted in a 60% reduction in the final tumor volume indicating that SNS-B29/UU has potent anti-tumoral activity over a wide dose range.

In addition to inhibiting tumor growth, treatment with SNS-B29/UU and SNS01 at 0.75 mg/kg and 1.5 mg/kg resulted in significant reduction in tumor volume indicating that this treatment is capable of inducing tumor regression, likely through the induction of apoptosis in the tumor. The percent change in tumor volume in tumor-bearing mice treated with SNS-B29/UU, at dose levels of 0.75 mg/kg and 1.5 mg/kg, was −244% and −245%, respectively. The tumors of control mice increased in size by more than 2000% during the same time period. Twice-weekly injections of SNS01 also significantly shrunk multiple myeloma tumors. The percent change in tumor volume for mice treated with 1.5 mg/kg SNS01 was −349%, indicating that SNS01 is just as effective as SNS-B29/UU. The use of GLP-grade materials may in fact have increased the biological activity since treatment with SNS01 achieved a 349% decrease in tumor volume following only 25 days of treatment while SNS-B29/UU achieved a 245% reduction in tumor volume following 35 days of treatment. In addition, the tumors treated with SNS01 were quite large (~130 mm$^3$) indicating that treatment with SNS01 is effective against well-established tumors.

The treatment was well tolerated by all mice and no clinical signs of toxicity were observed. The mice in all groups continued to gain weight throughout the study. No changes in the macroscopic appearance of the organs was observed at necropsy and no significant changes in the organ weight to body weight ratios occurred.

Therefore SNS01 (and its preclinical version SNS-B29/UU) is well tolerated by SCID mice and is extremely effective in treating subcutaneous human multiple myeloma tumors when delivered by intra-venous injection twice per week. All doses of SNS-B29/UU that were tested were effective at inhibiting tumor growth but the highest dose of 1.5 mg/kg successfully eliminated tumors in all mice receiving treatment.

Example 22

Biodistribution of Plasmid DNA and siRNA Polyethylenimine (JetPEI) Complexes

Green fluorescent protein ("GFP") GFP-expression constructs were used to determine localization of plasmid DNA delivered by PEI complexes. Two promoters were used to drive GFP expression: EF1: ubiquitous promoter (EF1::GFP) or B29: B-cell specific promoter (B29::GFP). PEI complexes containing 20 micrograms of GFP plasmid DNA and 10 micrograms of a fluorescently-labelled (DY547) h5A1 siRNA were prepared at an N/P ratio of 6. BalB/C mice were injected intra-venously with either 5% glucose or PEI complexes on two consecutive days. Seventy-two hours following the firsts injection the mice were euthanized and their organs were harvested and analyzed for GFP expression and DY547-siRNA by confocal microscopy.
Bone Marrow In most cases there was evidence of DY547-siRNA but no GFP expression. Timing of organ harvest may not coincide with peak expression of GFP; and there may be quenching of GFP signal or GFP may not be expressed. However, GFP and DY547 that colocalized to the same bone marrow cells in some instances was observed. Therefore, this provides evidence that PEI nanoparticles can transfect bone marrow cells in a live animal when given by intra-venous injection
Lung: In most cases there was evidence of DY547-siRNA but no GFP expression. Timing of organ harvest may not coincide with peak expression of GFP or there may be quenching of GFP signal or GFP may not be expressed.
Spleen: Evidence of GFP expression (when driven by EF1 promoter) colocalizing in cells also positive for the presence of DY547-siRNA was seen. Expression of GFP was much lower in spleen cells when driven by the B29 promoter. This shows that PEI nanoparticles appear to transfect cells of the spleen.
Kidney: No GFP or DY547 was observed indicating nanoparticles may not enter kidney.
Liver: In most cases there was evidence of DY547-siRNA but no GFP expression. This provides evidence that PEI nanoparticles are transfecting cells of the liver.
Heart: Colocalization of EF1::GFP and DY547-siRNA in tissue of heart was seen, thus indicating that PEI nanoparticles may be transfecting this organ. No GFP was observed with B29 promoter.

Example 23

Effect of DNA:siRNA Ratio on HA-eIF5A$^{K50R}$ Expression

KAS cells were transfected with nanoparticles containing B29-HA-eIF5A$^{K50R}$ (plasmid driven by B-cell-specific promoter) and h5A1 siRNA. JET PEI™ nanoparticles containing different ratios of pExp5A and h5A1 siRNA were made and incubated for 4 hours at room temperature prior to addition to KAS cells. Four hours after transfection, the nanoparticle-containing media was replaced with fresh media. Twenty-four hours later the cell lysate was harvested and used for western blot analysis with an antibody against HA. The ratio of DNA:siRNA was varied from the standard ratio of 2:1. The accumulation of HA-eIF5A$^{K50R}$ peaked at ratios of 1:0, 3:1, and 2:1. See FIG. 30.

Example 24

Effect of DNA:siRNA Ratio on Apoptosis Induced by Nanoparticle Transfection

Figure 31:
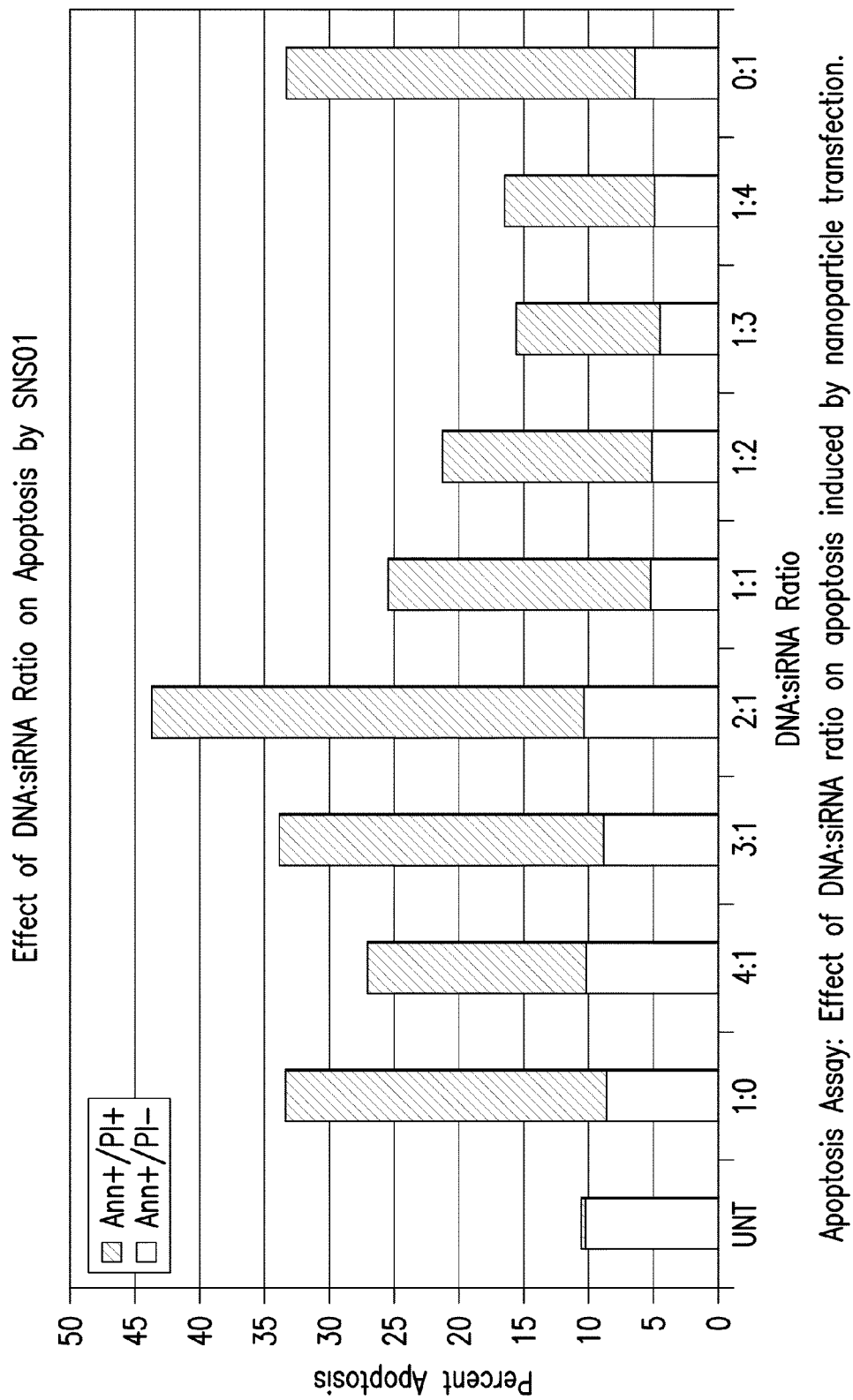
FIG. 31 shows the effect of DNA:siRNA ratio on apoptosis induced by nanoparticle transfection. See example 24.

Nanoparticles containing different ratios of pExp5A and h5A1 siRNA were made and incubated for 4 hours at room temperature prior to addition to KAS cells. Four hours after transfection, the nanoparticle-containing media was replaced with fresh media. Forty-eight hours later the cells were harvested, labelled with Annexin V/PI and analyzed by FACS. The induction of apoptosis was highest in cells transfected with nanoparticles with the standard DNA:siRNA ratio of 2:1. See FIG. 31.

Example 25

Figure 32:
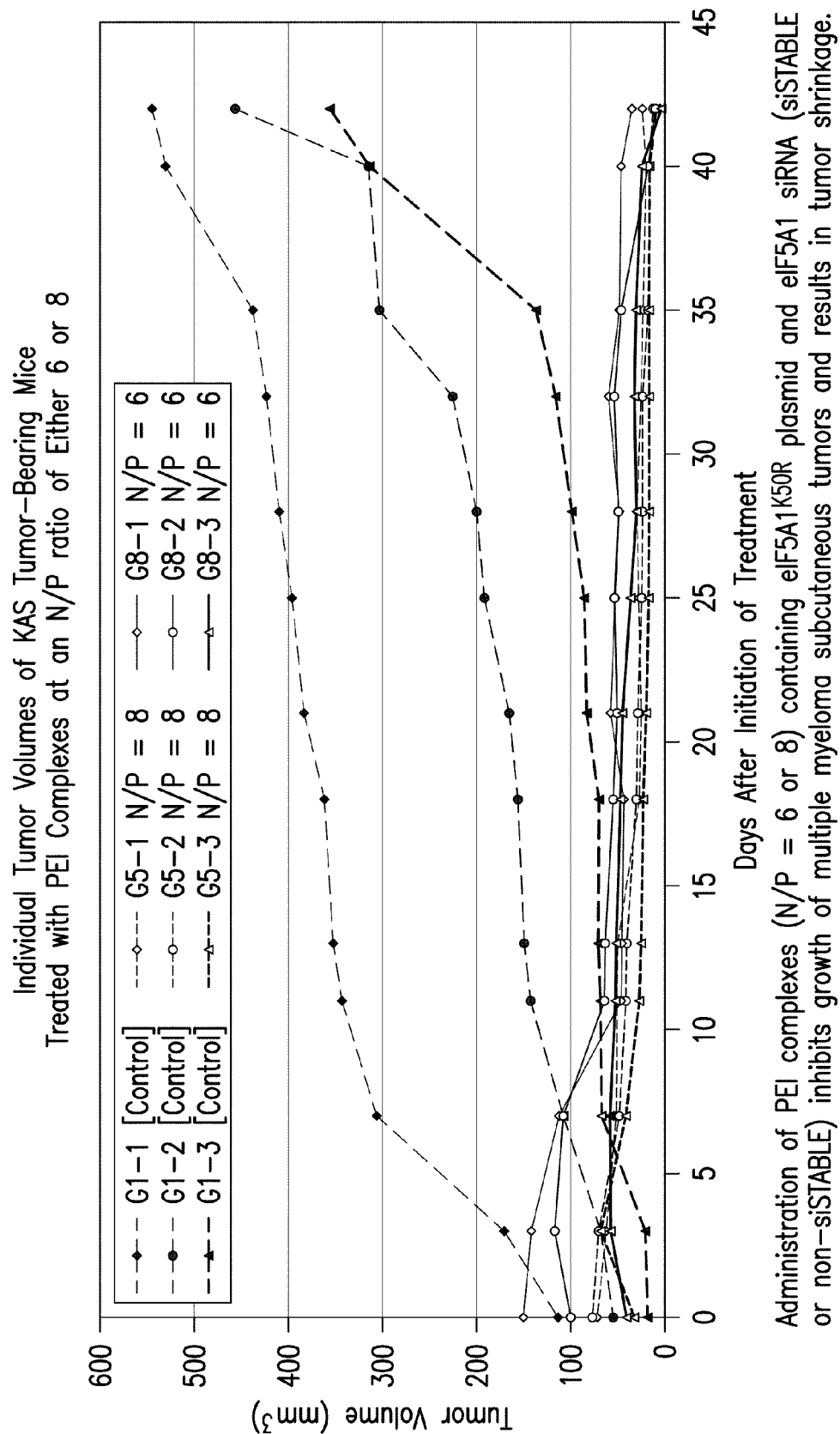
FIG. 32 shows administration of PEI complexes (N/P=6 or 8) containing eIF5A1K50R plasmid and eIF5A1 siRNA (siS-TABLE or non-siSTABLE) inhibits growth of multiple myeloma subcutaneous tumors and results in tumor shrinkage. See example 25.

Administration of PEI Complexes (N/P=6 or 8) Containing eIF5A1K50R Plasmid and eIF5A1 siRNA (siSTABLE or Non-siSTABLE) Inhibits Growth of Multiple Myeloma Subcutaneous Tumors and Results in Tumor Shrinkage SCID mice were injected subcutaneously with KAS cells. Treatment was initiated when palpable tumors were observed. Mice were injected intra-venously 2 times per week with either: (G1) PEI complexes containing 20 mg of pCpG-mcs (empty vector) and 10 mg of control siRNA at N/P=8 (medium dose); (G5) PEI complexes containing 20 mg of the RNAi-resistant plasmid pCpG-eIF5A1k50R and 10 mg of siSTABLE h5A1 siRNA at N/P=8 (lmedium dose, siSTABLE); (G8) PEI complexes containing 20 mg of the RNAi-resistant plasmid pCpG-eIF5A1k50R and 10 mg of h5A1 siRNA at N/P=6 (medium dose, N/P=6). The data shown is the individual tumor volume for the mice in each group. The final injection was given at day 40 after initiation of treatment. See FIG. 32.

Example 26

JET PEI™ Nanoparticles are Being Effectively Taken Up by Tumor Tissue and that Nanoparticles are Delivering Plasmid and siRNA to the Same Cell Tumor section 48 hours after injection with nanoparticles containing pExp-GFP (GFP under control of B-cell-specific promoter) and DY547-siRNA (fluorescently-labelled siRNA). Co-localized expression of GFP and DY547 is observed in tumor section following confocal microscopy indicating that the nanoparticles are being effectively taken up by tumor tissue and that nanoparticles are delivering plasmid and siRNA to the same cell. See FIG. 33.

Example 27

Adenovirus Constructs Created for Truncation Study

Adenovirus (Serotype 5, E3-Deleted)
1) Ad-eIF5A1Δ(2-6) [Δ(2-6)]—this is a human eIF5A1 lacking amino acids 2 to 6.
2) Ad-eIF5A1K50RΔ(2-6) [Δ(2-6)/K50R] this is human eIF5A1 lacking amino acids 2 to 6. Additionally, the "K50R" means that the Lysine (K) at position 50 has been mutated to arginine (R) and is hence believed unable to by hypusinated by DHS.
3) Ad-eIF5A1D6E [D6E]—this is human eIF5A1 in which the predicted cleavage site has been mutated (D6 to E).
4) Ad-eIF5A1D6E/K50R [D6E/K50R]—this is human eIF5A1K50R in which predicted cleavage site has been mutated (D6 to E). Additionally, the "K50R" means that the Lysine (K) at position 50 has been mutated to arginine (R) and is hence believed unable to by hypusinated by DHS.

Example 28

Caspase Mediated Cleavage of eIF5A

To identify the site of cleavage, protein lysate isolated from KAS cells treated with Actinomycin D was separated by 2-D gel electrophoresis (FIG. 37) and the spot corresponding to the smaller molecular weight eIF5A cleavage product was cut out of the gel and sequenced by mass spectroscopy (FIG. 38B). Although a full-length sequence of the cleavage product was not obtained, it was determined that the cleavage occurred following the $6^{th}$ amino acid from the N-terminal end of the protein (FIG. 38A). The sequence immediately preceding the suspected cleavage site is 'DDLD' (SEQ ID NO: 47), a sequence that has been identified as a caspase cleavage site (Chay et al., 2002).

To determine whether production of the cleavage fragment is caspase-dependent, the ability of caspase inhibitors to block the production of the cleavage fragment produced during Actinomycin D-induced apoptosis in human myeloma cells was tested (FIG. 41). A general caspase inhibitor and specific inhibitors of caspase 3, 8 and 9 all strongly prevent the formation of the cleavage form of eIF5A that accumulates during ActD-induced apoptosis in KAS cells. A caspase 1 inhibitor also reduced, but did not completely block, the formation of the cleavage product. Incubation with the caspase inhibitors not only prevented the accumulation of the cleavage product, but also inhibited loss of the hypusinated form of eIF5A (FIG. 41), indicating that loss of hypusinated eIF5A during Actinomycin D-induced apoptosis is a result of cleavage.

Caspase cleavage of proteins during apoptosis (reviewed by Fisher et al., 2003) can have a myriad of purposes: 1) to inactivate pro-survival or anti-apoptotic proteins—for example: the eukaryotic translation initiation factor 4G1, which binds to the 5' cap structure of mRNAs and facilitates binding of capped mRNA to 40S ribosomal subunits, is inactivated by caspase cleavage, thereby inhibiting translation; 2) to create a dominant negative form of the protein (for example, NF-kappa B p65 is cleaved by caspases during apoptosis to create a dominant-negative fragment that binds DNA but has no trans-activating activity and therefore acts as a dominant-negative inhibitor of NF-kB); 3) gain-of-function cleavage resulting in the activation of a pro-apoptotic protein by removal of an inhibitory or regulatory domain thereby resulting in formation of a fragment with a new activity or increased activity (for example, BRCA-1, a breast cancer suppressor protein that mediates cell cycle arrest and apoptosis, is activated by caspase cleavage which releases a pro-apoptotic cleavage fragment. DAPS, a member of the eIF4G family is activated following caspase cleavage; the cleavage product stimulates translation of apoptosis-related proteins); 4) conversion of an anti-apoptotic protein to a pro-apoptotic protein (for example, apoptotic inhibitors, such as Bcl-$x_L$ and c-IAP1, can be turned into pro-apoptotic proteins through cleavage by caspase); and 5) cellular redistribution (for example, upon cleavage by caspase 8, the pro-apopototic p15 fragment of Bid undergoes myristoylation at a glycine residue exposed by cleavage which subsequently enables Bid to translocate to the mitochondria where it enhances cytochrome c release).

To determine whether caspase-mediated cleavage of eIF5A during Actinomycin D-induced apoptosis is a general phenomena or specific to myeloma cells, HeLa cells treated with Actinomycin D were examined for the presence of cleaved eIF5A (FIG. 42). No accumulation of the eIF5A cleavage fragment was observed in Actinomycin D-treated HeLa cells. In an effort to determine whether post-translation modification (such as phosphorylation or acetylation) of eIF5A may be a pre-requisite for cleavage by caspases, the effect of a deacetylase inhibitor, nicotinamide, on the formation of the cleavage fragment was examined. Acetylation of eIF5A has been observed by mass spectroscopy analysis of eIF5A by our lab and others (Kim et al., 2006). Furthermore, yeast eIF5A has been identified as a substrate of the Sir2-related deacetylase Hst2 (Shirai et al., 2008) and the authors observed that acetylation of eIF5A was only observed in yeast lacking Hst2 or in yeast in which eIF5A was over-expressed, indicating that eIF5A is generally present in the unacetylated form. Incubation of Actinomycin D-treated HeLa cells with the Sir2 deacetylase inhibitor nicotinamide, resulted in the accumulation of the eIF5A cleavage product indicating that acetylation of eIF5A is required for caspase-mediated cleavage to occur. These data suggest that eIF5A may normally be protected from caspase activity until an apoptotic signal triggers acetylation of eIF5A and allows caspase-mediated cleavage.

REFERENCES

Chay K O, Park S S, Mushinski J F (2002). Linkage of caspase-mediated degradation of paxillin to apoptosis in Ba/F3 murine pro-B lymphocytes. J Biol. Chem. 277, 14521-14529.

Fischer U, Janicke R U, Schulze-Osthoff K (2003). Many cuts to ruin: a comprehensive update of caspase substrates. Cell Death and Differentiation 10, 76-100.

Kim, S. C., Sprung, R., Chen, Y., Xu, Y., Ball, H., Pei, J., Cheng, T., Kho, Y., Xiao, H., Xiao, L., Grishin, N. V., White, M., Yang, X. J., and Zhao, Y. (2006) Substrate and Functional Diversity of Lysine Acetylation Revealed by a Proteomics Survey. Mol Cell 23, 607-618.

Shirai et al. (2008). Global analysis of gel mobility of proteins and its use in target identification J. Biol. Chem. 283, 10745-10752.

The invention claimed is:

1. An isolated polynucleotide encoding a truncated eIF5A1 protein wherein the truncated protein consists of the amino acid sequence set forth in SEQ ID NO: 37.

2. The isolated polynucleotide of claim 1, encoding a truncated eIF5A1 protein wherein the polynucleotide consists of the sequence set forth in SEQ ID NO: 38.

3. The isolated polynucleotide of claim 1, wherein the polynucleotide is comprised within a plasmid or an expression vector.

4. The isolated polynucleotide of claim 3, wherein the vector is an adenovirus vector.

5. The isolated polynucleotide of claim 3, wherein the vector is an adenovirus expression vector or is pHM6.

6. The isolated polynucleotide of claim 5, wherein the expression vector comprises a tissue specific promoter.

7. The isolated polynucleotide of claim 6 wherein the tissue specific promoter is a B cell specific promoter.

8. The isolated polynucleotide of claim 7 wherein the B cell specific promoter is B29.

9. The isolated polynucleotide of claim 5 wherein the expression vector comprises a pCpG plasmid.

10. The isolated polynucleotide of claim 5 wherein the expression vector is complexed to polyethylenimine.

11. The isolated polynucleotide of claim 5 where in the expression vector has reduced CpG dinucleotides.

12. A method for inducing apoptosis in a cancer cell or in a tumor in a subject, the method comprising administering the plasmid or expression vector of claim 3 an eIF5A1 polynucleotide that encodes a truncated eIF5A1 protein, wherein the truncated eIFA1 protein consists of the amino acid sequence set forth in SEQ ID NO:37.

13. The method of claim 12 wherein the expression vector is an adenovirus expression vector or is pHM6.

14. The method of claim 13 wherein the expression vector comprises a tissue specific promoter.

15. The method of claim 14 wherein the tissue specific promoter is a B cell specific promoter.

16. The method of claim 15 wherein the B cell specific promoter is B29.

17. The method of claim 13 wherein the expression vector comprises a pCpG plasmid.

18. The method of claim 13 wherein the expression vector is complexed to polyethylenimine.

19. The method of claim 13 where in the expression vector has reduced CpG dinucleotides.

20. The method of claim 12 wherein the medicament plasmid or expression vector is administered intratumorally, intravenously or subcutaneously.

* * * * *

SEQUENCE LISTING

<160> NUMBER OF SEQ ID NOS: 51

<210> SEQ ID NO 1
<211> LENGTH: 21
<212> TYPE: DNA
<213> ORGANISM: Homo sapiens

<400> SEQUENCE: 1
aagctggact cctcctacac a                                              21

<210> SEQ ID NO 2
<211> LENGTH: 21
<212> TYPE: DNA
<213> ORGANISM: Homo sapiens

<400> SEQUENCE: 2
aaaggaatga cttccagctg a                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
acacauccuc cucaggucgt t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
cgaccugagg aggaugugut t                                              21

<210> SEQ ID NO 5
<211> LENGTH: 21
<212> TYPE: RNA
<213> ORGANISM: Homo sapiens

<400> SEQUENCE: 5
gcuggacucc uccuacacau u                                              21

<210> SEQ ID NO 6
<211> LENGTH: 154
<212> TYPE: PRT
<213> ORGANISM: Homo sapiens

<400> SEQUENCE: 6

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Arg His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cagcaaggga gcacctatg                                                  19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gttgcagtga gcggagatg                                                  19

<210> SEQ ID NO 9
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
accaccctgg gccaggctgg gccaagccag gcggcccctg tgttttcccc agtctctggg     60
ctgctggagg gaaccaggtt gttttggcat cagcctctac tgagccggag cccttccttt   120
cctgctgctt tgcatagtgg cactaattcc gtcctcctac ctccaccagg gacctaggca   180
gccgggtaga tggtgggagg aggcttcact tctcccccaa gcagggtctc cacctgcttg   240
aggctgccct gggttggggg aggccttggc tttacctaaa gactttttaa caccctct     297

<210> SEQ ID NO 10
<211> LENGTH: 800
<212> TYPE: DNA
<213> ORGANISM: Homo sapiens

<400> SEQUENCE: 10
gggaacagct gccagctggg agaccaagtg caatcaacct gcacgtgcaa agcctccctc     60

```
ccaagccagg ctgtgctcca cttcctgttg accctggagg gaatccttcg aggcccctct    120
gctattcctg ctctgaattc cagcaaggga gcacctatgc tgtgggagct gccagtttaa    180
ctggggaatc aagaccagca caggggaact agtgagaaca gtgccaattt tcaccagatt    240
ccctctggaa ttccaggtgg ggcaggtggg taaggccccc acgcctgcag tttcaggtaa    300
atctctccac caccctgggc caggctgggc caagccaggc ggcccctgtg ttttccccag    360
tctctgggct gctggaggga accaggttgt tttggcatca gcctctactg agccggagcc    420
cttcctttcc tgctgctttg catagtggca ctaattccgt cctcctacct ccaccaggga    480
cctaggcagc cgggtagatg gtgggaggag gcttcacttc tcccccaagc agggtctcca    540
cctgcttgag gctgccctgg gttggggag gccttggctt tacctaaaga cttttttaaca    600 cctctgaaca acacagtttc cctgagactt tgaagctctt gttttatta tttatttatt    660 tatttattta cttatttatt tatttgcaga cagagtctca ctctgttgcc cagactggag    720
tgcagtggca ccatctccgc tcactgcaac ctccgtctcc tgagttcaag caattctcct    780
gcctcagcct ccaaagtacc                                                 800

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccaactagtg cgaccgccaa accttagc                                         28

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caaaagcttg acaacgtccg aggctccttg g                                     31

<210> SEQ ID NO 13
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gcgaccgcca aaccttagcg gcccagctga caaaagcctg ccctccccca gggtccccgg     60
agagctggtg cctcccctgg gtcccaattt gcatggcagg aaggggcctg gtgaggaaga    120
ggcggggagg ggacaggctg cagccggtgc agttacacgt tttcctccaa ggagcctcgg    180
acgttgtc                                                              188

<210> SEQ ID NO 14
<211> LENGTH: 1237
<212> TYPE: DNA
<213> ORGANISM: Homo sapiens

<400> SEQUENCE: 14
```

```
cctgcagggc ccactagtaa acggagggtt gtgaggagag tgagaggtgg acagagggca    60
ccgacgattt agcatctctt cctctcctgg gggtcgagga tgagagacaa aaaagaagct   120
gccaggaaac ataaaattca gagggctcag ctgcagggct gaggtctgca agcatgctgt   180
gtacacttgt gcatgttgtg ccctgcacaa gggcatctct gaaggggctg cactggaccc   240
aggggcaggg gcgcaaaggt gagtttatat cagttcctga gcactgtggc tccatccagc   300
actctgagga caggcaggat acagctggag gacctgaggg ctcccccaca ccagctcctg   360
ttccctgccc aagacccct ggacctgcag acaacaattc aacgcactca gagtcccaca   420
gttaagaact ccctgaagaa gccccagtg gctgcgtggt ggattttcgc aaagctgtct   480
ccacctacat ccaccctgtt tggcagcccc tacatactct ttcacagcat gaggaaggga   540
ggcctctcac caagacctgg actgaatctt ctcccagtgg ctgccacacc tgacctgctc   600
ttgctccaga acctctgtgg ctcccatcct ccacagggtc aacttccaac atggctgcct   660
gcactccagc caagaggctc tgctctgggc ccctccagat gcctgacctg ggtctgtggc   720
tgccctgtcc ttcttcagtg ctcctcttcc cgctgggtga ggaatagttc aggacagagg   780
agctaagttc aggttcattc ataggacagg tgcctatttc gctcacggcc caggaataga   840
gacttgccgg gctcggccct tcggggagtt ggcagacggc agaggggagg ctggctggcc   900
caggggatga ccaccggtgg ggtaagcaca gacagagggg agcacaggct tcccccagaa   960
gactgagagg cccccagag gcatccacag aggacccag ctgtgctgcc caagctgggc  1020
gaccgccaaa ccttagcggc ccagctgaca aaagcctgcc ctcccccagg gtccccggag  1080
agctggtgcc tccctgggt cccaatttgc atggcaggaa ggggcctggt gaggaagagg  1140
cggggagggg acaggctgca gccggtgcag ttacacgtttt cctccaagg agcctcggac  1200 gttgtcacgg gtttggggtc ggggacagag cggtgac                          1237
```

<210> SEQ ID NO 15
<211> LENGTH: 61
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 15

```
cgccatggac atgtacccctt acgacgtccc agactacgct gcagatgatt tggacttcga    60
g                                                                    61
```

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 16

```
cgcgctagcc agttattttg ccatcgcc                                       28
```

<210> SEQ ID NO 17
<211> LENGTH: 497
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 17

```
acatgtaccc ttacgacgtc ccagactacg ctgcagatga tttggacttc gagacaggag      60
atgcaggggc ctcagccacc ttcccaatgc agtgctcagc attacgtaag aatggttttg     120
tggtgctcaa gggccggcca tgtaagatcg tcgagatgtc tacttcgaag actggcaggc     180
atggccatgc caaggtccat ctggttggca ttgatatttt tactgggaag aaatatgaag     240
atatctgccc gtcgactcat aacatggatg tccccaacat caaaaggaat gatttccagc     300
tgattggcat ccaggatggg tacctatccc tgctccagga cagtggggag gtacgagagg     360
accttcgtct gcctgaggga gaccttggca aggagattga gcagaagtat gactgtggag     420
aagagatcct gatcacagtg ctgtccgcca tgacagagga ggcagctgtt gcaatcaagg     480
cgatggcaaa ataactg                                                   497
```

<210> SEQ ID NO 18
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Met Tyr Pro Tyr Asp Val Pro Asp Tyr Ala Ala Asp Asp Leu
1               5                   10                  15

Asp Phe Glu Thr Gly Asp Ala Gly Ala Ser Ala Thr Phe Pro Met Gln
            20                  25                  30

Cys Ser Ala Leu Arg Lys Asn Gly Phe Val Val Leu Lys Gly Arg Pro
        35                  40                  45

Cys Lys Ile Val Glu Met Ser Thr Ser Lys Thr Gly Arg His Gly His
    50                  55                  60

Ala Lys Val His Leu Val Gly Ile Asp Ile Phe Thr Gly Lys Lys Tyr
65                  70                  75                  80

Glu Asp Ile Cys Pro Ser Thr His Asn Met Asp Val Pro Asn Ile Lys
                85                  90                  95

Arg Asn Asp Phe Gln Leu Ile Gly Ile Gln Asp Gly Tyr Leu Ser Leu
            100                 105                 110

Leu Gln Asp Ser Gly Glu Val Arg Glu Asp Leu Arg Leu Pro Glu Gly
        115                 120                 125

Asp Leu Gly Lys Glu Ile Glu Gln Lys Tyr Asp Cys Gly Glu Glu Ile
    130                 135                 140

Leu Ile Thr Val Leu Ser Ala Met Thr Glu Glu Ala Ala Val Ala Ile
145                 150                 155                 160

Lys Ala Met Ala Lys
                165

<210> SEQ ID NO 19
<211> LENGTH: 154
<212> TYPE: PRT
<213> ORGANISM: Homo sapiens

<400> SEQUENCE: 19

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

```
Gly Lys His Gly His Ala Lys Val His Leu Val Gly Ile Asp Ile Phe
 50                  55                  60

Thr Gly Lys Lys Tyr Glu Asp Ile Cys Pro Ser Thr His Asn Met Asp
 65                  70                  75                  80

Val Pro Asn Ile Lys Arg Asn Asp Phe Gln Leu Ile Gly Ile Gln Asp
                 85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aattctcgag tcatcgataa gcggccgcag acgcgt                        36

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aattacgcgt ctgcggccgc ttatcgatga ctcgag                        36

<210> SEQ ID NO 22
<211> LENGTH: 1030
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ggcatgtgaa ctggctgtct tggttttcat ctgtacttca tctgctacct ctgtgacctg    60
aaacatattt ataattccat taagctgtgc atatgataga tttatcatat gtattttcct   120
taaaggattt ttgtaagaac taattgaatt gatacctgta aagtctttat cacactaccc   180
aataaataat aaatctcttt gttcagctct ctgtttctat aaatatgtac aagttttatt   240
gtttttagtg gtagtgattt tattctcttt ctatatatat acacacacat gtgtgcattc   300
ataaatatat acaattttta tgaataaaaa attattagca atcaatattg aaaaccactg   360
attttgtttt atgtgagcaa acagcagatt aaaaggaatt ctcgagtcat cgataagcgg   420
ccgcagacgc gtaattcagt caatatgttc accccaaaaa agctgtttgt taacttgcca   480
acctcattct aaaatgtata tagaagccca aaagacaata acaaaaatat tcttgtagaa   540
caaaatggga agaatgttc cactaaatat caagatttag agcaaagcat gagatgtgtg   600
gggatagaca gtgaggctga taaaatagag tagagctcag aaacagaccc attgatatat   660
```

```
gtaagtgacc tatgaaaaaa atatggcatt ttacaatggg aaaatgatga tcttttctt      720 ttttagaaaa acagggaaat atatttatat gtaaaaaata aagggaacc catatgtcat      780 accatacaca caaaaaaaat tccagtgaat tataagtcta aatggagaag caaaacttt      840 aaatctttta gaaataata tagaagcatg ccatcaagac ttcagtgtag agaaaaattt      900
cttatgactc aaagtcctaa ccacaaagaa aagattgtta attagattgc atgaatatta     960
agacttattt ttaaaattaa aaaccatta gaaaagtca ggccatagaa tgacagaaaa      1020
tatttgcaac                                                            1030
```

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
gaagcggccg caccaccctg ggccaggctg g                                     31
```

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
ccacgcgtag aggtgttaaa aagtctttag gtaaag                                36
```

<210> SEQ ID NO 25
<211> LENGTH: 2282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
ttaattaaaa ttatctctaa ggcatgtgaa ctggctgtct tggttttcat ctgtacttca      60
tctgctacct ctgtgacctg aaacatattt ataattccat taagctgtgc atatgataga     120
tttatcatat gtattttcct taaaggattt ttgtaagaac taattgaatt gatacctgta     180
aagtctttat cacactaccc aataaataat aaatctcttt gttcagctct ctgtttctat     240
aaatatgtac aagttttatt gttttagtg gtagtgattt tattctcttt ctatatatat      300
acacacacat gtgtgcattc ataaatatat acaattttta tgaataaaaa attattagca     360
atcaatattg aaaccactg attttgttt atgtgagcaa acagcagatt aaaaggaatt       420
ctcgagtcat cgataagcgg ccgcaccacc ctgggccagg ctgggccaag ccaggcggcc     480
cctgtgtttt ccccagtctc tgggctgctg gagggaacca ggttgtttg gcatcagcct     540 ctactgagcc ggagcccttc ctttcctgct gctttgcata gtggcactaa ttccgtcctc    600
ctacctccac cagggaccta ggcagccggg tagatggtgg gaggaggctt cacttctccc    660
ccaagcaggg tctccacctg cttgaggctg ccctgggttg gggaggcct tggctttacc     720 taaagacttt ttaacacctc tacgcgtaat tcagtcaata tgttcacccc aaaaaagctg    780
tttgttaact tgccaacctc attctaaaat gtatatagaa gcccaaaaga caataacaaa    840
aatattcttg tagaacaaaa tgggaaagaa tgttccacta aatatcaaga tttagagcaa    900
```

-continued

```
agcatgagat gtgtggggat agacagtgag gctgataaaa tagagtagag ctcagaaaca    960
gacccattga tatatgtaag tgacctatga aaaaaatatg gcattttaca atgggaaaat   1020
gatgatcttt ttcttttta gaaaacagg gaaatatatt tatatgtaaa aaataaaagg    1080
gaacccatat gtcataccat acacacaaaa aaattccagt gaattataag tctaaatgga   1140
gaaggcaaaa ctttaaatct tttagaaaat aatatagaag catgccatca agacttcagt   1200
gtagagaaaa atttcttatg actcaaagtc ctaaccacaa agaaagatt gttaattaga    1260 ttgcatgaat attaagactt attttaaaa ttaaaaaacc attaagaaaa gtcaggccat    1320
agaatgacag aaaatatttg caacacccca gtaaagagaa ttgtaatatg cagattataa   1380
aaagaagtct tacaaatcag taaaaataa actagacaa aaatttgaac agatgaaaga    1440
gaaactctaa ataatcatta cacatgagaa actcaatctc agaaatcaga gaactatcat   1500
tgcatataca ctaaattaga gaaatattaa aaggctaagt aacatctgtg gcttaattaa   1560
aacaggtagt tgacaattaa acattggcat agtatatctg catagtataa tacaactcac   1620
tataggaggg ccatcatggc caagttgacc agtgctgtcc cagtgctcac agccagggat   1680
gtggctggag ctgttgagtt ctggactgac aggttgggt tctccagaga ttttgtggag    1740
gatgactttg caggtgtggt cagagatgat gtcaccctgt tcatctcagc agtccaggac   1800
caggtggtgc ctgacaacac cctggcttgg gtgtgggtga gaggactgga tgagctgtat   1860
gctgagtgga gtgaggtggt ctccaccaac ttcagggatg ccagtggccc tgccatgaca   1920
gagattggag agcagcccctg ggggagagag tttgccctga gacccagc aggcaactgt    1980 gtgcactttg tggcagagga gcaggactga ggataaccta ggaaaccta aaacctttaa    2040 aagccttata tattctttt tttcttataa aacttaaaac cttagaggct atttaagttg    2100
ctgatttata ttaattttat tgttcaaaca tgagagctta gtacatgaaa catgagagct   2160
tagtacatta gccatgagag cttagtacat tagccatgag ggtttagttc attaaacatg   2220
agagcttagt acattaaaca tgagagctta gtacatacta tcaacaggtt gaactgctga   2280
tc                                                                 2282
```

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gttatcgata ctagtgcgac cgccaaacc                                    29

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caagcggccg ccataccaca tttgtagagg ttttac                            36

<210> SEQ ID NO 28
<211> LENGTH: 25
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 28
caccatggca gatgatttgg acttc                                            25

<210> SEQ ID NO 29
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 30
<211> LENGTH: 3370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
ttaattaaaa ttatctctaa ggcatgtgaa ctggctgtct tggttttcat ctgtacttca      60
tctgctacct ctgtgacctg aaacatattt ataattccat taagctgtgc atatgataga    120
tttatcatat gtattttcct taaggatttt ttgtaagaac taattgaatt gatacctgta    180
aagtctttat cacactaccc aataaataat aaatctcttt gttcagctct ctgtttctat    240
aaatatgtac aagttttatt gttttagtg gtagtgattt tattctcttt ctatatatat     300
acacacacat gtgtgcattc ataaatatat acaatttta tgaataaaaa attattagca     360
atcaatattg aaaccactg attttgtttt atgtgagcaa acagcagatt aaaaggaatt     420
ctcgagtcat cgatactagt gcgaccgcca aaccttagcg gcccagctga caaaagcctg    480
ccctccccca gggtccccgg agagctggtc ctcccctgg gtcccaattt gcatggcagg    540
aaggggcctg gtgaggaaga ggcgggaggg ggacaggctg cagccggtgc agttacacgt    600
```

```
tttcctccaa ggagcctcgg acgttgtcaa gcttctgcct tctccctcct gtgagtttgg    660
taagtcactg actgtctatg cctgggaaag ggtgggcagg agatgggca gtgcaggaaa     720
agtggcacta tgaaccctgc agccctagga atgcatctag acaattgtac taaccttctt    780
ctctttcctc tcctgacagg ttggtgtaca gtagcttcca ccatggcaga tgatttggac    840
ttcgagacag gagatgcagg ggcctcagcc accttcccaa tgcagtgctc agcattacgt    900
aagaatggtt ttgtggtgct caagggccgg ccatgtaaga tcgtcgagat gtctacttcg    960
aagactggca ggcatggcca tgccaaggtc catctggttg gtattgatat ttttactggg    1020
aagaaatatg aagatatctg cccgtcgact cataacatgg atgtccccaa catcaaaagg    1080
aatgatttcc agctgattgg catccaggat gggtacctat ccctgctcca ggacagtggg    1140
gaggtacgag aggaccttcg tctgcctgag ggagaccttg gcaaggagat tgagcagaag    1200
tatgactgtg agaagagagat cctgatcaca gtgctgtccg ccatgacaga ggaggcagct    1260
gttgcaatca aggcgatggc aaaataactg gctagctggc cagacatgat aagatacatt    1320
gatgagtttg acaaaccac aactagaatg cagtgaaaaa aatgctttat ttgtgaaatt     1380
tgtgatgcta ttgctttatt tgtaaccatt ataagctgca ataaacaagt taacaacaac    1440
aattgcattc attttatgtt tcaggttcag ggggaggtgt gggaggtttt ttaaagcaag    1500
taaaacctct acaatgtgg tatggcggcc gcaccaccct gggccaggct gggccaagcc     1560
aggcggcccc tgtgtttcc ccagtctctg ggctgctgga gggaaccagg ttgttttggc     1620
atcagcctct actgagccgg agccttcct ttcctgctgc tttgcatagt ggcactaatt     1680
ccgtcctcct acctccacca gggacctagg cagccgggta gatggtggga ggaggcttca    1740
cttctccccc aagcagggtc tccacctgct tgaggctgcc ctgggttggg ggaggccttg    1800
gctttaccta aagacttttt aacacctcta cgcgtaattc agtcaatatg ttcaccccaa    1860
aaaagctgtt tgttaacttg ccaacctcat tctaaaatgt atatagaagc ccaaaagaca    1920
ataacaaaaa tattcttgta gaacaaaatg ggaagaatg ttccactaaa tatcaagatt     1980
tagagcaaag catgagatgt gtggggatag acagtgaggc tgataaaata gagtagagct    2040
cagaaacaga cccattgata tatgtaagtg acctatgaaa aaaatatggc attttacaat    2100
gggaaaatga tgatcttttt cttttttaga aaacaggga aatatattta tatgtaaaaa     2160
ataaaaggga acccatatgt cataccatac acacaaaaaa attccagtga attataagtc    2220
taaatggaga aggcaaaact ttaaatcttt tagaaaataa tatagaagca tgccatcaag    2280
acttcagtgt agagaaaaat ttcttatgac tcaaagtcct aaccacaaag aaaagattgt    2340
taattagatt gcatgaatat taagacttat ttttaaaatt aaaaaaccat taagaaaagt    2400
caggccatag aatgacagaa atatttgca acaccccagt aaagagaatt gtaatatgca     2460
gattataaaa agaagtctta caaatcagta aaaaataaaa ctagacaaaa atttgaacag    2520
atgaaagaga aactctaaat aatcattaca catgagaaac tcaatctcag aaatcagaga    2580
actatcattg catatacact aaattagaga atattaaaa ggctaagtaa catctgtggc     2640
ttaattaaaa caggtagttg acaattaaac attggcatag tatatctgca tagtataata    2700
caactcacta taggagggcc atcatggcca agttgaccag tgctgtccca gtgctcacag    2760
ccagggatgt ggctggagct gttgagttct ggactgacag gttggggttc tccagagatt    2820
ttgtggagga tgactttgca ggtgtggtca gagatgatgt caccctgttc atctcagcag    2880
tccaggacca ggtggtgcct gacaacaccc tggcttgggt gtgggtgaga ggactggatg    2940
agctgtatgc tgagtggagt gaggtggtct ccaccaactt cagggatgcc agtggccctg    3000
```

```
ccatgacaga gattggagag cagccctggg ggagagagtt tgccctgaga gacccagcag    3060
gcaactgtgt gcactttgtg gcagaggagc aggactgagg ataacctagg aaaccttaaa    3120
acctttaaaa gccttatata ttcttttttt tcttataaaa cttaaaacct tagaggctat    3180
ttaagttgct gatttatatt aattttattg ttcaaacatg agagcttagt acatgaaaca    3240
tgagagctta gtacattagc catgagagct tagtacatta gccatgaggg tttagttcat    3300
taaacatgag agcttagtac attaaacatg agagcttagt acatactatc aacaggttga    3360
actgctgatc                                                           3370
```

```
<210> SEQ ID NO 31
<211> LENGTH: 21
<212> TYPE: DNA
<213> ORGANISM: Homo sapiens
<220> FEATURE:
<223> OTHER INFORMATION: Description of Combined DNA/RNA Molecule: Homo
      sapiens

<400> SEQUENCE: 31
gcuggacucc uccuacacat t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
uguguaggag gaguccagct t                                              21

<210> SEQ ID NO 33
<211> LENGTH: 537
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
```

```
atagggagac ccaagctgga gaccatgtac ccatacgacg tcccagacta cgctggaagc     60
ttaatggcag atgatttgga cttcgagaca ggagatgcag gggcctcagc cacctttcca    120
atgcagtgct cagcattacg taagaatggt tttgtggtgc tcaagggccg gccatgtaag    180
atcgtcgaga tgtctacttc gaagactggc aggcatggcc atgccaaggt ccatctggtt    240
ggtattgata ttttttactgg gaagaaatat gaagatatct gcccgtcgac tcataacatg    300
gatgtcccca acatcaaaag gaatgatttc cagctgattg gcatccagga tgggtaccta    360
tccctgctcc aggacagtgg ggaggtacga gaggaccttc gtctgcctga gggagacctt    420
ggcaaggaga ttgagcagaa gtatgactgt ggagaagaga tcctgatcac agtgctgtcc    480
gccatgacag aggaggcagc tgttgcaatc aaggccatgg caaaataact ggaattc       537
```

```
<210> SEQ ID NO 34
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 34

Met Tyr Pro Tyr Asp Val Pro Asp Tyr Gly Ser Leu Met Ala Asp
1               5                   10                  15

Asp Leu Asp Phe Glu Thr Gly Asp Ala Gly Ala Ser Ala Thr Phe Pro
            20                  25                  30

Met Gln Cys Ser Ala Leu Arg Lys Asn Gly Phe Val Val Leu Lys Gly
        35                  40                  45

Arg Pro Cys Lys Ile Val Glu Met Ser Thr Ser Lys Thr Gly Arg His
50                  55                  60

Gly His Ala Lys Val His Leu Val Gly Ile Asp Ile Phe Thr Gly Lys
65                  70                  75                  80

Lys Tyr Glu Asp Ile Cys Pro Ser Thr His Asn Met Asp Val Pro Asn
                85                  90                  95

Ile Lys Arg Asn Asp Phe Gln Leu Ile Gly Ile Gln Asp Gly Tyr Leu
            100                 105                 110

Ser Leu Leu Gln Asp Ser Gly Glu Val Arg Glu Asp Leu Arg Leu Pro
        115                 120                 125

Glu Gly Asp Leu Gly Lys Glu Ile Glu Gln Lys Tyr Asp Cys Gly Glu
130                 135                 140

Glu Ile Leu Ile Thr Val Leu Ser Ala Met Thr Glu Glu Ala Ala Val
145                 150                 155                 160

Ala Ile Lys Ala Met Ala Lys
                165

<210> SEQ ID NO 35
<211> LENGTH: 154
<212> TYPE: PRT
<213> ORGANISM: Homo sapiens

<400> SEQUENCE: 35

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 36
<211> LENGTH: 154
<212> TYPE: PRT
<213> ORGANISM: Homo sapiens
```

<400> SEQUENCE: 36

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 37
<211> LENGTH: 148
<212> TYPE: PRT
<213> ORGANISM: Homo sapiens

<400> SEQUENCE: 37

Phe Glu Thr Gly Asp Ala Gly Ala Ser Ala Thr Phe Pro Met Gln Cys
1               5                   10                  15

Ser Ala Leu Arg Lys Asn Gly Phe Val Val Leu Lys Gly Arg Pro Cys
            20                  25                  30

Lys Ile Val Glu Met Ser Thr Ser Lys Thr Gly Lys His Gly His Ala
        35                  40                  45

Lys Val His Leu Val Gly Ile Asp Ile Phe Thr Gly Lys Lys Tyr Glu
    50                  55                  60

Asp Ile Cys Pro Ser Thr His Asn Met Asp Val Pro Asn Ile Lys Arg
65                  70                  75                  80

Asn Asp Phe Gln Leu Ile Gly Ile Gln Asp Gly Tyr Leu Ser Leu Leu
                85                  90                  95

Gln Asp Ser Gly Glu Val Arg Glu Asp Leu Arg Leu Pro Glu Gly Asp
            100                 105                 110

Leu Gly Lys Glu Ile Glu Gln Lys Tyr Asp Cys Gly Glu Glu Ile Leu
        115                 120                 125

Ile Thr Val Leu Ser Ala Met Thr Glu Glu Ala Ala Val Ala Ile Lys
    130                 135                 140

Ala Met Ala Lys
145

<210> SEQ ID NO 38
<211> LENGTH: 447
<212> TYPE: DNA
<213> ORGANISM: Homo sapiens

<400> SEQUENCE: 38
ttcgagacag gagatgcagg ggcctcagcc accttcccaa tgcagtgctc agcattacgt    60

```
aagaatggct tgtggtgct caaaggccgg ccatgtaaga tcgtcgagat gtctacttcg    120
aagactggca agcacggcca cgccaaggtc catctggttg gtattgacat ctttactggg    180
aagaaatatg aagatatctg cccgtcaact cataatatgg atgtccccaa catcaaaagg    240
aatgacttcc agctgattgg catccaggat gggtacctat cactgctcca ggacagcggg    300
gaggtacgag aggaccttcg tctccctgag ggagaccttg gcaaggagat tgagcagaag    360
tacgactgtg gagaagagat cctgatcacg gtgctgtctg ccatgacaga ggaggcagct    420
gttgcaatca aggccatggc aaaataa                                       447
```

```
<210> SEQ ID NO 39
<211> LENGTH: 154
<212> TYPE: PRT
<213> ORGANISM: Homo sapiens

<400> SEQUENCE: 39

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 40
<211> LENGTH: 148
<212> TYPE: PRT
<213> ORGANISM: Homo sapiens

<400> SEQUENCE: 40

Phe Glu Thr Gly Asp Ala Gly Ala Ser Ala Thr Phe Pro Met Gln Cys
1               5                   10                  15

Ser Ala Leu Arg Lys Asn Gly Phe Val Val Leu Lys Gly Arg Pro Cys
            20                  25                  30

Lys Ile Val Glu Met Ser Thr Ser Lys Thr Gly Lys His Gly His Ala
        35                  40                  45

Lys Val His Leu Val Gly Ile Asp Ile Phe Thr Gly Lys Lys Tyr Glu
    50                  55                  60

Asp Ile Cys Pro Ser Thr His Asn Met Asp Val Pro Asn Ile Lys Arg
65                  70                  75                  80

Asn Asp Phe Gln Leu Ile Gly Ile Gln Asp Gly Tyr Leu Ser Leu Leu
                85                  90                  95

Gln Asp Ser Gly Glu Val Arg Glu Asp Leu Arg Leu Pro Glu Gly Asp
            100                 105                 110
```

Leu Gly Lys Glu Ile Glu Gln Lys Tyr Asp Cys Gly Glu Glu Ile Leu
        115                 120                 125

Ile Thr Val Leu Ser Ala Met Thr Glu Glu Ala Ala Val Ala Ile Lys
130                 135                 140

Ala Met Ala Lys
145

<210> SEQ ID NO 41
<211> LENGTH: 154
<212> TYPE: PRT
<213> ORGANISM: Homo sapiens

<400> SEQUENCE: 41

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 42
<211> LENGTH: 6
<212> TYPE: PRT
<213> ORGANISM: Homo sapiens

<400> SEQUENCE: 42

Met Ala Asp Asp Leu Asp
1               5

<210> SEQ ID NO 43
<211> LENGTH: 465
<212> TYPE: DNA
<213> ORGANISM: Homo sapiens

<400> SEQUENCE: 43
atggcagatg acttggactt cgagacagga gatgcagggg cctcagccac cttcccaatg    60
cagtgctcag cattacgtaa gaatggcttt gtggtgctca aaggccggcc atgtaagatc   120
gtcgagatgt ctacttcgaa gactggcaag cacggccacg ccaaggtcca tctggttggt   180
attgacatct ttactgggaa gaaatatgaa gatatctgcc cgtcaactca taatatggat   240
gtccccaaca tcaaaaggaa tgacttccag ctgattggca tccaggatgg gtacctatca   300
ctgctccagg acagcgggga ggtacgagag gaccttcgtc tccctgaggg agaccttggc   360
aaggagattg agcagaagta cgactgtgga gaagagatcc tgatcacggt gctgtctgcc   420

```
atgacagagg aggcagctgt tgcaatcaag gccatggcaa aataa              465
```

<210> SEQ ID NO 44
<211> LENGTH: 462
<212> TYPE: DNA
<213> ORGANISM: Homo sapiens

<400> SEQUENCE: 44

```
atggcagacg aaattgattt cactactgga gatgccgggg cttccagcac ttaccctatg   60
cagtgctcgg ccttgcgcaa aaacggcttc gtggtgctca aaggacgacc atgcaaaata  120
gtggagatgt caacttccaa aactggaaag catggtcatg ccaaggttca ccttgttgga  180
attgatattt tcacgggcaa aaaatatgaa gatatttgtc cttctactca aacatggat   240
gttccaaata ttaagagaaa tgattatcaa ctgatatgca ttcaagatgg ttacctttcc  300
ctgctgacag aaactggtga agttcgtgag gatcttaaac tgccagaagg tgaactaggc  360
aaagaaatag agggaaaata caatgcaggt gaagatgtac aggtgtctgt catgtgtgca  420
atgagtgaag aatatgctgt agccataaaa ccctgcaaat aa                    462
```

<210> SEQ ID NO 45
<211> LENGTH: 19
<212> TYPE: DNA
<213> ORGANISM: Homo sapiens

<400> SEQUENCE: 45

```
gctggactcc tcctacaca                                                19
```

<210> SEQ ID NO 46
<211> LENGTH: 19
<212> TYPE: RNA
<213> ORGANISM: Homo sapiens

<400> SEQUENCE: 46

```
gcuggacucc uccuacaca                                                19
```

<210> SEQ ID NO 47
<211> LENGTH: 4
<212> TYPE: PRT
<213> ORGANISM: Homo sapiens

<400> SEQUENCE: 47

Asp Asp Leu Asp
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Glu His Asp
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 49

Asp Glu Val Asp
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Glu Thr Asp
1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Val Ala Asp
1
```